United States Patent [19]

Shanklin, Jr. et al.

[11] Patent Number: 4,597,902

[45] Date of Patent: Jul. 1, 1986

[54] N-(ARYLTHIOALKYL)-N'-(AMINOALKYL-)UREAS

[75] Inventors: James R. Shanklin, Jr.; Christopher P. Johnson, III, both of Richmond, Va.

[73] Assignee: A. H. Robins Company, Incorporated, Richmond, Va.

[21] Appl. No.: 746,740

[22] Filed: Jun. 20, 1985

Related U.S. Application Data

[63] Continuation-in-part of Ser. No. 549,738, Nov. 18, 1983, abandoned, which is a continuation-in-part of Ser. No. 345,452, Feb. 3, 1982, abandoned, which is a continuation-in-part of Ser. No. 265,278, May 20, 1981, abandoned.

[51] Int. Cl.$^4$ .................. C07C 127/17; C07C 157/07; A61K 31/07
[52] U.S. Cl. ............... 262/239 B; 260/501.1; 260/501.17; 260/501.18; 514/255; 514/232; 514/331; 514/428; 514/471; 514/522; 514/586; 514/595; 514/212; 544/159; 544/160; 544/400; 546/205; 546/233; 549/479; 564/26; 564/27; 564/47; 564/48; 564/52; 564/53; 564/54; 564/56; 558/412; 558/413; 558/417
[58] Field of Search ............ 260/465 D, 239 B, 501.1, 260/501.7, 501.18; 544/159, 160, 400; 546/205, 233; 564/26, 27, 47, 48, 52, 53, 54, 56; 549/479; 514/255, 232, 331, 428, 471, 522, 586, 595

[56] References Cited

U.S. PATENT DOCUMENTS

| | | | |
|---|---|---|---|
| 2,344,934 | 3/1944 | West | 564/47 |
| 4,279,911 | 7/1981 | Martin-Smith et al. | 564/237 |
| 4,500,529 | 2/1985 | Shanklin, Jr. et al. | 564/56 |
| 4,558,155 | 12/1985 | Shanklin, Jr. et al. | 564/27 |

OTHER PUBLICATIONS

Koelzer et al, Arzneim. Forsch. 9, pp. 113–120 (1959).

Primary Examiner—Charles F. Warren
Assistant Examiner—R. A. Picard

[57] ABSTRACT

N-(arylthioalkyl)-N'-(aminoalkyl)ureas and thioureas and oxidation derivatives having the formula

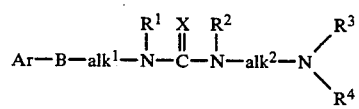

wherein B is thio, sulfinyl or sulfonyl; $R^1$ and $R^2$ are hydrogen, loweralkyl, cycloalkyl, 2-furanyl, phenyl, substituted phenyl or phenyl-loweralkyl and $R^3$ and $R^4$ are hydrogen, loweralkyl, phenyl or phenyl-loweralkyl wherein phenyl is optionally substituted, or $R^3$ and $R^4$ taken with the adjacent nitrogen form a heterocyclic residue.

140 Claims, No Drawings

N-(ARYLTHIOALKYL)-N'-(AMINOALKYL)UREAS

This is a continuation-in-part application of copending application Ser. No. 549,738 filed Nov. 18, 1983, now abandoned, which is a continuation-in-part of application Ser. No. 345,452 fiiled Feb. 3, 1982, now abandoned, which is a continuation-in-part of application Ser. No. 265,278 filed May 20, 1981, now abandoned.

BACKGROUND OF THE INVENTION

1. Field of Invention

The present invention relates to N-(arylthioalkyl)-N'-(aminoalkyl)ureas and thioureas and oxidation derivatives, acid addition salts and hydrates thereof and a method of treating cardiac arrhythmias therewith and pharmaceutical compositions therefor.

2. Information Disclosure Statement

Oxygen analogs:

N'-[2-(Diethylamino]ethyl]-N-methyl-N [2-(phenoxy)ethyl]urea, and

N-Methyl-N-[2-(phenoxy)ethyl]-N'-[2-(pyrrolidinyl)ethyl]urea have been disclosed by Koelzer, P. P. and Wehr, K. H. in Arzneim. Forsch 9, 113–20 (1959). Anesthetic activity in animals was disclosed but clinical use was said to be unlikely.

Oxyen analogs in a method of treating cardiac arrhythmias in animals is the subject of copending application U.S. Ser. No. 265,510 filed May 20, 1981. The oxidation derivatives, the sulfonyl compounds of the present invention have less CNS side effects than the corresponding oxygen analogs.

OBJECTS AND SUMMARY OF THE INVENTION

The present invention is concerned with novel N-(arylthioalkyl)-N'-(aminoalkyl)ureas and thioureas and the oxidation derivatives, the sulfinyl and sulfonyl analogs thereof and methods and compositions for treating cardiac arrhythmias in living animals. The compounds have the following structure formula:

$$Ar-B-alk^1-\underset{\underset{R^1}{|}}{N}-\underset{\underset{X}{\|}}{C}-\underset{\underset{R^2}{|}}{N}-alk^2-N\underset{R^4}{\overset{R^3}{\diagup}}\qquad \text{Formula I}$$

wherein;

Ar is selected from the group consisting of 1 and 2-naphthyl, 2,3-dihydro-1H-inden-4(or 5)yl, 2-furanyl, phenyl or phenyl substituted by 1-3 radicals which may be the same or different selected from the group consisting of lower-alkyl, loweralkoxy, halogen, trifluoromethyl, nitro, cyano, hydroxy, amino, dimethylamino or $$-\underset{\underset{}{\overset{\overset{O}{\|}}{}}}{C}-NR^5R^6,$$

wherein $R^5$ and $R^6$ are selected from hydrogen or loweralkyl, and Ar may include one or two intervening methylene groups attached to B, $R^1$ and $R^2$ are selected from the group consisting of hydrogen, loweralkyl, cycloalkyl, phenyl or phenyl-lower alkyl wherein phenyl may be substituted by halogen, lower-alkyl, loweralkoxy, allyl or loweralkoxy (1-8C)-loweralkyl (2-8C);

X is selected from oxygen or sulfur,

B is selected from the group consisting of thio, sulfinyl or sulfonyl, $R^3$ and $R^4$ are selected from the group consisting of hydrogen, loweralkyl, phenyl and phenyl-loweralkyl wherein phenyl may be substituted by halogen, loweralkyl or lower-alkoxy, and may be the same or different, or $R^3$ and $R^4$ taken together with the adjacent nitrogen form a heterocyclic residue, $alk^1$ and $alk^2$ are selected from the group consisting of loweralkylene or loweralkylene-loweralkyl and may be the same or different, and the pharmaceutically acceptable addition salts and hydrates of the salts and free bases.

Compounds having the following formula are preferred:

$$Ar-B-alk^1-\underset{\underset{R^1}{|}}{N}-\underset{\underset{X}{\|}}{C}-\underset{\underset{R^2}{|}}{N}-alk^2-N\underset{R^4}{\overset{R^3}{\diagup}}$$

wherein;

Ar is selected from the group consisting of 1 and 2-naphthyl, 2,3-dihydro-1H-inden-4(or 5)yl, 2-furanyl, phenyl or phenyl substituted by 1-3 radicals which may be the same or different selected from the group consisting of lower-alkyl, loweralkoxy, halogen, trifluoromethyl, nitro, cyano, or $$-\underset{\underset{}{\overset{\overset{O}{\|}}{}}}{C}-NR^5R^6,$$

wherein $R^5$ and $R^6$ are selected from hydrogen or loweralkyl, and Ar may include one intervening methylene group attached to B, $R^1$ and $R^2$ are selected from the group consisting of hydrogen, loweralkyl, cycloalkyl, phenyl or phenyl-lower alkyl wherein phenyl may be subtituted by halogen, lower-alkyl or loweralkoxy, X is selected from oxygen or sulfur, B is selected from the group consisting of thio, sulfinyl or sulfonyl, $R^3$ and $R^4$ are selected from the group consisting of hydrogen, loweralkyl, phenyl and phenyl-loweralkyl wherein phenyl may be substituted by halogen, loweralkyl or lower-alkoxy, and may be the same or different, or $R^3$ and $R^4$ taken together with the adjacent nitrogen form a heterocyclic residue, $alk^1$ and $alk^2$ are selected from the group consisting of loweralkylene or loweralkylene-loweralkyl and may be the same or different, and the pharmaceutically acceptable addition salts and hydrates of the salts and free bases.

In the further definition of symbols in the formulas hereof and where they appear elsewhere throughout this specification and claims, the terms have the following significance.

The term "loweralkyl" as used herein includes straight and branched chain radicals of up to eight carbons inclusive and is exemplified by such groups as methyl, ethyl, propyl, isopropyl, butyl, sec. butyl, tert-butyl, amyl, isoamyl, hexyl, heptyl, and octyl radicals and the like. The term "loweralkoxy" has the formula —O—loweralkyl. In the term "loweralkoxy (1-8C)- loweralkyl (2-8C), represented by, for example, —CH$_2$CH$_2$—OCH$_3$, the lower limitation of two carbons on the hydrocarbon chain is due to known instability when alkoxy groups are linked to a urea nitrogen by a single methylene group.

The term "cycloalkyl" as used herein includes primarily cyclic alkyl radicals containing 3 to 9 carbon atoms inclusive and includes such groups as cyclopropyl, cyclobutyl, cyclopentyl, cyclohexyl, methylcyclohexyl, cycloheptyl and the like.

The term "halogen" when referred to herein includes fluorine, chlorine, bromine and iodine, preferably fluorine, chlorine and bromine.

The term "loweralkylene" as used herein refers to connecting hydrocarbon groups represented by methylene (—CH$_2$—), ethylene (—CH$_2$—CH$_2$—), propylene (—CH$_2$—CH$_2$—CH$_2$—), and the like. The term "loweralkylene-loweralkyl" is represented by hydrocarbon groups such as ethylidene

1,2-propylene

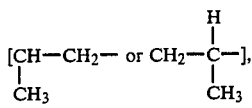

isopropylidene

or 1,3-butylene

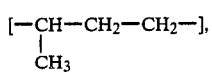

and the like.

The term "heterocyclic residue" as used herein refers to pyrrolidine, piperidine, piperazine, 4-loweralkylpiperazine, morpholine, 4-phenylpiperazine, 2,6-dimethylpiperidine or hexahydro-1H-azepine radicals.

"Pharmaceutically acceptable addition salts" are those salts formed by the N-(arylthioalkyl)-N'-(aminoalkyl)ureas and thioureas and oxidation derivatives of this invention with any acid which is physiologically compatible in warm blooded animals, such salts being formed by either strong or weak acids. Representative of strong acids are hydrochloric, sulfuric and phosphoric acids. Representative of weak acids are fumaric, maleic, succinic, oxalic, citric, tartaric, cyclohexamic and the like.

By "free base" is meant a compound in its non-salt form.

The compounds of the present invention exhibit antiarrhythmic activity in dogs, several arrhythmia models in which arrhythmia is induced by one or more of the following as described more fully hereinbelow under pharmacology: (1) Ouabain, (2) Ligation, (3) Injury), and (4) Acetylcholine.

It is therefore an object of the present invention to provide novel N-(arylthioalkyl)-N'-(aminoalkyl)ureas and thioureas and oxidation derivatives thereof which have a high degree of cardiac activity in animals.

Another object of the invention is to provide methods of treating living animals for the purpose of alleviating cardiac arrhythmias and compositions therefor.

Additional objects will be apparent to one skilled in the art and still other objects will become apparent hereinafter.

DETAILED DESCRIPTION OF THE INVENTION

The method of treating arrhythmias in living animals comprises administering N-(arylthioalkyl)-N'-(aminoalkyl) ureas and thioureas and derivatives thereof as set forth hereinabove in Formula I and definitions therewith and as pharmaceutical compositions to a living animal body for cardiac arrhythmic effect in an amount effective to control arrhythmia.

The compounds of Formula I are prepared by a choice of four methods, A, B, C or D as follows:

METHOD A

This method is represented by the following equation:

$$Ar-B-alk^1NHR^1 + CXCl_2 \xrightarrow{\text{Proton Sponge} \textcircled{R}}$$

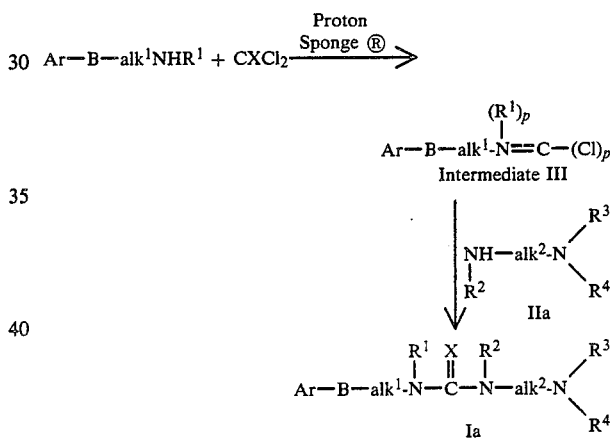

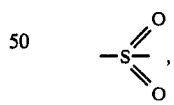

wherein Ar, alk$^1$, alk$^2$, R$^1$, R$^2$, X, R$^3$ and R$^4$ are as defined above and B is S or with the proviso that when R$^2$ is not H, R$^3$ and R$^4$ must be other than hydrogen or R$^2$ is the same as R$^3$ and R$^4$ is hydrogen. In Intermediate III, when p is zero, the double bond as represented by the dotted line is present and the compound is an isocyanate. When p is one, the double bond at the dotted line does not exist. Formula Ia is encompassed by Formula I.

Generally in Method A, the aryl—B—alk$^1$ amine is reacted with phosgene (or thiophosgene) in a suitable organic solvent plus Proton Sponge ® which is the compound, 1,8-bis(dimethylamino)naphthalene, or a tertiary amine organic base such as triethylamine, followed by extraction (washing) with dilute sulfuric acid and the organic layer is dried and evaporated to an oil residue (Intermediate Formula III) which may be isolated if desired. The oil is dissolved in a solvent such as tetrahydrofuran and reacted with an amine of Formula IIa. The reaction mixture is stripped of solvents (to dryness) and the residue partitioned between water and a solvent such as chloroform. Evaporation of the solvent yields an oil which may or may not crystallize. Pharmaceutically acceptable salts may be prepared by reacting with an appropriate acid. The method is illustrated more specifically in Example 1 and other examples utilizing phosgene or thiophosgene.

METHOD B

This method is represented by the following equation:

$$H_2N-alk^2NR^3R^4 + 1,1'\text{-carbonyldiimidazole} + \text{ or } 1,1'\text{-thiocarbonyldiimidazole}$$
$$\text{IIb}$$

$$Ar-B-alk^1-NHR^1$$
$$\text{IVa}$$

$$Ar-B-alk^1-\underset{R^1}{\underset{|}{N}}-\underset{X}{\underset{\|}{C}}-\underset{H}{\underset{|}{N}}-alk^2-NR^3R^4$$
$$\text{Ib}$$

wherein Ar, B, alk$^1$, alk$^2$, R$^1$, R$^3$, R$^4$ and X are as defined hereinabove under Formula I above, except R$^3$ and R$^4$ cannot be H. Formula Ib is encompassed by Formula I and R$^2$ is always hydrogen in this method.

Generally in Method B, an alkyldiamine is reacted first with 1,1'-carbonyldiimidazole in a suitable solvent (e.g., tetrahydrofurn) followed by reaction with a solution of an arylthio, arylsulfinyl or arylsulfonyl alkylamine. The reaction mixture is quenched in water and extracted with a suitable solvent (e.g., methylene chloride) or the reaction mixture is evaporated to dryness and the residue partitioned between water and a suitable solvent. In either case the organic layer is dried and evaporated to yield an oil, the free base. Pharmaceutically acceptable acid addition salts may then be prepared with a suitable acid. The method is illustrated more fully in Example 7.

METHOD C

This method is represented by the following equation:

$$Ar-B-alk^1-NH_2 + 1,1\text{-carbonyldiimidazole} + \text{ or } 1,1'\text{-thiocarbonyldiimidazole}$$
$$\text{IVb}$$
$$R^2NH-alk^2-NR^3R^4$$
$$\text{IIb}$$

$$Ar-B-alk^1-\underset{H}{\underset{|}{N}}-\underset{X}{\underset{\|}{C}}-\underset{R^2}{\underset{|}{N}}-alk^2-N\underset{R^4}{\overset{R^3}{\diagup}}$$
$$\text{Ic}$$

wherein Ar, B, R$^2$, R$^3$, R$^4$ and alk$^2$ are as defined hereinabove, and R$^1$ is always hydrogen in this method. Formula Ic is encompassed by Formula I.

Generally in Method C, Ar—B—alk$^1$—amine is reacted first with 1,1'-carbonyldiimidazole or thiocarbonyldiimidazole in a suitable solvent (e.g., tetrahydrofuran) followed by reaction with an alkyldiamine having one free hydrogen. The solvent is removed by evaporation and the residue partitioned between a suitable solvent (e.g., chloroform) and water. The free base is obtained by evaporation and may be converted to a pharmaceutically acceptable salt with a suitable acid. The method is illustrated more fully in Example 32.

METHOD D

This method is represented by the following equation:

$$\underset{R^4}{\overset{R^3}{\diagdown}}N-alk^2-NHR^2 + CXCl_2 \longrightarrow \underset{R^4}{\overset{R^3}{\diagdown}}N-alk^2-\underset{R^2}{\underset{|}{N}}-\underset{X}{\underset{\|}{C}}Cl$$
$$\text{VI} \qquad\qquad\qquad \text{Intermed. V}$$

$$\text{triethylamine} \Big| + Ar-B-alk^1-NHR^1$$
$$\qquad\qquad\qquad\qquad \text{IVa}$$
$$\downarrow$$

$$Ar-B-alk^1-\underset{R^1}{\underset{|}{N}}-\underset{X}{\underset{\|}{C}}-\underset{R^2}{\underset{|}{N}}-alk^2-N\underset{R^4}{\overset{R^3}{\diagup}}$$
$$\text{Id}$$

wherein Ar, alk$^1$, alk$^2$, B, R$^1$, R$^2$, R$^3$ and R$^4$ have the values assigned above, except R$^2$, R$^3$ and R$^4$ are never hydrogen. Formula Id is encompassed by Formula I.

Generally in Method D, illustrated more fully in Example 33, a trisubstituted diaminoalkyl and phosgene, in a suitable solvent (e.g., methylene chloride) are reacted to give an intermediate product V which may be isolated if desired, which is then reacted with Ar—B—alk$^1$—NHR$^1$ (primary or secondary amine) and trisubstituted amine. The product is isolated by conventional extraction and evaporation methods.

Generally, any compound in the form of an acid addition salt, including intermediates, may be converted to the free base form by dissolving the salt in water, adding excess dilute base such as sodium hydroxide or sodium carbonate and extracting with a solvent such as methylene chloride, drying the solvent layer and evaporating the solvent.

Starting compounds of Formula IVa wherein B is —S— are prepared by reacting aryl—S—alk$^1$—halides with the appropriate amine, and compounds of Formula IVa wherein B is $$-\underset{\|}{\underset{O}{S}}- \quad \text{and} \quad -\underset{\diagdown O}{\underset{\|}{\overset{\diagup O}{S}}}-$$

are obtained by further reaction with sodium perborate. The equations are:

$$Ar-S-alk^1\text{-halo} + NH_2R^1 \xrightarrow[\text{pressure}]{\text{Excess heat}} Ar-S-alk^1NHR^1 \qquad (1)$$
$$\qquad\qquad\qquad\qquad\qquad\qquad\qquad\qquad \text{IVa-1}$$

$$Ar-S-alk^1-NHR^1 \xrightarrow[\text{dilute acid}]{NaBO_3} Ar-\underset{\|}{\underset{O}{S}}-alk^1-NHR^1 \qquad (2)$$
$$\qquad\qquad\qquad\qquad\qquad\qquad\qquad \text{IVa-2}$$

-continued

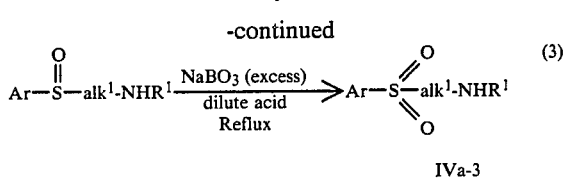

Starting compounds of Formula IVa wherein B is

may also be prepared by reacting arythioalkylamines with phenyl chloroformate followed by oxidation with m-chloroperoxybenzoic acid and hydrolysis with hydrobromic acid. The equations are:

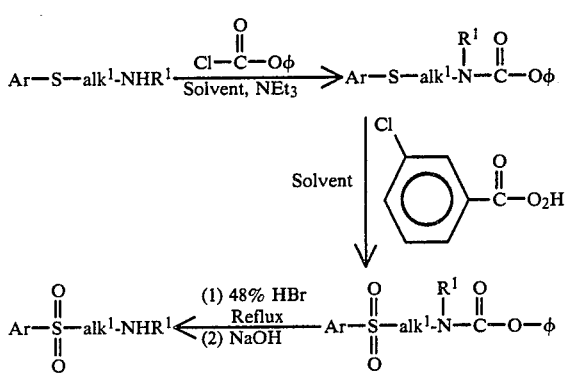

Alternately, starting compounds of Formula IVa wherein B is

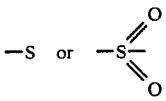

may be prepared via mesyl derivatives as illustrated by the following equations:

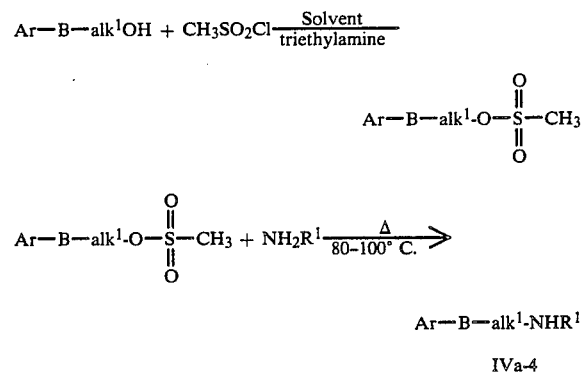

wherein Ar, alk$^1$ and R$^1$ are as defined under Formula I above. Reaction (1) is carried out by heating the reactants in a closed container such as a bomb. Reaction (2) is carried out at room temperature and Reaction (3) is conducted at reflux. Reaction (2) as a step may be omitted by going directly to excess sodium perborate at reflux temperature.

Preparation of compounds of Formula IVa wherein Ar is phenyl substituted by primary amine (i.e., —NH$_2$) is illustrated by the following equations:

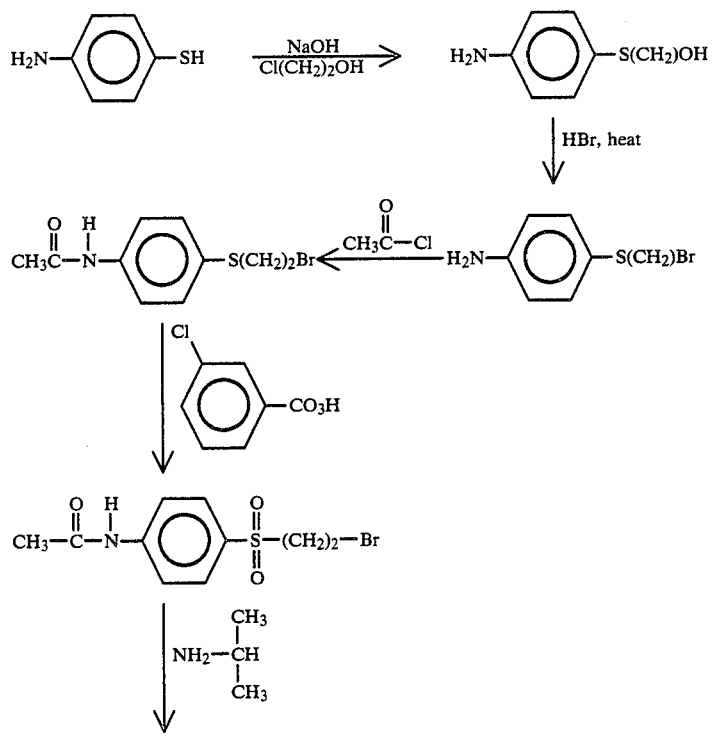

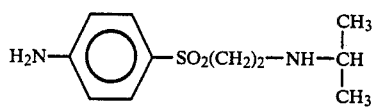

Some of the Ar—B—alk¹—halides starting materials are available commercially. Some of the halides wherein B is sulfur were prepared from metal salts of arylsulfides and α,ω-dihaloalk¹ compounds in refluxing ethanol as represented by the following formula:

Alternately, the chloro starting analogs were prepared from arylsulfide and α-chloro-ω-hydroxy alkanes followed by reaction with thionyl chloride as represented by the following equation:

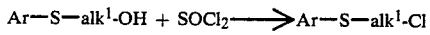

The sulfinyl and sulfonyl starting analogs are obtained by oxidation with hydrogen peroxide in acetic acid as follows:

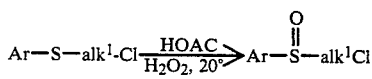

and

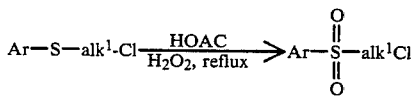

The precursor aryl sulfides may be purchased or prepared as illustrated by the following equation:

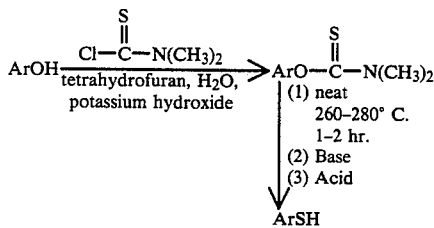

Starting compounds of Formula IVb are prepared as illustrated by the following equation:

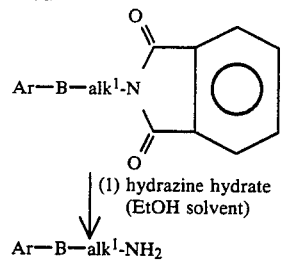

The starting IIb and VI compounds are either purchased or prepared by usual means.

Preparations 1–39, 44–49, 52, 54, 55, 59–62, 63, 65, 70, and 71 provide intermediates of Formula IV, or are used in the preparation thereof, which compounds have the composite formula:

Ar—B—alk¹NR¹R²    (Formula IV)

which encompasses Formulas IVa, IVb and IVc.

Preparations 40–43 illustrate the preparation of compounds of Formula IIb having a phenyl-loweralkyl moiety.

Preparations 50 and 51 illustrate the preparation of certain other compounds of Formula IIb not available commercially.

PREPARATION 1

N-[2-[(4-Chlorophenyl)thio]ethyl]-1-methylethanamine hydrochloride

A solution of 24.0 g (0.116 mole) chloroethyl-p-chlorophenyl sulfide in 100 ml of isopropylamine was agitated overnight in a stainless steel bomb at 80° C. The reaction mixture was then stripped to dryness and the residue partitioned between water and chloroform. The chloroform layer was extracted with 1N sulfuric acid. Three layers were obtained: a water phase (lower), a chloroform phase (upper) and an intermediate phase. The aqueous and intermediate phases were combined, made alkaline and extracted with chloroform. Evaporation yielded an oil, the free base of the title compound. A portion of the oil was reacted with ethereal hydrogen chloride and the resulting hydrochloride salt was recrystallized from methanol-diethyl ether to give 2.23 g (22.6%) of white crystalline product, m.p. 126°–128° C.

Analysis: Calculated for $C_{11}H_{17}NSCl_2$: C, 49.63; H, 6.44; N, 5.26. Found: C, 49.78; H, 6.50; N, 5.50.

PREPARATION 2

1-Methyl-N-[2-(2-naphthalenylthio)ethyl]ethanamine, hydrochloride

2-Naphthalenethiol was prepared by the method of Org. Syn. 51, pp 139–142.

A solution of the potassium salt of 2-naphthalenethiol was prepared by reacting 50.89 g (0.32 mole) of 2-naphthalenethiol and 17.92 g (0.32 mole) of potassium hydroxide in 500 ml ethanol. To the solution was added 297.6 g (1.6 mole) of 1,2-dibromoethane. The solution was refluxed overnight, stripped to dryness and the residue dissolved in chloroform. The chloroform layer was extracted with water and 10% sodium hydroxide. The chloroform layer was evaporated to leave a dark-brown oil as residue which contained about 20% of an unwanted dimer, 1,2-bis naphthalenylthioethane. The impure mixture was stirred overnight with 100 ml of isopropylamine. The reaction mixture was evaporated to dryness and the residue partitioned between chloroform and water. Evaporation of the chloroform layer gave an oil. The oil was triturated with methanol and chilled and a precipitate was filtered off which proved to be the dimer: 1,2-bis-(2-thionaphthylene)ethane. The filtrate was treated with ethereal hydrogen chloride to give the title salt as white crystals weighing 10.2 g (11.3%), m.p. 137.5°–138.5° C.

Analysis: Calculated for $C_{15}H_{20}NSCl$: C, 63.92; H, 7.15; N, 4.97. Found: C, 63.99; H, 7.20; N, 5.10.

PREPARATION 3

N-[2-[(4-Chlorophenyl)sulfinyl]ethyl]-1-methylethanamine

A solution of 15.05 g (0.066 mole) of N-[2-[(4-chlorophenyl)thio]ethyl]-1-methylethanamine and 12.0 g (0.0779 mole) of sodium perborate in 400 ml of 1M sulfuric acid was stirred at room temperature for about 18 hr. The solution was made basic with 50% sodium hydroxide and the basic solution was extracted with methylene chloride. The methylene chloride layer was dried with magnesium sulfate and the solvent removed in vacuo to give 14.7 g of solid. Nuclear magnetic resonance analysis showed a 9 to 1 ratio of sulfoxide to sulfide. The solid was recrystallized from ether-hexane to give 12.3 g (76.4%) of the free base title compound as crystalline solid, m.p. 52.5°–53.5° C.

PREPARATION 4

N-[2-[(4-Chlorophenyl)sulfinyl]ethyl]-1-methylethanamine, maleate[1:1]

A portion of the free base obtained in Preparation 3 was reacted with maleic acid to give the maleate salt which was recrystallized from methanol-diethyl ether to give white crystalline solid, m.p. 158.5°–159° C.

Analysis: Calculated for $C_{15}H_{20}NO_5SCl$: C, 49.79; H, 5.57; N, 3.87. Found: C, 49.91; H, 5.58; N, 3.89.

PREPARATION 5

N-[2-[(4-Chlorophenyl)sulfonyl]ethyl]-1-methylethanamine, hydrochloride

A solution of 51.51 g (0.216 mole) of 2-chloroethyl-p-chlorophenyl sulfone in 400 ml of isopropylamine was stirred at room temperature for about 72 hr. The isopropylamine was removed in vacuo and the residue was dissolved with agitation in a mixture of methylene chloride and dilute sodium hydroxide. The methylene chloride layer was extracted several times with dilute sodium hydroxide and dried over magnesium sulfate. The solvent was removed in vacuo to give 53.5 g oil, the free base of the title compound. A portion of the oil was converted to the hydrochloride salt which was recrystallized from methanol-diethyl ether to give a white crystalline solid, m.p. 169°–170° C.

Analysis: Calculated for $C_{11}H_{17}NO_2SCl_2$: C, 44.30; H, 5.75; N, 4.70. Found: C, 44.37; H, 5.81; N, 4.73.

PREPARATION 6

1-Methyl-N-[2-(phenylsulfonyl)ethyl]ethanamine hydrochloride

A solution of 49.63 g (0.24 mole) of 2-chloroethylphenyl sulfone in 300 ml of isopropylamine was stirred at room temperature for about 20 hr. The isopropylamine was removed in vacuo and the residue was dissolved with agitation in a mixture of methylene chloride and dilute sodium hydroxide. The methylene chloride layer was extracted several times with dilute sodium hydroxide and dried over magnesium sulfate. The solvent was removed in vacuo to give 55.1 g of oil, the free base of the title compound. A portion of the oil was converted to the hydrochloride salt with ethereal hydrogen chloride which was recrystallized from methanol-diethyl ether to give white crystals, m.p. 151°–152.5° C.

Analysis: Calculated for $C_{11}H_{18}NO_2SCl$: C, 50.09; H, 6.88; N, 5.31. Found: C, 50.12; H, 6.91; N, 5.31.

PREPARATION 7

1-[2-[(4-Chlorophenyl)sulfonyl]ethyl]-1H-isoindole-1,3(2H)dione

A mixture of 14.22 g (0.059 mole) of 2-chloroethyl-p-chlorophenylsulfone and 11.60 g (0.06 mole) of potassium phthalimide in 200 ml of dimethylformamide was stirred at 80° C. for 2 hr. The reaction mixture was quenched in water and the white precipitate which resulted was collected by filtration. Recrystallization from diethyl ether gave a white solid, m.p. 154°–155.5° C.

Analysis: Calculated for $C_{16}H_{12}NO_4SCl$: C, 54.94; H, 3.46; N, 4.00. Found: C, 54.60; H, 3.41; N, 3.90.

PREPARATION 8

2-[(4-Chlorophenyl)sulfonyl]ethanamine, monohydrochloride

A solution of 1-[2-(4-chlorophenyl)sulfonyl]ethyl]-1H-isoindole-1,3(2H)dione and 85% hydrazine in 95% ethanol was refluxed for 2 hr. The reaction mixture was quenched in dilute sulfuric acid and the white solid which precipitated was filtered off. The aqueous solution was made basic with sodium hydroxide and extracted with methylene chloride. The methylene chloride layer was dried over magnesium sulfate and the solvent evaporated to give an oil as residue. The oil was dissolved in methanol and the solution treated with an excess of ethereal hydrogen chloride. The product precipitated as a white solid, m.p. 218.5°–219.5° C.

Analysis: Calculated for $C_8H_{11}NO_2SCl_2$: C, 37.51; H, 4.33; N, 5.47. Found: C, 37.52; H, 4.34; N, 5.59.

PREPARATION 9

2-[3-[(4-Chlorophenyl)sulfonyl]propyl]-1,3-dihydro-2H-isoindole-1,3-dione

A solution of 17.8 g (0.07 mole) of 1-chloro-3-(p-chlorophenylsulfonyl)propane and 15.2 g (0.082 mole) of potassium phthalimide in 300 ml of dimethylformamide was stirred at 90°–110° C. for 2 hr and then quenched in water. The mixture was extracted with methylene chloride and the methylene chloride layer dried over magnesium sulfate. Diethylether and hexane were added and the solution stored at 0° C. overnight. The crystalline product was recrystallized from methylene chloride diethyl ether to give a white crystalline product, m.p. 187.5°–188.5° C.

Analysis: Calculated for $C_{17}H_{14}NO_4SCl$: C, 56.12; H, 3.88; N, 3.85. Found: C, 56.10; H, 3.94; N, 3.87.

PREPARATION 10

3-[(4-Chlorophenyl)sulfonyl]-1-propanamine, fumarate[2:1]

A mixture of 55.92 g (0.154 mole) of 2-[3-[(4-chlorophenyl)sulfonyl]propyl]-1,3-dihydro-2H-isoindole-1,3-dione and 11.8 g (0.2 mole) hydrazine hydrate, 85%, was refluxed for 4 hr in 750 ml of 95% ethanol. The reaction mixture was poured into ice, diluted to 3 liters and made alkaline with 10% sodium hydroxide. The diluted mixture was extracted with methylene chloride and the organic phase was extracted with 1N sulfuric acid. The acidic layer was made alkaline and extracted with methylene chloride. Evaporation of the methylene chloride gave an oil which crystallized to a white solid, the free base of the title compound. The oil was reacted with fumaric acid and the salt recrystallized from methanol, yielding 2.95 g (41%) white crystalline product, m.p. 232°–234° C.

Analysis: Calculated for $C_{22}H_{28}N_2O_8S_2Cl_2$: C, 45.29; H, 4.84; N, 4.80. Found: C, 45.45; H, 4.83; N, 4.85.

PREPARATION 11

1-Methyl-N-[2-(1-naphthalenylthio)ethyl]ethanamine, hydrochloride

To a solution of 143.7 g (0.898 mole) of 1-napthalenethiol and 50.3 g (0.898 mole) potassium hydroxide in 1 liter of 95% ethanol, which had stirred for 10 minutes at room temperature, was added 1,843.5 g (4.49 moles) of dibromethane. The resulting solution was heated overnight at gentle reflux, filtered and stripped to dryness. The residue was dissolved in chloroform and extracted with 10% sodium hydroxide. The chloroform layer was evaporated leaving a dark brown oil as residue. The oil was placed in a bomb with 200 ml of isopropyl amine and agitated overnight at 100° C. The mixture was evaporated to give an oil which was extracted with water and 10% aqueous sodium hydroxide solution. The chloroform layer was then extracted with 1N sulfuric acid solution. The acidic layer was made alkaline with 50% sodium hydroxide and extracted with chloroform. Evaporation of the chloroform layer gave a dark brown oil, the free base of the title compound. The oil was reacted with ethereal hydrogen chloride and the salt recrystallized from methanol-diethyl ether to give 44.3 g (17.3%) of white crystalline product, m.p. 121°–122.5° C.

Analysis: Calculated for $C_{15}H_{20}NSCl$: C, 63.92; H, 7.15; N, 4.97. Found: C, 63.67; H, 7.17; N, 4.87.

PREPARATION 12

1-Methyl-N-[2-[(1-naphthalenyl)sulfonyl]ethyl]ethanamine, hydrochloride

To a solution of 12.0 g (0.0426 mole) of 1-methyl-N-[2-(1-naphthalenylthio)ethyl]ethanamine (last oil in Preparation 11) in 500 ml of 2 m $H_2SO_4$ was added 18.4 g (0.12 mole) of sodium perborate tetrahydrate. The mixture was heated overnight at reflux after which time it was determined that approximately half of the starting material had been converted to the sulfoxide and the other half to the sulfone. The mixture was treated with 30.8 g (0.2 mole) more sodium perborate in acid and refluxed. The reaction mixture was cooled with ice and made alkaline with 50% sodium hydroxide and extracted with chloroform. Evaporation of the chloroform layer gave 8.60 g dark-brown oil, the free base of the title compound. A 3 g sample was reacted with ethereal hydrogen chloride and the salt recrystallized from methanol-diethyl ether to give 2.83 g (16.8% yield) of white crystalline solid, m.p. 165°–167° C.

Analysis: Calculated for $C_{15}H_{20}NO_2SCl$: C, 57.41; H, 6.42; N, 4.46. Found: C, 57.33; H, 6.42; N, 4.50.

PREPARATION 13

1-Methyl-N-[2-[(4-methylphenyl)thio]ethyl]ethanamine, hydrochloride

A solution of 10 g (0.035 mole) of 1-p-thiocresyl-2-methanesulfonyl ethane in 50 ml of isopropyl amine was heated at 100° C. overnight in a bomb. The reaction mixture was cooled to room temperature and stripped to dryness. The resulting oil residue was dissolved in chloroform and the solution extracted with 1N sulfuric acid. The acidic layer was carefully basified with 50% aqueous sodium hydroxide and extracted with chloroform. Evaporation of chloroform gave an oil, the free base of the title compound. The oil was reacted with ethereal hydrogen chloride and the salt obtained was recrystallized from methanol-diethyl ether to give 4.5 g (53.1%) of white crystalline solid, m.p. 146°–147° C.

Analysis: Calculated for $C_{12}H_{20}SNCl$: C, 58.64; H, 8.20; N, 5.70. Found: C, 58.64; H, 8.29; N, 5.71.

PREPARATION 14

1-Methyl-N-[2-[(4-methylphenyl)sulfonyl]ethyl]ethanamine, hydrochloride[1:1]

A solution of 7.61 g (0.0346 mole) of 1-methyl-N-[2-[(4-methylphenyl)thio]ethyl]ethanamine (obtained as oil in Preparation 13) and 30.3 g (0.2 mole) of sodium perborate, tetrahydrate in 500 ml of 2N sulfuric acid was refluxed overnight. The reaction mixture was cooled and made alkaline with 50% sodium hydroxide ice mixture and extracted with chloroform. Evaporation of the chloroform layer gave an oil residue, the free base of the title compound. A portion of the oil was reacted with ethereal hydrogen chloride. The salt obtained was recrystallized from methanol-diethyl ether to give a white crystalline product, m.p. 188°–190° C. in 62.5% yield.

Analysis: Calculated for $C_{12}H_{20}NO_2SCl$: C, 51.88; H, 7.26; N, 5.04. Found: C, 51.24; H, 7.20; N, 5.02.

PREPARATION 15

N-[2-(2,3-Dihydro-1H-inden-4-yl)sulfonyl]-1-methylethanamine, and

N-[2-(2,3-Dihydro-1H-inden-5-yl-sulfonyl]-1-methylethanamine 2-(2,3-Dihydro-1-H-inden-4-yl-thiol and 2-(2,3-dihydro-1-H-indene-5-yl thiol are first prepared by the method of Org. Syn. 51, pp 139–142 used for the preparation of 2-naphthalenethiol.

From these thiols are prepared:

1-Methyl-N-[2-(4-indanethio)ethyl]ethanamine and 1-methyl-N-[2-(5-indanethio)ethyl]ethanamine, utilizing the method of Preparation 2. The title compounds are prepared therefrom by hot oxidation with sodium perborate as in Preparation 12.

PREPARATION 16

Following the procedure of Preparation 5, substituting the following for 2-chloroethyl-p-chlorophenyl sulfone:

2-chloroethyl 3,5-dichlorophenyl sulfone, 2-chloroethyl 3,4,5-trimethoxyphenyl sulfone,
2-chloroethyl 4-trifluoromethylphenyl sulfone,
2-chloroethyl 4-cyanophenyl sulfone,
2-chloroethyl 4-nitrophenylsulfone,
there are obtained:
N-[2-[(3,5-dichorophenyl)sulfonyl]ethyl]-1-methylethanamine,
N-[2-[(3,4,5-trimethoxyphenyl)sulfonyl]ethyl]-1-methylethanamine,
1-methyl-N-[2-[4-trifluoromethylphenyl)sulfonyl]ethyl]ethanamine,
N-[2-[(4-cyanophenyl)sulfonyl]ethyl-1-methylethanamine, and
1-methyl-N-[2-[(4-nitrophenyl)sulfonyl]ethyl]ethanamine

PREPARATION 17

Following the procedure of Preparation 6 but substituting the following amines for isopropylamine:
cyclohexylamine,
aniline, and
benzylamine
there are obtained:
N-cyclohexyl-N-[2-(phenylsulfonyl)ethyl]amine,
N-phenyl-N-[2-(phenylsulfonyl)ethyl]amine, and
N-benzyl-N-[2-phenylsulfonyl)ethyl]amine.

PREPARATION 18

1-Methyl-N-[2-(1-naphthalenesulfinyl)ethyl]ethanamine, hydrochloride

A solution of 12.0 g (0.043 mole) of 1-methyl-N-[2-(1-naphthalenylthio)ethyl]ethanamine hydrochloride and 19.7 g (0.028 mole) of sodium perborate tetrahydrate in 500 ml of 2N sulfuric acid was stirred overnight at room temperature. The solution was poured over ice and the mixture was made alkaline with 50% sodium hydroxide and then extracted with chloroform. The chloroform layer was evaporated to give a dark-brown oil, the free base of the title compound, which crystallized at room temperature. A one gram sample was reacted with ethereal hydrogen chloride and recrystallized from methanol-diethyl ether to give 0.72 g (9.1%) of white solid, m.p. 153°–155° C.

Analysis: Calculated for $C_{15}H_{20}NSOCl$: C, 60.49; H, 6.77; N, 4.70. Found: C, 60.17; H, 6.75; N, 4.75.

PREPARATION 19

1-Methyl-N-[2-[(4-methylphenyl)sulfinyl]ethyl]ethanamine, hydrochloride

A solution of 12.3 g (0.05 mole) of 1-methyl-N-[2-[(4-methylphenyl)thio]ethyl]ethanamine (oil in Preparation 13) in 500 ml of 2N sulfuric acid was stirred overnight at room temperature with 23.1 g (0.15 mole) of sodium perborate tetrahydrate. The reaction mixture was made alkaline and extracted with chloroform. Evaporation to remove chloroform gave an oil, the free base of the title compound (11.7 g). A portion of the oil was converted to the hydrochloride, a white salt, (ca. 100% yield), m.p. 127°–128° C., by reacting with ethereal hydrogen chloride.

Analysis: Calculated for $C_{12}H_{20}NSOCl$: C, 55.05; H, 7.70; N, 5.35. Found: C, 54.51; H, 7.68; N, 5.41.

PREPARATION 20

N-[2-[(2,3-Dihydro-1H-inden-4-yl)thio]ethyl]-2-propanamine, hydrochloride

A solution of 42.27 g (0.73 mole) of 1-mesyl-2-(4-thioindane)ethane (purple oil −50%) in 200 ml of isopropylamine was heated at 100° C. overnight in a bomb. The reaction mixture was cooled to room temperature and stripped to dryness. The residue was dissolved in chloroform and extracted with 1N sulfuric acid. The acidic layer was made alkaline and extracted with chloroform. Removal of solvent from the last chloroform layer gave a dark-brown oil. The oil was dissolved in methanol and refrigerated overnight. The solution was filtered to remove a white solid. The filtrate was treated with ethereal hydrogen chloride and refrigerated. A solid was obtained on filtering which, after drying overnight in vacuo, was light brown in color, m.p. 196°–197° C.

Analysis: Calculated for $C_{14}H_{22}NSCl$: C, 61.86; H, 8.16; N, 5.15. Found: C, 62.02; H, 8.19; N, 5.28.

PREPARATION 21

Methanesulfonic Acid [2-[(3,4-dichlorophenyl)thio]ethyl]ester

To a solution of 117.97 g (0.53 mole) of 2-[(3,4-dichlorophenyl)thio]ethanol (prepared by reacting 3,4-dichlorothiophenol and 2-chloroethanol) and 53.5 g (0.53 mole) of triethylamine in 500 ml of benzene was added dropwise a benzene solution of 60.9 g (0.53 mole) of methanesulfonyl chloride over a one hour period with cooling in an ice bath. The reaction mixture was stirred at room temperature overnight and filtered. Solvent was removed from the filtrate in a rotary evaporator to give an oil which crystallized. A portion was recrystallized from isopropyl ether to give white crystalline solid, m.p. 53°–55° C.

Analysis: Calculated for $C_9H_{10}S_2O_3Cl_2$: C, 35.89; H, 3.35. Found: C, 35.81; H, 3.43.

PREPARATION 22

N-[2-[(3,4-Dichlorophenyl)thio]ethyl]-2-propanamine, hydrochloride

A solution of 151.46 g (0.548 mole) of methane-sulfonic acid [2-[(3,4-dichlorophenyl)thio]ethyl]ester in 100 ml of isopropylamine was heated overnight in a bomb at 100° C. The isopropylamine was removed in a rotary evaporator and the residue partitioned between chloroform and 5% sodium hydroxide. The chloroform was removed by rotary evaporator to give an oil, the free base of the title compound. The oil was dissolved in methanol and converted to the hydrochloride salt with ethereal hydrogen chloride. Recrystallization of the salt from methanol-diethyl ether gave 101.53 g (61.6%) of white crystalline product, m.p. 132°–133.5° C.

Analysis: Calculated for $C_{11}H_{16}NSCl_3$: C, 43.94; H, 5.36; N, 4.66. Found: C, 44.09; H, 5.34; N, 4.79.

PREPARATION 23

N,N-Dimethylcarbamothioic Acid-O-(2,3-dihydro-1H-inden-4-yl)ester

A solution of the potassium salt of 4-indanol was prepared by dissolving 20.12 g (0.15 mole) of 4-indanol in 100 ml of water containing 8.40 g (0.15 mole) of potassium hydroxide. The solution was cooled to 0° C. using an ice-salt bath and a solution of 24.8 g (0.2 mole)

of dimethylthiocarbamyl chloride in 100 ml of tetrahydrofuran was added dropwise with stirring while keeping the temperature 0°–5° C. The bath was removed and the reaction mixture stirred for 20–30 minutes. The reaction mixture was made alkaline by adding 50 ml of 10% potassium hydroxide and then extracted with benzene. The benzene layer was then back-extracted with a saturated sodium chloride solution. On evaporation to remove solvent a dark-brown oil residue was obtained which on crystallizing from methanol gave 16.0 g (48.3%) of white crystalline product, m.p. 74°–76° C.

Analysis: Calculated for $C_{12}H_{15}NOS$: C, 65.12; H, 6.83; N, 6.33. Found: C, 64.76; H, 6.80; N, 6.38.

PREPARATION 24

2-[3-(Phenylthio)propyl]-1H-isoindole-1,3-(2H)dione

A solution of 32.86 g (0.177 mole) of 1-chloro-3-(phenylthio)propane and 33.7 g (0.182 mole) of potassium phthalimide in 500 ml of dimethylformamide was stirred at 80° C. for 19 hr. The dimethylformamide was removed in vacuo. The residue was dissolved in methylene chloride and the resulting solution extracted with several portions of dilute sodium hydroxide solution. The methylene chloride layer was dried over magnesium sulfate, filtered, and the filtrate evaporated in vacuo. The resulting solid residue was recrystallized from methylene chloride-hexane to give 33.56 g (63.8%) of white crystalline product, m.p. 83°–85° C.

Analysis: Calculated for $C_{17}H_{15}NO_2S$: C, 68.66; H, 5.08; N, 4.71. Found: C, 68.51; H, 5.07; N, 4.73.

PREPARATION 25

2-[3-(Phenylsulfonyl)propyl]-1H-isoindole-1,3-(2H)dione

To a solution of 30.21 g (0.102 mole) of 2-[3-(phenylthio)propyl]-1H-isoindole-1,3-(2H)dione (oil in Preparation 24) and 65.4 g of 80% (0.304 mole) metachloroperoxybenzoic acid in one liter of methylene chloride which had stirred at room temperature for 5.5 hr was added a saturated aqueous solution of sodium carbonate. The mixture was stirred for ½ hr, the phases separated and the methylene chloride solution extracted with several portions of dilute sodium hydroxide solution. The methylene chloride layer was dried over magnesium sulfate and the solvent removed in vacuo to give an oil. Oil was added to a mixture of methylene chloride-hexane to give 27.56 g (82.1%) of white crystalline product, m.p. 126°–127° C.

Analysis: Calculated for $C_{17}H_{15}NO_4S$: C, 61.99; H, 4.59; N, 4.25. Found: C, 61.84; H, 4.61; N, 4.31.

PREPARATION 26

N-(1-Methylethyl)-3-(phenylsulfonyl)-1-propanamine hydrochloride

A solution of 66.55 g (0.3052 mole) of 3-chloropropylphenyl sulfone (prepared by reacting m-chloroperoxybenzoic acid and 3-chloropropyl phenylsulfide in methylene chloride) in 200 ml of isopropylamine was heated at 100° C. overnight in a bomb. The isopropylamine was removed by rotary evaporation and the residue partitioned between chloroform and water. The chloroform layer was extracted with 1N sulfuric acid. The acidic layer was made alkaline and extracted with chloroform. The combined chloroform extract was evaporated to give an oil, the free base of the title compound. The oil was converted to the hydrochloride salt by reacting with ethereal hydrogen chloride. Recrystallization of the precipitated salt from methanol-diethyl ether gave 48.04 g (65.3%) of white crystalline powder, m.p. 185°–186° C.

Analysis: Calculated for $C_{12}H_{20}NO_2SCl$: C, 51.88; H, 7.26; N, 5.04. Found: C, 51.77; H, 7.27; N, 5.19.

PREPARATION 27

N-[2-[(3,4-Dichlorophenyl)thio]ethyl]-N-(1-methylethyl)carbamic acid phenyl ester To a solution of 29.9 g (0.1 mole) of N-[2-[3,4-dichlorophenyl)thio]ethyl]-2-propanamine and 10.1 g (0.1 mole) of triethylamine in 400 ml of benzene was added a benzene solution of phenyl chloroformate over a ½ hr period. The resulting solution was stirred overnight at room temperature. Chloroform was added and the solution extracted in sequence with water followed by 5% aqueous sodium hydroxide. The organic layer was extracted further with 1N sulfuric acid followed by dilute sodium hydroxide and then evaporated to give an oil. A portion of the oil was dried overnight in vacuo at 80° C.

Analysis: Calculated for $C_{18}H_{19}NO_2SCl_2$: C, 56.25; H, 4.98; N, 3.64. Found: C, 55.89; H, 4.89; N, 3.58.

PREPARATION 28

N-[2-[(3,4-Dichlorophenyl)sulfonyl]ethyl]-N-(1-methylethyl)carbamic acid phenyl ester Following the general procedure of Preparation 32, N-[2-[(3,4-dichlorophenyl)thio]ethyl]-N-(1-methylethyl)carbamic acid phenyl ester was oxidized with metachloroperbenzoic acid to give the title compound.

PREPARATION 29

N-[2-[(3,4-Dichlorophenyl)sulfonyl]ethyl]-2-propanamine

A solution of 44.27 g (0.107 mole) of N-[2-[(3,4-dichlorophenyl)sulfonyl]ethyl]-N-(1-methylethyl)carbamic acid phenyl ester in 300 ml of 48% HBr was heated at reflux for 12 hr. The reaction mixture was cooled to room temperature, made alkaline with 50% sodium hydroxide-ice and extracted with chloroform. The chloroform layer was extracted with 1N sulfuric acid. The sulfuric acid layer was extracted with chloroform and the chloroform layers combined and evaporated to an oil, the free base of the title compound. A portion of the oil was reacted with ethereal hydrogen chloride to give an overall yield of 32.4% white crystaline product, m.p. 219°–221° C.

Analysis: Calculated for $C_{11}H_{15}NO_2SCl_3$: C, 39.84; H, 4.56; N, 4.22. Found: C, 39.62; H, 4.90; N, 4.19.

PREPARATION 30

N-[2-[(4-Fluorophenyl)thio]ethyl]-2-propanamine hydrochloride

A mixture of 70.0 g (0.546 mole) p-fluorothiophenol, 44.0 g (0.546 mole) of 2-chloroethanol and 75.5 g (0.546 mole) of potassium carbonate in 800 ml of acetonitrile was heated overnight at reflux. The reaction mixture was filtered and stripped to dryness. The residue was then partitioned between aqueous sodium hydroxide and chloroform. Solvent was evaporated to give a light brown oil having NMR spectra corresponding to the desired 2-[(4-fluorophenyl)thio]ethanol. The oil was dissolved in 500 ml of benzene and to this solution was added 62.6 g (0.546 mole) of methanesulfonyl chloride over a 30 minute period with cooling using an ice bath.

The resulting mixture was stirred overnight at room temperature, filtered and stripped to dryness. The residue was partitioned between 5% sodium hydroxide solution and chloroform. Chloroform was evaporated to give an oil comprised of about 70% of the methanesulfonic acid ester of 2-[(4-fluorophenyl)thio]ethanol confirmed by NMR spectra. This crude mesylate (125 g) was stirred five days at room temperature with 200 ml of isopropylamine. The reaction mixture was stripped to dryness and partitioned between chloroform and water. The chloroform layer was extracted with 1N sulfuric acid. The acidic layer was made alkaline and extracted with chloroform. The chloroform layers were combined and solvent evaporated to give a brown oil. The oil was reacted with ethereal hydrogen chloride to give the hydrochloride salt. Recrystallization from methanol-diethyl ether gave 41.5 g (30.5% based on p-fluorothiophenol) white crystalline product, m.p. 113.5°–115° C.

Analysis: Calculated for $C_{11}H_{17}NSClF$: C, 52.90; H, 6.86; N, 5.61. Found: C, 52.92; H, 6.88; N, 5.70.

PREPARATION 31

N-[2-[(4-Fluorophenyl)thio]ethyl]-N-(1-methylethyl)-carbamic acid phenyl ester

To a solution of 38.5 g (0.15 mole) of N-[2-(4-fluorophenylthio]ethyl-1-methyl-ethanamine and 15.5 g (0.15 mole) of triethylamine in 300 ml of methylene chloride which was cooled in an ice bath was added dropwise with stirring a solution of 23.5 g (0.15 mole) of phenyl chloroformate in 100 ml of methylene chloride over a 15 minute period. The resulting solution was stirred overnight at room temperature and extracted with 5% aqueous sodium hydroxide. The chloroform layer was dried and filtered and evaporated to give an oil residue which crystallized to a white solid. A portion of the solid was triturated with isopropyl ether and the mixture cooled under refrigeration. The solid was collected by filtration and dried in vacuo overnight at 80° C. White crystalline product, m.p. 53°–58° C. was obtained.

Analysis: Calculated for $C_{18}H_{20}NO_2SF$: C, 64.84; H, 6.05; N, 4.20. Found: C, 64.97; H, 6.06; N, 4.13.

PREPARATION 32

N-[2-[(4-Fluorophenyl)sulfonyl]ethyl]-N-(1-methylethyl)carbamic acid phenyl ester A mixture of 54.76 g (0.164 mole) of N-[2-[(4-fluorophenyl)thio]ethyl]-N-(1-methylethyl)carbamic acid phenyl ester and 179.64 g (0.832 mole) of meta-chloroperbenzoic acid was stirred overnight at room temperature. The resulting mixture was extracted with 5% sodium hydroxide followed by aqueous sodium sulfite. The methylene chloride contained suspension of white solid which was dissolved by adding ethanol. The solution was dried and filtered and solvent evaporated to give an oil which crystallized on standing. A portion of the solid was triturated with isopropyl ether and dried overnight in vacuo at 80° C. to give white crystalline solid, m.p. 94°–95° C.

Analysis: Calculated for $C_{18}H_{20}NO_4SF$: C, 59.16; H, 5.52; N, 3.83. Found: C, 58.87; H, 5.39; N, 3.57.

PREPARATION 33

N-[2-[(4-Fluorophenyl)sulfonyl]ethyl]-2-propanamine hydrochloride

A solution of 60.25 g (0.165 mole) of N-[2-[(4-fluorophenyl)sulfonyl]ethyl]-N-(1-methylethyl)carbamic acid phenyl ester in 400 ml of 48% HBr was heated at reflux for 8 hr. The reaction mixture was cooled with ice and made alkaline with 50% sodium hydroxide. The aqueous phase was extracted with chloroform. The chloroform layer was extracted with sodium hydroxide. Evaporation of the chloroform layer gave an oil residue. The oil was dissolved in methylene chloride and the solution extracted with 1N sulfuric acid. The acidic layer was made alkaline with a mixture of ice and 50% sodium hydroxide solution and extracted with chloroform. Removal of chloroform gave an oil, the free base of the title compound, which was dissolved in methanol and reacted with ethereal hydrogen chloride to give the hydrochloride salt. On recrystallization from methanol-diethyl ether a white crystalline product; m.p. 168°–169° C. in 31.1% yield was obtained.

Analysis: Calculated for $C_{11}H_{17}NO_2SF$: C, 46.89; H, 6.08; N, 4.97. Found: C, 46.71; H, 6.09; N, 4.98.

PREPARATION 34

N-[2-[(4-Methoxyphenyl)sulfonyl]ethyl]-2-propanamine hydrochloride

A solution of 16.46 g (0.055 mole) of N-[2-[(4-chlorophenyl)sulfonyl]ethyl-1-methyl ethanamine hydrochloride and 16.2 g (0.3 mole) of sodium methylate in 500 ml of dimethylsulfoxide was heated at 95° C. for 2 hr. with stirring. The solvent was removed on a rotary evaporator at reduced pressure and the residue was partitioned between water and chloroform. The aqueous phase was made strongly alkaline with 50% sodium hydroxide and extracted with chloroform. The chloroform layers were combined and evaporated to leave an oil. The oil was reacted with ethereal hydrogen chloride. Recrystallization of the salt from methanol-diethyl ether gave 9.11 g (56.4%) of white crystalline product, m.p. 142°–145° C.

Analysis: Calculated for $C_{12}H_{20}NO_3SCl$: C, 49.06; H, 6.86; N, 4.77. Found: C, 48.98; H, 6.91; N, 4.80.

PREPARATION 35

2-[2-(Phenylsulfonyl)ethyl]-1H-isoindole-1,3-(2H)dione

A solution of 30.7 g (0.15 mole) of 2-chloroethylphenylsulfone and 69.5 g (0.375 mole) of potassium phthalimide in 600 ml of dimethylformamide was heated overnight at 85° C. The reaction mixture was stripped to dryness and the residue was partitioned between water and chloroform. The chloroform layer was dried and filtered and solvent was evaporated from the filtrate to give an oil which crystallized on standing. The solid was triturated with isopropyl ether and the mixture cooled under refrigeration. The solid was collected by filtration and dried and recrystallized from methanol-isopropyl ether to give white crystalline product, m.p. 186°–188° C., in 35.7% yield.

Analysis: Calculated for $C_{16}H_{13}NO_4S$: C, 60.94; H, 4.16; N, 4.44. Found: C, 60.70; H, 4.13; N, 4.42.

PREPARATION 36

2-(Phenylsulfonyl)ethanamine hydrochloride

A solution of 32.3 g (0.102 mole) of 2-[2-(phenylsulfonyl)ethyl]-1H-isoindole-1,3-(2H)-dione and 11.8 g (0.2 mole) of 85% hydrazine hydrate in 500 ml of absolute ethanol was refluxed for 6 hr. The reaction mixture was cooled to room temperature, filtered and concentrated. The concentrate was dissolved in chloroform and extracted with 5% sodium hydroxide. The chloroform layer was dried and evaporated to give a clear oil. The oil, the free base of the title compound, was reacted with ethereal hydrogen chloride. Recrystallization of the precipitated salt from methanol-diethyl ether gave white crystalline product, m.p. 151°–154° C. in 40.5% yield.

Analysis: Calculated for $C_8H_{12}NO_2SCl$: C, 43.34; H, 5.46; N, 6.32. Found: C, 43.09; H, 5.44; N, 6.42.

PREPARATION 37

N-[2-[(4-Chlorophenyl)thio]ethyl]-N-(1-methylethyl)-carbamic acid phenyl ester

To a solution of 22.8 g (0.1 mole) of N-[2-[(4-chlorophenyl)thio]ethyl]-1-methylethanamine (oil in Preparation 1) and 10.1 g (0.1 mole) of triethylamine in 300 ml of methylene chloride was added dropwise with stirring a solution of 15.7 g (0.1 mole) phenyl chloroformate in 100 ml of methylene chloride. The resulting solution was stirred overnight at room temperature. The methylene chloride layer was extracted with 5% sodium hydroxide solution followed by 1N sulfuric acid. The methylene chloride layer was concentrated to give an oil which crystallized to a white solid. Recrystallization from isopropyl ether gave white crystalline product, m.p. 54°–56° C. in 79.6% yield.

Analysis: Calculated for $C_{18}H_{20}NO_2SCl$: C, 61.79; H, 5.76; N, 4.00. Found: C, 61.77; H, 5.77; N, 3.98.

PREPARATION 38

N-[2-[(4-Chlorophenyl)sulfonyl]ethyl]-N-(1-methylethyl)carbamic acid phenyl ester To a cold solution of 33.88 (0.089 mole) of N-[2-[(4-chlorophenyl)thio]ethyl]-N-(1-methylethyl)carbamic acid phenyl ester in one liter of methylene chloride was added solid 120.8 g (0.7 mole) of m-chloroperoxybenzoic acid in portions over a 20 minute period. The mixture was stirred overnight at room temperature. The methylene chloride layer was extracted with 5% sodium hydroxide and sodium bisulfite. The methylene chloride layer was concentrated to an oil which crystallized on standing. Recrystallization from isopropyl ether gave white crystalline product, m.p. 77.5°–79.0° C. in 85.3% yield.

PREPARATION 39

N-[2-[(4-Chlorophenyl)sulfonyl]ethyl]-1-methylethanamine hydrochloride

When in the procedure of Preparation 29, N-[2-[(4-chlorophenyl)sulfonyl]ethyl]-N-(1-methylethyl)carbamic acid phenyl ester is substituted for N-[2-[(3,4-dichlorophenyl)sulfonyl]ethyl]-N-(1-methylethyl)carbamic acid phenyl ester, the title compound is obtained.

PREPARATION 40

2-[Methyl(2-phenylethyl)amino]acetonitrile oxalate[1:1]

A mixture of 39.75 g (0.294 mole) of N-methylphenethylamine, 24.0 g (0.32 mole) of chloroacetonitrile and excess sodium carbonate in 700 ml of acetonitrile was refluxed for 18 hr. The solvent was removed in vacuo, and the residue was partitioned between methylene chloride and dilute sodium hydroxide. The methylene chloride solution was dried over magnesium sulfate and the solvent was removed in vacuo to give the free base of the product as a liquid. Part of this was converted to the oxalate salt, and the salt was recrystallized from methanol methanol-ether to give the product as a white crystalline solid, m.p. 102.5°–103.5° C.

Analysis: Calculated for $C_{13}H_{16}N_2O_4$: C, 59.08; H, 6.10; N, 10.60. Found: C, 59.05; H, 6.09; N, 10.47.

PREPARATION 41

N-Methyl-N-(2-phenylethyl)-1,2-ethanediamine oxalate[1:2]hemihydrate

A mixture of 41.23 g. (0.237 mole) of the free base of 2-[methyl-(2-phenylethyl)amino]acetonitrile and 19.7 g (0.52 mole) of lithium aluminum hydride in 800 ml of tetrahydro furan was stirred at room temperature for ~3 hours. The following were added dropwise: (1) 20 ml of water; (2) 80 ml of 5% sodium hydroxide, (3) 40 ml of water. The aluminum hydroxide was filtered from the solution, and the solvent was removed in vacuo. The residue was dissolved in methylene chloride, and the solution was extracted with water and then with 2M sulfuric acid. The acidic extract was made basic with 50% sodium hydroxide, and the basic mixture was extracted with methylene chloride. The methylene chloride solution was dried over magnesium sulfate and the solvent was removed in vacuo to give 37.0 g of the free base of the product as an oil. Part of this was converted to the oxalate salt. This salt was recrystallized from methanol-ether to give the product as a white, crystalline solid, m.p. 165°–166° C. (decomposition.

Analysis: Calculated for $C_{30}H_{46}N_4O_{17}$: C, 49.04; H, 6.31; N, 7.62. Found: C, 49.57; H, 6.10; N, 7.74.

PREPARATION 42

2-[Methyl(phenylmethyl)amino]acetonitrile

A mixture of 121.2 g (1.0 mole) of N-methylbenzylamine and 138.1 g (1.0 mole) of potassium carbonate in 1.2 liters of acetonitrile was refluxed overnight. The reaction mixture was filtered and stripped to dryness. The residue was subjected to vacuum distillation (88°–92° C./0.6 mm). The oil residue was subjected to column chromatography on Florisil ® using hexane-methylene chloride. The oil residue was dried in vacuo overnight at 80° C. to give 5.0 g (30%) of clear oil, the title compound.

Analysis: Calculated for $C_{10}H_{12}N_2$: C, 74.97; H, 7.55; N, 17.48. Found: C, 74.69; H, 7.54; N, 17.48.

PREPARATION 43

N-Methyl-N-(phenylmethyl)-1,2-ethanediamine fumarate[1:2]hemihydrate

A mixture of lithium aluminum hydride (17.5 g, 0.462 mole) in 250 ml of tetrahydrofuran was prepared. To this mixture was added a solution of 61.1 g (0.382 mole) of 2-[methyl(phenylmethyl)amino]acetonitrile in 250 ml of tetrahydrofuran over ½ hour with external cooling via ice bath. The resulting solution was stirred overnight at room temperature. The excess lithium aluminum hydride was destroyed by the addition of 25 ml water (over 2½ hours); 25 ml of 15% sodium hydroxide, and 75 ml of water (over 1½ hours). The reaction mixture was filtered and then stripped to dryness. The resulting oil was diluted to 1000 ml with chloroform and extracted with water. The chloroform was dried, filtered, and solvent removed to give an oil, which was converted to the difumarate and recrystallized from methanol to give 117.5 g (76%) of white crystalline solid, m.p. 135°-138.5° C.

Analysis: Calculated for $C_{18}N_{25}N_2O_{8.5}$: C, 53.33; H, 6.22; N, 6.91. Found: C, 53.45; H, 6.19; N, 7.05.

PREPARATION 44

N-Methyl-2-(phenylsulfonyl)ethanamine

A solution of 2-chloroethylphenyl sulfone and a large excess of methylamine (40% solution in water) in acetonitrile is stirred at room temperature overnight. The solvent is removed in vacuo and the residue is partitioned between methylene chloride and dilute sodium hydroxide. The methylene chloride solution is extracted with dilute sulfuric acid. The acidic extract is made basic with 50% sodium hydroxide and the basic solution is extracted with methylene chloride. The methylene chloride solution is dried over magnesium sulfate and the solvent is removed in vacuo to give the title compound.

PREPARATION 45

N-[2-[(2-Furanylmethyl)thio]ethyl]-2-propanamine hydrochloride

When in the procedure of Preparation 1, 2-chloroethyl furanylmethyl sulfide is substituted for 2-chloroethyl-p-chlorophenyl sulfide, the title compound is obtained.

PREPARATION 46

N-[2-[(2-Furanylmethyl)sulfinyl]ethyl]-2-propanamine

When in the procedure of Preparation 3, N-[(2-[furanylmethyl)thio]ethyl]-2-propanamine is substituted for N-[2-(4-chlorophenyl)thio]ethyl]-1-methylethanamine, the title compound is obtained.

PREPARATION 47

N-[2-[(Phenylmethyl)thio]ethyl]-2-propanamine hydrochloride

When in the procedure of Preparation 1 benzyl 2-chloroethyl sulfide is substituted for 2-chloroethyl-p-chlorophenyl sulfide, the title compound is obtained.

PREPARATION 48

N-[2-[(Phenylmethyl)sulfinyl]-ethyl]-2-propanamine

When in the procedure of Preparation 3, N-[2-[(phenylmethyl)thio]ethyl]-2-propanamine is substituted for N-[2-[(4-chlorophenyl)thio]ethyl]-1-methylethanamine, the title compound is obtained.

PREPARATION 49a to e

Following the procedure of Preparation 5, substituting the following for 2-chloroethyl-p-chlorophenyl sulfone:
2-chloroethyl p-bromophenyl sulfone,
2-chloroethyl 4-t-butylphenyl sulfone,
2-chloroethyl 2-furanylmethyl sulfone,
2-chloroethyl benzyl sulfone, and
2-chloroethyl 3-(trifluoromethyl)phenyl sulfone,
there are obtained:
(a) N-[2-[(4-bromophenyl)sulfonyl]ethyl]-2-propanamine,
(b) N-[2-[(4-t-butylphenyl)sulfonyl]ethyl]-2-propanamine,
(c) N-[2-[(2-furanylmethyl)sulfonyl]ethyl]-2-propanamine,
(d) N-[2-[(phenylmethyl)sulfonyl]ethyl]-2-propanamine, and
(e) N-[2-[3-(trifluoromethyl)phenyl]sulfonyl]ethyl]-2-propanamine.

PREPARATION 50

2-[2-[[N,N-bis(1-Methylethyl)]amino]ethyl]-2H-isoindole-1,3-dione, hydrochloride A solution of 2-diisopropylaminoethyl chloride hydrochloride (40.0 g, 0.2 mole) and potassium phthalimide (74.0 g, 0.4 mole) as stirred overnight at 85° C. in 500 ml of dimethyl formamide. The reaction mixture was stirred to dryness on a rotary evaporator, and the residue was partitioned between chloroform and water. The chloroform layer was extracted with 10% sodium hydroxide. After drying and removal of solvent, a brown oil was obtained which slowly crystallized. A portion of the oil was converted to the hydrochloride salt and recrystallized from methanol/diethyl ether to give 4.18 g (62.3%) of white crystalline product, m.p. 209°-211° C.

Analysis: Calculated for $C_{16}H_{23}N_2O_2Cl$: C, 61.83; H, 7.46; N, 9.01. Found: C, 61.52; H, 7.42; N, 8.93.

PREPARATION 51

N,N-bis(1-Methylethyl)-1,2-ethanediamine, dihydrochloride

A solution of 40.54 g (0.148 mole) of 2-[2-[[N,N-bis(1-methylethyl)amino]ethyl]-2H-isoindole-1,3-dione and hydrazine hydrate (85%, 11.8 g, 0.2 mole) in 400 ml of 95% ethanol was heated at reflux for 5 hours. The reaction mixture was allowed to cool to room temperature while standing overnight. A white solid formed. The reaction mixture was concentrated almost to dryness on the rotary evaporator. The residue was dissolved in chloroform and extracted with 10% sodium hydroxide. After removing chloroform, a brown oil was obtained. A portion of the oil was dissolved in methanol and converted to the dihydrochloride salt. After recrystallization from methanol-diethyl ether, 1.50 g (20%) of white crystalline product, m.p. 178°-182° C. (decomposition) was obtained.

Analysis: Calculated for $C_8H_{22}N_2Cl_2$: C, 44.24; H, 10.21; N, 12.90. Found: C, 43.93; H, 10.15; N, 12.83.

PREPARATION 52

N-[2-(Phenylsulfonyl)ethyl]benzeneethanamine, hydrochloride hemihydrate

A mixture of 70.23 g (0.344 mole) of 2-chloroethylphenylsulfone, 41.92 g (0.343 mole) of phenethylamine and 60 ml of triethylamine in 800 ml of acetonitrile was stirred at room temperature for 18 hr. The solvent was removed in vacuo, and the residue was partitioned between methylene chloride and dilute sodium hydroxide. The methylene chloride solution was dried over magnesium sulfate, and the solvent was removed in vacuo to give an oil. This was dissolved in methanol and excess to ethereal hydrogen chloride was added and ether was added. A white solid precipitated to give 68.39 g (60%) of white crystalline solid, m.p. 194°-196° C.

Analysis: Calculated for $C_{32}H_{42}N_2O_5S_2Cl_2$: C, 57.39; H, 6.32; N, 4.18. Found: C, 56.69; H, 6.44; N, 4.10.

PREPARATION 53

N-(1-Methylethyl)-N-[2-(phenylsulfonyl)ethyl]carbamic chloride

A solution of phosgene in benzene (60 ml of 1.9M phosgene, 12.5% in benzene) in 350 ml of methylene chloride was prepared. To this solution was added a methylene chloride solution of 10.13 g (0.045 mole) of 1-methyl-N-[2-(phenylsulfonyl)ethyl]]ethanamine and Proton Sponge ® 9.55 g, (0.045 mole) over ½ hour. The resulting solution was stirred 2 hours at room temperature and extracted with 1N sulfuric acid. The methylene chloride solution was dried over anhydrous potassium carbonate, filtered, and solvent removed to give a blue oil. The oil was triturated with diethyl ether, and a white solid crystallized in about two minutes. The solid was dried overnight in vacuo at 80° C. to give 9.57 g (73.4%) of white crystalline solid, m.p. 79°–81° C.

Analysis: Calculated for $C_{12}H_{16}NO_3SCl$: C, 49.74; H, 5.56; N, 4.83. Found: C, 49.89; H, 5.62; N, 4.86.

PREPARATION 54

N-Ethyl-2-(phenylsulfonyl)ethanamine hydrochloride[1:1]

Chloroethylphenyl sulfone (46.5 g, 0.227 mole) was stirred at room temperature with ethylamine (70% aqueous, 147 g, 2.25 mole) in 150 ml of Ethanol 200 for 72 hours. The solvents were evaporated to give an oil which was partitioned between 4N sodium hydroxide and methylene chloride. The aqueous layer was extracted once more with methylene chloride and the combined methylene chloride layers were washed with water. The methylene chloride layer was dried over anhydrous sodium sulfate, filtered and evaporated to give 49.1 g of an oil. 1.5 g of this oil was dissolved in methanol and diethyl ether and ethereal hydrogen chloride was added to give a solid. Methanol was added and heat was applied to give a solution which, upon cooling, crystallized. The solid (1.0 g) was collected, m.p. 126°–127.5° C.

Analysis: Calculated for $C_{10}H_{16}NO_2SCl$: C, 48.09; H, 6.46; N, 5.61. Found: C, 48.11; H, 6.55; N, 5.60.

PREPARATION 55

N-(1-Methylethyl)-5-(phenylsulfonyl)-1-pentamine oxalate[1:1]

A solution of 5-chloropentyl phenyl sulfone (99.52 g, 0.404 mole) was agitated overnight at 80°–85° C. in a metal bomb with isopropylamine (138.8 g, 2.34 mole, 200 ml). The reaction mixture was stripped to dryness and the resulting residue was dissolved in chloroform. The chloroform layer was extracted several times with water. The chloroform layer was extracted with 1N sulfuric acid. The acid layer was then made alkaline (ice/50% sodium hydroxide) and extracted with chloroform. The chloroform layer was dried, filtered, and solvent removed to give an oil. The oil was converted to the oxalate salt and the salt recrystallized from methanol-diethyl ether. The white solid obtained was dried overnight in vacuo at 80° C. This furnished 25.86 g (16.6%) of white crystalline solid, m.p. 119°–121° C.

Analysis: Calculated for $C_{16}H_{25}NO_6S$: C, 53.46; H, 7.01; H, 3.90. Found: C, 53.57; H, 7.05; N, 3.89.

PREPARATION 56

N-(1-Methylethyl)-4-(phenylsulfonyl)-1-butanamine hydrochloride[1:1]

A solution of 105.95 g (0.456 mole) [(4-chlorobutyl)sulfonyl]benzene was heated overnight at 75° C. on an autoclave in 200 ml of isopropylamine. The reaction mixture was stripped to dryness. The residue obtained was dissolved in chloroform and the chloroform layer was extracted with water. The chloroform layer was dried, filtered, and solvent removed to give a dark brown oil. The oil was dissolved in methanol and converted to the hydrochloride salt. This salt was recrystallized from methanol-diethyl ether and dried in vacuo overnight at 80° C. This gave white crystalline product, m.p. 155°–157.5° C. in 30% yield.

Analysis: Calculated for $C_{13}H_{22}NO_2SCl$: C, 53.50; H, 7.60; N, 4.80. Found: C, 53.41; H, 7.62; N, 4.76.

PREPARATION 57

2-[[4-(1,1-Dimethylethyl)]thio]ethanol

A mixture of 50 g (0.301 mole) of 4-t-butylthiophenol, 26.4 g (0.33 mole) of 2-chloroethanol and excess potassium carbonate in 1 liter of acetonitrile was refluxed for 20 hr. The solvent was removed in vacuo, and the residue was partitioned between methylene chloride and the dilute sodium hydroxide. The methylene chloride was dried over magnesium sulfate, and the solvent was removed in vacuo to give a liquid. This was vacuum distilled (140°–143° C., 0.44 mm) to give 46.52 g (73.6%) of clear colorless liquid.

Analysis: Calculated for $C_{12}H_{18}OS$: C, 68.52; H, 8.63. Found: C, 68.51; H, 8.67.

PREPARATION 58

1-[(2-Chloroethyl)sulfonyl]-4-1,1-dimethylethyl)benzene

A solution of 44.37 g (0.21 mole) of 2-(4-t-butylphenylthio)-1-ethanol in 200 ml of thionyl chloride was refluxed for 2 hr. The solvent was removed in vacuo, and the residue was dissolved in 300 ml of hexane. The solvent was removed in vacuo to give a black oil. This was vacuum distilled, and the fractions boiling at 123°–124° C. (0.27 mm) were collected to give 37.97 g of a clear, colorless liquid. This was shown by NMR to be an 85/15 mixture of 1-[chloroethyl)sulfonyl]-4-(1,1-dimethylethyl)benzene and 1-(1,1-dimethylethyl)-4-(1-ethenylsulfonyl)benzene, respectively. A solution of this mixture in 100 ml of benzene was slowly added to a solution of 61.6 g (0.357 mole) of meta-chloroperoxybenzoic acid in 1 liter of benzene. The solution was stirred at room temperature for 2 hr and then was extracted with several portions of dilute sodium hydroxide. The benzene solution was dried over magnesium sulfate, and the solvent was removed in vacuo to give a white solid. This was recrystallized from a mixture of ethyl ether-methylene-chloride-hexane to give 22.51 g (41.2%) of a white crystalline solid, m.p. 105°–106.5° C.

Analysis: Calculated for $C_{12}H_{17}O_2ClS$: C, 55.27; H, 6.57. Found: C, 55.33; H, 6.59.

PREPARATION 59

N-[2-[[4-(1,1-Dimethylethyl)phenyl]sulfonyl]ethyl]-2-propanamine hydrochloride[1:1]

A solution of 21.4 g (0.082 mole) of 4-t-butylphenyl-2-chloroethyl sulfone in 400 ml of isopropylamine was stirred at room temperature for 20 hr. The solvent was removed in vacuo, and the residue was partitioned between methylene chloride and dilute sodium hydroxide. The methylene chloride solution was dried over magnesium sulfate, and the solvent was removed in vacuo. The residue was dissolved in 200 ml of methanol, and the solvent was removed in vacuo to give an oil. This was pumped under aspirator vacuum at 50° C. for 2 hr. The oil was dissolved in 300 ml of methanol, an excess of ethereal hydrogen chloride was added, and ether was added. A white precipitate formed to give 21.15 g (80.68%) of white, crystalline solid, m.p. 213°–214° C.

Analysis: Calculated for $C_{15}N_{25}NO_2S$: C, 56.32; H, 8.12; N, 4.38. Found: C, 56.38; H, 8.33; N, 4.39

PREPARATION 60

N-[2-(Phenylthio)ethyl]-2-propanamine hydrochloride[1:1]

A solution of 25 g (0.145 mole) of 2-chloroethyl phenyl sulfide and 1 g (0.006 mole) of potassium iodide in 500 ml of isopropylamine was heated in a bomb at 120° C. for 24 hr. The solvent was removed in vacuo, and the residue was partitioned between methylene chloride and dilute sodium hydroxide. The methylene chloride solution was extracted with dilute sulfuric acid. The acidic extract was made basic with 50% sodium hydroxide, and the basic solution was extracted with methylene chloride. The methylene chloride solution was dried over magnesium sulfate and the solvent was removed in vacuo to given an oil. This was converted to the hydrochloride salt, and the salt was recrystallized from methanol-ether to give 25.77 g (76.9%) of white crystalline solid, m.p. 124.5°–125.5° C.

Analysis: Calculated for $C_{11}H_{18}NSCl$: C, 57.00; H, 7.83; N, 6.04. Found: C, 56.95; H, 8.00; N, 6.05.

PREPARATION 61

N-[2-[(Phenylmethyl)sulfonyl]ethyl]-2-propanamine hydrochloride[1:1]

A mixture of 51.49 g (0.236 mole) of benzyl 2-chloroethyl sulfone and 600 ml of isopropylamine was stirred at room temperature for 72 hr. The solvent was removed in vacuo, and the residue was partitioned between ether and dilute sodium hydroxide. The ether solution was dried over magnesium sulfate, and the solvent was removed in vacuo to give an oil. This was dissolved in methanol, and excess ethereal hydrogen chloride was added. Ether was added, and a white solid precipitated to give 43.11 g (65.8%) of a white crystalline solid, m.p. 180.5°–181.5° C.

Analysis: Calculated for $C_{12}H_{20}NO_2SCl$: C, 51.88; H, 7.26; N, 5.04. Found: C, 52.02; H, 7.40; N, 5.04.

PREPARATION 62

N-[-(Phenylsulfinyl)ethyl]-2-propanamine maleate[1:1]

A solution of 15.62 g (0.067 mole) of N-[2-(phenylthio)ethyl]-2-propanamine hydrochloride and 15.62 g (0.101 mole) of sodium perborate tetrahydrate in 300 ml of 2M sulfuric acid was stirred at room temperature for 16 hr. The solution was made basic with 50% sodium hydroxide, and the basic solution was extracted with methylene chloride. The methylene chloride solution was dried over magnesium sulfate, and the solvent was removed in vacuo. The residue was dissolved in ether, a solution of maleic acid in methanol was added, and precipitated to give 19.48 g (88.3%) of white solid, m.p. 102.5°–103.5° C. A sample of this was recrystallized from methanol-ether, m.p. 102.5°–103.5° C.

Analysis: Calculated for $C_{15}H_{21}NSO_5$: C, 55.03; H, 6.47; N, 4.28. Found: C, 55.09; H, 6.50; N, 4.27.

PREPARATION 63

N-[2-(Phenylsulfonyl)ethyl]benzenemethanamine hydrochloride[1:1]

A mixture of 71.90 g (0.352 mole) of 2-chloroethyl phenyl sulfone, 37.45 g (0.350 mole) of benzylamine and 60 ml of triethylamine in 800 ml of acetonitrile was stirred at room temperature for ≈64 hr. The solvent was removed in vacuo and the residue was partitioned between methylene chloride and dilute sodium hydroxide. The methylene chloride solution was dried over magnesium sulfate, and the volume was reduced in vacuo to 300 ml. Methanol was added followed by an excess of ethereal hydrogen chloride. A white precipitate was collected to give 81.30 g (74.5%) of white, crystalline solid, m.p. 211°–213° C.

Analysis: Calculated for $C_{15}H_{18}NSO_2Cl$: C, 57.78; H, 5.82; N, 4.49. Found: C, 57.93; H, 5.91; N, 4.48.

PREPARATION 64

1-(Phenylsulfonyl)-2-propanol

A mixture of 78.97 g (0.47 mole) of 1-thiophenoxy-2-propanol and 200 g (1.16 mole) of meta-chlorophenoxy benzoic acid in 1 liter of chloroform was stirred at room temperature for 3.5 hr. The reaction mixture was extracted with three portions of dilute sodium hydroxide and then with a saturated aqueous solution of sodium bisulfite. The chloroform solution was dried over magnesium sulfate, and the solvent was removed in vacuo to give a solid. This was recrystallized from ether-hexane to give 44.56 g (47.3%) of title compound, m.p. 44°–47° C.

Analysis: Calculated for $C_9H_{12}SO_3$: C, 53.98; H, 6.04. Found: C, 53.94; H, 6.06.

PREPARATION 65

N-(1-Methylethyl)-1-(phenylsulfonyl)-2-propanamine hydrochloride[1:1]

A solution of 30.5 g (0.153 mole) of 1-(phenylsulfonyl)-2-propanol in 200 ml of thionyl chloride was refluxed for two hr. The solvent was removed in vacuo. Benzene (200 ml) was added, and the solvent was removed in vacuo. This was repeated. Isopropylamine (200 ml) was added and the mixture was stirred at room temperature overnight. The solvent was removed in vacuo, and the residue was partitioned between methylene chloride and dilute sodium hydroxide. The methylene chloride solution was extracted with dilute sulfuric acid. The acidic extract was made basic with 50% sodium hydroxide, and the basic solution was extracted with methylene chloride. The methylene chloride was dried over magnesium sulfate, and the solvent was removed in vacuo to give an oil. This was dissolved in methanol, an excess ethereal hydrogen chloride was added, and ether was added. A white solid precipitated to give 12.8 g (28.5%) of white crystalline solid, m.p. 170°–172° C.

Analysis: Calculated for $C_{12}H_{20}NO_2SCl$: C, 51.88; H, 7.26; N, 5.04. Found: C, 51.76; H, 7.32; N, 5.01.

PREPARATION 66

4-(Phenylthio)-1-butanol

A mixture of thiophenol (121.2 g, 1.10 mole), 4-chloro-1-butanol (100.0 g, 0.921 mole), and potassium carbonate (138.2 g, 1.0 mole) was heated overnight at gentle reflux in dimethoxyethane. The reaction mixture was filtered and solvent removed by rotary evaporator. The residue obtained was dissolved in chloroform and extracted with 10% sodium hydroxide. The chloroform layer was dried, filtered, and solvent removed to give an oil which crystallized to a white solid. The solid was vacuum distilled at 134°–140° C./0.55 mm. A six-gram sample of the distilled oil was subjected to flash chromatography on silica gel using ethyl acetate-hexanes for elution. This gave a clear oil which was dried at 80° C. overnight in vacuo. The process produced 5.2 g (57.8%) of clear oil.

$^1$H NMR (CDCl$_3$) o 7.1–7.4 (m, 5, aromatic), 3.6–3.8 (m, 2, o—CH$_2$), 2.7–3.1 (m, 2, 5—CH$_2$), 2.3 (5, 1, OH), 1.5–1.8 (m, 4, —CH$_2$CH$_2$).

Analysis: Calculated for C$_{10}$H$_{14}$SO: C, 65.89; H, 7.74. Found: C, 65.57; H, 7.72.

PREPARATION 67

[(4-Chlorobutyl)sulfonyl]benzene

A slurry of meta-chloroperbenzoic acid (270.3 g, 1.25 mole) on 700 ml of chloroform was stirred overnight at room temperature with chlorobutylphenylsulfide (84.26 g, 0.42 mole). The slurry was filtered and the chloroform layer was extracted with potassium carbonate and sodium bicarbonate solutions. The chloroform layer was also extracted with aqueous sodium bisulfite. The chloroform layer was dried, filtered, and solvent removed to give a yellow oil which crystallized on standing at room temperature to give a white solid. A seven-gram portion of the solid was subjected to flash chromatography on silica gel using 20% ethyl acetatehexanes and 25% ethyl acetate-hexanes for elution. Fractions from the column were combined, and the resulting oil dried in vacuo at room temperature overnight. The oil crystallized to a white solid. The process furnished 5.03 g (83.3%) of white crystalline product, m.p. 55°–58° C.

Analysis: Calculated for C$_{10}$H$_{13}$SO$_2$Cl: C, 51.61; H, 5.63. Found: C, 51.78; H, 5.64.

PREPARATION 68

3-Ethoxy-N-[2-(phenylsulfonyl)ethyl]-1-propanamine hydrochloride

A mixture of 51.4 g (0.253 mole) of 2-chloroethyl phenyl sulfone, 50.2 g (0.417 mole) of 3-ethoxy-1-propanamine, and 33.0 g (0.327 mole) of triethylamine in 400 ml of acetonitrile was stirred at room temperature for 20 hr. The solvent was removed in vacuo and the residue was partitioned between methylene chloride and dilute sodium hydroxide. The methylene chloride phase was dried over magnesium sulfate, and the solvent was removed in vacuo to give an oil. This was dissolved in methanol, an excess of ethereal hydrogen chloride was added and ether was added. A precipitate was collected to give 49.2 g (63.2%) of white crystalline solid, m.p. 169°–170° C.

Analysis: Calculated for C$_{13}$H$_{22}$NO$_3$SCl: C, 50.72; H, 7.20; N, 4.55. Found: C, 50.72; H, 7.28; N, 4.53.

PREPARATION 69

N-(2-Methoxyethyl)-1-(phenylsulfonyl)ethanamine oxalate[1:1]

A mixture of 44.6 g (0.22 mole) of 2-chloroethyl phenyl sulfone, 56.0 g (0.75 mole) of 2-methoxy-1-ethanamine and 44.0 g (0.44 mole) of triethylamine in 600 ml of acetonitrile was stirred at room temperature for 16 hr. The solvent was removed in vacuo, and the residue was partitioned between ether and dilute sodium hydroxide. The ether solution was dried (magnesium sulfate), and the solvent was removed in vacuo to give 37.66 g (71.1%) of the free base of the title compound as an oil. This was converted to the oxalate salt, and the salt was crystallized from methanol ether to give 48.55 g (66.8%) of white crystalline solid, m.p. 203.5°–204.5° C.

Analysis: Calculated for C$_{13}$H$_{19}$NO$_7$S: C, 46.84; H, 5.75; N, 4.20. Found: C, 46.65; H, 5.72; N, 4.17.

PREPARATION 70

N-[2-[(4-Ethoxyphenyl)sulfonyl]ethyl]-2-propanamine hydrochloride[1:1]

To a suspension of 6.6 g of a 60% dispersion of sodium hydride in oil (0.165 mole) in 300 mole of dimethyl sulfoxide was added 7.5 g (0.163 mole) of absolute ethanol. The mixture was stirred at room temperature for 0.5 hr, and 20.8 g (0.080 mole) of N-[2-(4-chlorophenyl-sulfonyl)ethyl]-2-propanamine hydrochloride was added as a solid. The mixture was heated at 120°–140° C. for 1 hr, and the solvent was removed in vacuo. The residue was partitioned between methylene chloride and dilute sodium hydroxide. The methylene chloride solution was dried over magnesium sulfate, and the solvent was removed in vacuo. The residue was dissolved in methanol, an excess of ethereal hydrogen chloride was added, and ether was added. A white solid precipitated in amount of 14.92 g (69.2%), m.p. 168°–170° C.

Analysis: Calculated for C$_{13}$H$_{22}$NO$_3$SCl: C, 50.72; H, 7.20; N, 4.55. Found: C, 50.73; H, 7.31; N, 4.59.

PREPARATION 71

N-[2-(Phenylsulfonyl)ethyl]-2-propen-1-amine maleate[1:1]

A mixture of 52.26 g (0.256 mole) of 2-chloroethyl-phenyl sulfone and 39.2 g (0.69 mole) of vinylamine in 1 liter of acetonitrile was stirred at room temperature for 16 hr. The solvent was removed in vacuo, and the residue was partitioned between diethyl ether and dilute sodium hydroxide. The ether phase was dried over magnesium sulfate, and the solvent was removed in vacuo to give the non-salt form of the title compound as an oil. This was converted to the maleate salt, and the salt was recrystallized from methanol-diethyl ether to give 67.0 g (76.7%) of white crystalline solid, m.p. 144°–145° C.

Analysis: Calculated for C$_{15}$H$_{19}$NO$_6$S: C, 52.78; H, 5.61; N, 4.10. Found: C, 52.90; H, 5.60; N, 4.08.

PREPARATION 72

N-[2-[(4-Hydroxyphenyl)sulfonyl]ethyl]-2-propanamine hydrochloride

A solution of N-[2-[(4-chlorophenyl)sulfonyl]ethyl]-1-methylethanamine hydrochloride and sodium hydroxide in 500 ml of dimethyl sulfoxide is heated at 95°

C. for 2 hrs with stirring. The solvent is removed by rotary evaporation (vacuum pump) and the residue is partitioned between water (pH adjusted to 7 by the addition of dilute hydrochloric acid) and chloroform. The chloroform is removed and the residue is converted to the hydrochloride salt with ethereal hydrogen chloride. The salt is then recrystallized from methanol-diethyl ether to give crystalline title compound.

PREPARATION 73

N-[2-[(4-Dimethylaminophenyl)sulfonyl]ethyl]-2-propanamine

2-Chloroethyl-4-dimethylamino phenyl sulfone is reacted as in Preparation 5 with isopropylamine to give the titled compound.

The following examples serve to illustrate the preparation of the compounds useful in treating arrhythmias in the method of this invention. The scope of the invention is, however, not limited thereto. Structures are illustrated in Table 1.

EXAMPLE 1

N-[2-[(4-Chlorophenyl)thio]ethyl]-N'-[2-(dimethylamino)ethyl]-N-(1-methylethyl)urea, fumarate[1:1.5]

To a solution of 25 ml of 12.5% phosgene in benzene (0.0475 mole) and 6.42 g Proton Sponge ®, [1,8-bis-(dimethylamino)naphthalene] (0.03 mole) in 300 ml of methylene chloride was added a methylene chloride solution containing 6.87 g (0.03 mole) of N-[2-[(4-chlorophenyl)thio]ethyl]-1-methylethanamine (oil in Preparation 1) over a 45 min period. The solutions was stirred for 2.5 hr at room temperature and extracted with 1N aqueous sulfuric acid solution. The methylene chloride layer was dried over anhydrous potassium carbonate. The organic solvent was removed in a rotary evaporator to give an oil residue which was then dissolved in tetrahydrofuran. To this solution was added 5.28 g (0.06 mole) of N,N-dimethylethylenediamine (unsym-dimethyl ethylenediamine). The reaction mixture was stripped to dryness and the residue partitioned between water and chloroform followed by washing of the chloroform layer several times with water. The chloroform layer was evaporated to give a yellow oil, the free base of the title compound, which was reacted with fumaric acid to give crystalline solid. Recrystallization from methanol-diethyl ether gave 6.86 g (44.1%) of white crystalline product, m.p. 101°–103.5° C.

Analysis: Calculated for $C_{22}H_{32}N_3O_7SCl$: C, 51.00; H, 6.23; N, 8.11. Found: C, 50.65; H, 6.20; N, 8.17.

EXAMPLE 2

N'-[2-(Dimethylamino)ethyl]-N-(1-methylethyl)-N-[2-[(2-naphthylene)thio]ethyl]urea succinate[1:1.5]

The title compound was prepared by Method A and the procedure of Example 1, reacting in sequence:

0.0475 mole phosgene; Proton Sponge ®, 5.81 g (0.0237 mole) of 1-methyl-N-[2-(2naphthylenylthio)ethyl]ethanamine (from neutralizing the hydrochloride obtained in Preparation 2), 4.40 g (0.05 mole) unsym-N,N-dimethylethylenediamine to give an oil, the free base of the title compound, which was then reacted with succinic acid, (45.3%), m.p. 96°–98° C.

Analysis: Calculated for $C_{26}H_{38}N_3O_7S$: C, 58.19; H, 7.14; N, 7.83. Found: C, 58.06; H, 7.16; N, 7.75.

EXAMPLE 3

N-[2-[(4-Chlorophenyl)sulfonyl]ethyl]-N'-[2-(dimethylamino)ethyl]-N-(1-methylethyl)urea maleate[1:1]

The title compound was prepared by Method A and the procedure of Example 1, reacting in sequence:

0.0475 mole phosgene, Proton Sponge ®, 6.53 g (0.025 mole) of N-[2-[(4-chlorophenyl)sulfonyl]ethyl]-1-methylethanamine (oil in Preparation 5), 4.20 g (0.05 mole) unsym-dimethylethylenediamine to give an oil, the free base of the title compound which was then reacted with maleic acid (73.5%), m.p. 134°–135° C.

Analysis: Calculated for $C_{20}H_{30}N_3O_7ClS$: C, 48.83; H, 6.15; N, 8.54. Found: C, 48.76; H, 6.15; N, 8.57.

EXAMPLE 4

N-[2-[(4-Chlorophenyl)sulfonyl]ethyl]-N'-[2-(diethylamino)ethyl]-N-(1-methylethyl)urea tartrate[1:1]

The title compound was prepared by Method A and the procedure of Example 1, reacting in sequence:

0.060 mole phosgene, Proton Sponge ®, 10.44 g (0.04 mole) of N-[2-[(4-chlorophenyl)sulfonyl]ethyl]-1-methylethanamine (oil in Preparation 5), 9.28 g (0.08 mole) unsym-diethylethylenediamine to give an oil, the free base of the title compound which was then reacted with tartaric acid (55.8%), m.p. 135°–137° C.

Analysis: Calculated for $C_{22}H_{36}N_3O_9SCl$: C, 47.69; H, 6.65; N, 7.58. Found: C, 47.75; H, 6.61; N, 7.58.

EXAMPLE 5

N-[2-[(4-Chlorophenyl)sulfonyl]ethyl]-N'-[2-(dimethylamino)ethyl]-N'-(1-methylethyl)urea maleate[1:1]

The title compound was prepared by Method A and the procedure of Example 1, reacting in sequence:

0.1014 mole phosgene, Proton Sponge ®, 9.97 g (0.0455 mole) of 2-[(4-chlorophenyl)sulfonyl]ethanamine (oil in Preparation 8), 5.05 g (0.05 mole) triethylamine, 5.92 g (0.046 mole) of N-isopropyl-N',N'-dimethylenediamine to give an oil which crystallized to a brown solid, the free base of the title compound which was then reacted with maleic acid (41.2%), m.p. 125°–126° C.

Analysis: Calculated for $C_{20}H_{30}N_3O_7SCl$: C, 48.83; H, 6.15; N, 8.54. Found: C, 48.64; H 6.16; N, 8.58.

EXAMPLE 6

N-[2-[(4-Chlorophenyl)sulfonyl]ethyl]-N'-[2-(dimethylamino)ethyl]-N-(1-methylethyl)thiourea, hemifumarate The title compound was prepared by Method A and the procedure of Example 1 with modification as indicated, reacting in sequence:

4.90 g (0.043 mole) thiophosgene, Proton Sponge ®, 7.83 g (0.03 mole) of N-[2-[(4-chlorophenyl)sulfonyl]ethyl]-1-methylethanamine (oil in Preparation 5), 5.28 g (0.06 mole) unsym-N,N-dimethylethylenediamine, to give an oil which was subjected to column chromatography on a silica-gel column, eluting with 5–95 (methanol-chloroform). The pure fractions were combined, solvent removed and an oil, the free base of the title compound, obtained which was reacted with fumaric acid (16.6%), m.p. 141°–142° C.

Analysis: Calculated for $C_{18}H_{28}N_3O_4S_2Cl$: C, 48.04; H, 6.27; N, 9.34. Found: C, 47.74; H, 6.21; N, 9.35.

EXAMPLE 7

N-[2-[(4-Chlorophenyl)sulfinyl]ethyl]-N'-[2-(dimethylamino)ethyl]-N-(1-methylethyl)urea, fumarate[1:1]

(Demonstration of Method B)

To a solution of 4.70 g (0.029 mole) of 1,1'-carbonyldiimidazole and 2.38 g (0.027 mole) of N,N-dimethylaminoethylamine in tetrahydrofuran which had stirred at room temperature for 50 min was added a solution of 6.14 g (0.0251 mole)of N-[2-[(4-chlorophenyl)sulfinyl]ethyl]-1-methylethanamine in tetrahydrofuran. The solution was refluxed for about 10 hr and the solvent removed in vacuo to give an oil residue. The oil was dissolved in methylene chloride and washed by extraction several times with water. The methylene chloride solution was dried over magnesium sulfate and evaporated in vacuo to give an oil, and the free base of the title compound. A solution of the oil in methanol was reacted with fumaric acid and the salt precipitated by addition of diethyl ether as white crystalline solid (58.6%), m.p. 112.5°–114.5° C.

Analysis: Calculated for $C_{20}H_{30}N_3O_6SCl$: C, 50.47; H, 6.35; N, 8.83. Found: C, 50.45; H, 6.38; N, 8.86.

EXAMPLE 8

N'-[2-(Dimethylamino)ethyl]-N-(1-methylethyl)-N-[2-(phenylsulfonyl)ethyl]urea, maleate[1:1]

The title compound was prepared by Method B and the procedure of Example 7, reacting in sequence:
5.67 g (0.035 mole) of 1,1-carbonyldiimidazole,
2.91 g (0.033 mole) of N,N-dimethylaminoethylamine,
6.00 g (0.026 mole) of 1-methyl-N-[2-(phenylsulfonyl)ethyl]ethanamine (oil in Preparation 6) to give an oil, the free base of the title compound which was then reacted with maleic acid (39.2%), m.p. 103°–105° C.

Analysis: Calculated for $C_{20}H_{31}N_3O_7S$: C, 52.50; H, 6.83; N, 9.18. Found: C, 52.48; H, 6.90; N, 9.18.

EXAMPLE 9

N'-[2-(Diethylamino)ethyl]-N-(1-methylethyl)-N-[2-(phenylsulfonyl)ethyl]urea maleate[1:1]

The title compound was prepared by Method B and the procedure of Example 7, reacting in sequence:
9.72 g (0.060 mole) of 1,1'-carbonyldiimidazole,
5.19 g (0.045 mole) of N,N-diethylaminoethylamine, and
10.33 g (0.046 mole) of 1-methyl-N-[2-(phenylsulfonyl)ethyl]ethanamine (oil in Preparation 6) to give an oil, the free base of the title compound which was then reacted with maleic acid, m.p. 88°–90° C.

Analysis: Calculated for $C_{22}H_{35}N_3O_7S$: C, 54.42; H, 7.27; N, 8.65. Found: C, 54.33; H, 7.30; N, 8.63.

EXAMPLE 10

N'-[2-(Dimethylamino)ethyl]-N-(1-methylethyl)-N-[2-[(1-naphthalenesulfonyl)ethyl]urea, maleate[1:1]

To a solution of 35 ml of 12.5% phosgene in benzene (0.0665 mole) and 9.0 g Proton Sponge ® [1,3-bis-(dimethylamino)naphthalene] (0.02 mole) in 200 ml of methylene chloride was added a solution of 4.60 g (0.0166 mole) of 1-methyl-N-[2-[(1-naphthalenyl)sulfonyl]ethyl]ethanamine obtained as brown oil in Preparation 12) in 100 ml methylene chloride over a 20 minute period. The reaction mixture was stirred for one hr at room temperature and then extracted with 1N sulfuric acid. The methylene chloride layer was separated, dried over potassium carbonate, filtered and evaporated. The yellow crystalline solid obtained was dissolved in 350 ml of tetrahydrofuran. To this solution was added 3.52 g (0.04 mole) of unsym-dimethylethylenediamine and the mixture was stirred overnight at room temperature. The reaction mixture was stripped to dryness and the residue partitioned between chloroform and water. Evaporation of the chloroform layer gave a dark brown oil, the free base of the title compound which was reacted with maleic acid. The maleate salt was recrystallized from methanol-diethyl ether to give 5.51 g (65.4%) of yellow solid, m.p. 126°–128° C.

Analysis: Calculated for $C_{24}H_{33}N_3O_7S$: C, 56.79; H, 6.55; N, 8.28. Found: C, 56.60; H, 6.61; N, 8.26.

EXAMPLE 11

N'-[2-(Diethylamino)ethyl]-N-(1-methylethyl)-N-[2-(2,3-dihydro-1H-inden-4-yl-sulfonyl)ethyl]urea, maleate The title compound is prepared by Method B, reacting in sequence:
1,1'-carbonyldiimidazole,
unsym-N,N-diethylethylendiamine, and
1-methyl-N-[2-(2,3-dihydro-1H-inden-4-yl-sulfonyl)-]ethanamine, to give the free base of the title compound which is then reacted with maleic acid.

EXAMPLE 12

N'-[2-(Diethylamino)ethyl]-N-(1-methylethyl)-N-[2-(2,3-dihydro-1H-inden-5-yl-sulfonyl)ethyl]urea, maleate The title compound is prepared by Method B, reacting in sequence:
1,1'-carbonyldiimidazole,
unsym-N,N-diethylethylenediamine and
1-methyl-N-[2-(2,3-dihydro-1H-inden-5-yl-sulfonyl)-]ethaneamine, to give the free base of the title compound which is then reacted with maleic acid.

EXAMPLE 13

N'-[2-(Diethylamino)ethyl]-N-(1-methylethyl)-N-[2-[(4-methylphenyl)sulfonyl]ethyl]urea maleate The title compound is prepared by Method B, reacting in sequence:
1,1'-carbonyldiimidazole,
unsym-N,N-diethylethylenediamine, and
N-[2-[(4-methylphenyl)sulfonyl]ethyl]-1-methylethanamine, to give the free base of the title compound which is then reacted with maleic acid.

EXAMPLE 14

N'-[2-(Diethylamino)ethyl]-N-(1-methylethyl)-N-[2-[(4-methoxyphenyl)sulfonyl]ethyl]urea, maleate The title compound is prepared by Method B, reacting in sequence:
1,1'-carbonyldiimidazole,
unsym-N,N-diethylethylenediamine, and
N-[2-[(4-methoxyphenyl)sulfonylethyl]-1-methylethanamine, to give the free base of the title compound which is then reacted with maleic acid.

EXAMPLE 15

N-[2-[(3,5-Dichlorophenyl)sulfonyl]ethyl]-N'-[2-(diethylamino)ethyl]-N-(1-methylethyl)urea, maleate The title compound is prepared by Method B, reacting in sequence:
1,1'-carbonyldiimidazole,
unsym-N,N-diethylethylenediamine, and
N-[2-[(3,5-dichlorophenyl)sulfonyl]ethyl]-1-methylethanamine, to give the free base of the title compound which is then reacted with maleic acid.

EXAMPLE 16

N'-[2-(Diethylamino)ethyl]-N-[2-[3,4,5-trimethoxyphenyl)sulfonyl]ethyl]-N-(1-methylethyl)urea, maleate The title compound is prepared by Method B, reacting in sequence:
1,1'-carbonyldiimidazole,
unsym-N,N-diethylethylenediamine, and
N-[2-[(3,4,5-trimethoxyphenyl)sulfonyl]ethyl]-1-methylethanamine, to give the title compound which is then reacted with maleic acid.

EXAMPLE 17

N'-[2-(Dimethylamino)ethyl]-N-[2-[(4-fluorophenyl)-sulfonyl]ethyl]-N-(1-methylethyl)urea, maleate The title compound is prepared by Method B, reacting in sequence:
1,1'-carbonyldiimidazole,
unsym-N,N-dimethylethylenediamine, and
N-[2-[(4-fluorophenyl)sulfonyl]ethyl]-1-methylethanamine, to give the free base of the title compound which is then reacted with maleic acid.

EXAMPLE 18

N'-[2-(Diethylamino)ethyl]-N-(1-methylethyl)-N-[2-[(4-trifluoromethylpheny)sulfonyl]ethyl]urea, maleate The title compound is prepared by Method B, reacting in sequence:
1,1'-carbonyldiimidazole,
unsym-N,N-diethylethylenediamine, and
1-methyl-N-[2-[(4-trifluoromethylphenyl)sulfonyl]ethyl]ethanamine, to give the free base of the title compound which is then reacted with maleic acid.

EXAMPLE 19

N-[2-[(4-Cyanophenyl)sulfonyl]ethyl]-N'-[2-(diethylamino)ethyl]-N-(1-methylethyl)urea, maleate The title compound is prepared by Method B, reacting in sequence:
1,1'-carbonyldiimidazole,
unsym-N,N-diethylethylenediamine, and
N-[2-[(4-cyanophenyl)sulfonyl]ethyl]ethanamine, to give the free base of the title compound which is then reacted with maleic acid.

EXAMPLE 20

N-[3-[(4-Chlorophenyl)sulfonyl]propyl]-N'-[2-(diethylamino)ethyl]-N'-(1-methylethyl)urea, maleate The title compound is prepared by Method C, reacting in sequence:
1,1'-carbonyldiimidazole,
3-[(4-chlorophenyl)sulfonyl]propanamine (free base in Preparation 10 prepared by neutralization), and
N-isopropyl-N',N'-diethylethylenediamine, to give the free base of the title compound which is then reacted with maleic acid.

EXAMPLE 21

N'-[2-(Diethylamino)ethyl]-N-(1-methylethyl)-N-[3-(phenylsulfonyl)propyl]urea, maleate The title compound is prepared by Method C, reacting in sequence:
1,1'-carbonyldiimidazole,
3-(phenylsulfonyl)propanamine, and
N-isopropyl-N',N'-diethylethylenediamine, to give the free base of the title compound which is then reacted with maleic acid.

EXAMPLE 22

N'-[3-(Dimethylamino)propyl]-N-(1-methylethyl)-N-[2-(phenylsulfonyl)ethyl]urea, maleate The title compound is prepared by Method B, reacting in sequence:
1,1'-carbonyldiimidazole,
unsym-N,N-dimethylpropylenediamine, and
1-methyl-N-[2-(phenylsulfonyl)ethyl]ethanamine (oil in preparation 6), to give the free base of the title compound which is then reacted with maleic acid.

EXAMPLE 23

N-(1-Methylethyl)-N-[2-(phenylsulfonyl)ethyl]-N'-[2-(1-pyrrolidinyl)ethyl]urea maleate[1:1]

The title compound was prepared by Method B, reacting in sequence 3.65 g (0.032 mole) of N-(2-aminoethyl)pyrrolidine, 5.67 g (0.035 mole) of 1,1'-carbonyldiimidazole and 6.51 g (0.0287 mole) of 1 methyl-N-[2-(phenylsulfonyl)ethyl]ethanamine (oil in Preparation 6) to give the free base of the title compound which was then reacted with maleic acid. The maleate salt was recrystallized from methanol-diethyl ether to give 11.75 g (84.7%) of white crystalline solid, m.p. 131°–132° C.

Analysis: Calculated for $C_{22}H_{33}N_3O_7S$: C, 54.64; H, 6.88; N, 8.69. Found: C, 54.30; H, 6.83; N, 8.70.

EXAMPLE 24

Following the procedure of Example 23 and substituting N-(2-aminoethyl)-4-methylpiperazin-1-yl for N-(2-aminoethyl)pyrrolidine, there is obtained N-(1-methylethyl)-N-[2-(phenylsulfonyl)ethyl]-N'-[2-(4-methylpiperazin-1-yl)ethyl urea, oxalate.

EXAMPLE 25

N-Cyclohexyl-N'-[2-(diethylamino)ethyl]-N-[2-phenylsulfonyl)ethyl]urea, maleate

The title compound is prepared by Method B and the procedure of Example 7 by reacting in sequence:
1,1'-carbonyldiimidazole,
N,N-diethylaminoethylamine, and
N-cyclohexyl-N-[2-(phenylsulfonyl)ethyl]amine, to give the free base of the title compound which is then reacted with maleic acid.

EXAMPLE 26

N'-[2-(Diethylamino)ethyl]-N-phenyl-N-[2-(phenylsulfonyl)ethyl]urea, maleate

The title compound is prepared by Method B and the procedure of Example 7 by reacting in sequence:
1,1'-carbonyldiimidazole,
N,N-diethylaminoethylamine, and N-phenyl-N-[2-(phenylsulfonyl)ethyl]amine, to give the free base of the title compound which is then reacted with maleic acid.

EXAMPLE 27

N-Benzyl-N'-[2-(diethylamino)ethyl]-N-[2-(phenylsulfonyl)ethyl]urea, maleate

The title compound is prepared by Method B and the procedure of Example 8 by reacting in sequence:
1,1'-carbonyldiimidazole,
N,N-diethylaminoethylamine, and
N-benzyl-N-[2-(phenylsulfonyl)ethyl]amine, to give the free base of the title compound which is then reacted with maleic acid.

EXAMPLE 28

N'-(2-Aminoethyl)-N-(1-methylethyl)-N-[2-(phenylsulfonyl ethyl]urea, maleate[1:1]

To a solution of 131.9 g of a 12% solution of phosgene in benzene (15.83 g, 0.160 mole) in 400 ml of methylene chloride was added a mixture of 30.91 g (0.136 mole) of the free base of 1-methyl-N-[2-(phenylsulfonyl)ethyl ethanamine and 20 g (0.198 mole) of triethylamine in 100 ml of methylene chloride. The solution was cooled in an ice bath during the addition. The solution was stirred at room temperature for 3 hr. The reaction solution was extracted with dilute sulfuric acid and then was dried over magnesium sulfate. The solvent was removed in vacuo to give an oil. The oil was suspended in 200 ml of anhydrous ether, and the ether was removed in vacuo. A solution of the resulting oil in 200 ml of acetonitrile was added to a mixture of 300 g (5 mole) of ethylenediamine and 200 ml of acetonitrile. The mixture was stirred at room temperature for 3 hr, and the solvent was removed in vacuo. The resulting residue was partitioned between methylene chloride and dilute sodium hydroxide. The methylene chloride solution was dried over magnesium sulfate and the solvent was removed in vacuo to give the free base of the title compound as an oil. This was converted to the maleate salt, and the salt was recrystallized from methanol-diethyl ether to give 37.82 g (64.7%) of white crystalline solid, m.p. 169°–170° C.

Analysis: Calculated for $C_{18}H_{27}N_3O_7S$: C, 50.34; H, 6.34; N, 9.78. Found: C, 49.95; H, 6.38; N, 9.71.

EXAMPLE 29

N'-[2-(Methylamino)ethyl]-N'-methyl-N-(1-methylethyl)-N-[2-phenylsulfonyl)ethyl]urea, maleate The title compound is prepared by Method A by reacting in sequence:
phosgene,
Proton Sponge ®,
1-methyl-N-[2-phenylsulfonyl)ethyl]ethanamine (oil in Preparation 6), and
sym-N,N-dimethylethylenediamine, to give the free base of the title compound which is then reacted with maleic acid.

EXAMPLE 30

N'-[2-(Diethylamino)ethyl]-N-(1-methylethyl)-N-[2-phenylsulfonyl)ethyl]thiourea, fumarate The title compound is prepared following the procedure of Example 6, reacting in sequence:
thiophosgene, Proton Sponge ®,
1-methyl-N-[2-(phenylsulfonyl)ethyl]ethanamine (oil in preparation 6), and
unsym.-N,N-diethylethylenediamine, to give the free base of the title compound which is reacted with fumaric acid.

EXAMPLE 31

N'-[2-(Dimethylamino)ethyl]-N-(1-methylethyl)-N-[2-[(4-methylphenyl)sulfonyl]ethyl]urea, maleate The title compound is prepared by Method A and the procedure of Example 1 by reacting in sequence:
phosgene, Proton Sponge ®,
1-methyl-N-[2-[(4-methylphenyl)sulfonyl]ethyl]ethanamine (oil obtained in preparation 14),
unsym-N,N-dimethylethylenediimine, to give an oil, the free base of the title compound which is then reacted with maleic acid.

EXAMPLE 32 (Method C)

N-[2-[(4-Chlorophenyl)sulfonyl]ethyl]-N'-[2-(dimethylamino)ethyl]-N'-(1-methylethyl)urea maleate A tetrahydrofuran solution of equal molar amounts of 1,1'-carbonyldiimidazole and 3-[(4-chlorophenyl)sulfonyl]ethanamine (free base in preparation 10) is stirred at room temperature for several hours. N-Isopropyl-N',N'-dimethylenediamine in 50% molar excess is added and the mixture is heated with stirring under reflux for several hours. The tetrahydrofuran is removed and the resultant oil partitioned between chloroform and water. The free base is isolated by evaporation of the chloroform layer and thereafter reacted with maleic acid.

EXAMPLE 33 (Method D)

N-[3-[(4-Chlorophenyl)sulfonyl]propyl]-N'-(1-methylethyl)-N'-[2-(dimethylamino)ethyl]urea, maleate To a solution of phosgene in methylene chloride is added an equimolar amount of N'-isopropyl-N,N-dimethylethylenediamine also in methylene chloride over a 30 minute period. The solution is stirred for one hour at room temperature. To the reaction mixture was added dropwise with stirring a molar equivalent amount of 3-[(4-chlorophenyl)sulfonyl]propanamine (free base in preparation 10) and a double molar portion of triethylamine over a 30 min. period. The reaction mixture is stirred overnight at room temperature and thereafter extracted with aqueous 10% sodium hydroxide solution. The methylene chloride layer is extracted with 1N sulfuric acid. The acid layer was made alkaline and extracted with chloroform. The chloroform layer is evaporated to give the free base of the title compound. The free base is converted to the maleate salt by reaction with maleic acid and recrystallized by use of conventional solvents.

EXAMPLE 34

N'-[2-(Dimethylamino)ethyl]-N-(1-methylethyl)-N-[2-[(1-naphthaleneylthio)]ethyl]urea, maleate The title compound is prepared by Method A and the procedure of Example 10, reacting in sequence:
phosgene,
Proton Sponge ®,
1-methyl-N-[2-(1-naphthalenylthio)ethyl]ethanamine (free base in preparation 11), unsym-dimethylethylenediamine, to give the free base of the title compound which is then reacted with maleic acid.

EXAMPLE 35

N'-[2-(Dimethylamino)ethyl]-N-(1-methylethyl)-N-[2-[(1-naphthalenesulfinyl)]ethyl]urea maleate The title compound is prepared by Method B and the procedure of Example 7, reacting in sequence:
1,1'-carbonyldiimidazole,
unsym-dimethylethylenediamine, and
1-methyl-N-[2-(1-naphthalenesulfinyl)ethyl]ethanamine (free base in Preparation 18) to give the free base of the title compound which is then reacted with maleic acid.

EXAMPLE 36

N'-[2-(Dimethylamino)ethyl]-N-(1-methylethyl)-N-[2-[(4-nitrophenylsulfonyl)ethyl]urea, maleate The title compound is prepared by Method B, reacting in sequence:
1,1'-carbonyldiimidazole,
unsym-N,N-dimethylethylenediamine, and
N-[2-[(4-nitrophenyl)sulfonyl]ethyl]-1-methylethanamine from Preparation 16, to give the free base of the title compound which is then reacted with maleic acid.

EXAMPLE 37

N'-[2-(Dimethylamino)ethyl]-N-(1-methylethyl)-N-[2-(1-naphthalenylthio)ethyl]urea, oxalate[1:1]

To a solution of 7.0 g (0.0327 mole) of Proton Sponge ® and phosgene (80 ml benzene solution of 12.5% phosgene) in 400 ml of methylene chloride was added a methylene chloride solution of 8.03 g (0.0327 mole) of 1-methyl-N-[2-(1-naphthalenylthio)ethyl]ethanamine (oil in Preparation 11). The resulting solution was stirred for 2½ hr at room temperature, then extracted with 1N sulfuric acid solution. The methylene chloride layer was dried over anhydrous potassium carbonate, filtered and evaporated to dryness. The residue oil was dissolved in 400 ml of tetrahydrofuran. To the solution was added 5.75 g (0.065 mole) of unsym-dimethylethylenediamine. Tetrahydrofuran was evaporated to leave an oil, the free base of the title compound, which was reacted with oxalic acid. The oxalate salt was recrystallized from methanol-diethyl ether to give 8.86 g (60.3%) yield of white crystals, m.p. 101.5°–104° C.

Analysis: Calculated for $C_{22}H_{31}N_3O_5S$: C, 58.78; H, 6.95; N, 9.35. Found: C, 58.52; H, 6.93; N, 9.32.

EXAMPLE 38

N'-[2-(Diethylamino)ethyl]-N-(1-methylethyl)-N-[2-[(4-methylphenyl)sulfonyl]ethyl]urea, tartrate[1:1]

To a solution of phosgene (35 ml of 12.5% in benzene) and 4.28 g (0.02 mole) Proton Sponge ® in 300 ml of methylene chloride was added a methylene chloride solution of 6.64 g (0.0195 mole) 1-methyl-N-[2-[(4-methylphenyl)sulfonyl]ethyl]ethanamine (oil in Preparation 14) over a 45 minute period. The resulting solution was stirred 2 hr at room temperature and extracted with 1N sulfuric acid. The methylene chloride solution was dried over anhydrous potassium carbonate and filtered. The filtrate was evaporated to give an oil which was dissolved in 300 ml of tetrahydrofuran. To the solution was added 4.64 g (0.04 mole) of N,N-diethylethylenediamine. After stirring for about 50 hr, the tetrahydrofuran was removed in a rotary evaporator to give an oil. The oil was partitioned between chloroform and water. Removal of chloroform gave an oil, the free base of the title compound. The last oil was reacted with tartaric acid and the tartrate salt recrystallized from methanol-diethyl ether to give 6.14 g (59.1%) of yellow solid, m.p. 122°–125° C.

Analysis: Calculated for $C_{23}H_{39}N_3O_9S$: C, 51.77; H, 7.37; N, 7.87. Found: C, 51.44; H, 7.35; N, 7.79.

EXAMPLE 39

N-[2-[(3,4-Dichlorophenyl)sulfonyl]ethyl]-N'-(dimethylamino)ethyl]-N-(1-methylethyl)urea maleate[1:1]

To a solution of 6.00 g (0.037 mole) of 1,1'-carbonyldiimidazole and 2.90 g (0.033 mole) of unsym-N,N-dimethylethylenediamine in 300 ml of tetrahydrofuran which had stirred for 2 hr at room temperature was added a solution of 7.96 g (0.027 mole) of N-[2-[(3,4-dichlorophenyl)sulfonyl]ethyl]ethanamine in 100 ml of tetrahydrofuran. The solution was heated overnight at reflux. The solvent was removed using a rotary evaporator to give an oil residue which was dissolved in chloroform. The solution was extracted with water. Evaporation of chloroform gave an oil, the free base of the title compound which was reacted with maleic acid and the resulting salt was recrystallized from methanol-diethyl ether to give 10.12 g (71.4%) white crystalline product, m.p. 145°–146° C.

Analysis: Calculated for $C_{20}H_{29}N_3O_7SCl_2$: C, 45.63; H, 5.55; N, 7.98. Found: C, 45.63; H, 5.61; N, 8.11.

EXAMPLE 40

N'-[2-(Diethylamino)ethyl]-N-(1-methylethyl)-N-[2-[(4-methylphenyl)sulfinyl]ethyl]urea hemihydrate To a solution of 9.08 g (0.056 mole) of 1,1'-carbonyldiimidazole and 5.58 g (0.048 mole) of unsym-N,N-diethylethylenediamine in tetrahydrofuran which had stirred for 2 hr at room temperature was added a solution of 9.43 g (0.419 mole) of 1-methyl-N-[2-[(4-methylphenyl)sulfinyl]ethyl]ethanamine (oil in Preparation 19) in tetrahydrofuran. The solution was heated overnight at gentle reflux. The reaction mixture was stripped to dryness and the resulting oil residue was partitioned between chloroform and water. Evaporation of the chloroform layers gave an oil which was chromatographed by slurring with methanol-chloroform (20–80 vol %) and silica gel with repeated filtration. Filtrates were combined and solvent removed by evaporation. The residue was dried in vacuo overnight to give 6.98 g (44.2%) light-brown oil.

Analysis: Calculated for $C_{38}H_{68}N_6O_5S_2$: C, 60.60; H, 9.10; N, 11.16. Found: C, 60.95; H, 9.12; N, 11.35.

EXAMPLE 41

N'-[3-(Diethylamino)propyl]-N-(1-methylethyl)-N-[3-(phenylsulfonyl)propyl]urea oxalate[1:1]hemihydrate To a solution of 6.17 g (0.038 mole) of 1,1'-carbonyldiimidazole and 4.28 g (0.033 mole) of unsym-N,N-diethyl-1,3-propanediamine in 300 ml of tetrahydrofuran which had stirred for 2 hours at room temperature was added a solution of 7.23 g (0.03 mole) of 1-methyl-N-[3-(phenylsulfonyl)propyl]ethanamine (oil in Preparation 26) in 100 ml of tetrahydrofuran. The resulting solution was heated overnight at reflux. The reaction mixture was stripped to dryness and the residue partitioned between chloroform and water. The chloroform layer was evaporated to give an oil, the free base of the title compound. The oil was reacted with oxalic acid and the resulting salt was recrystallized from methanol-diethyl ether to give 12.31 g (82.6%) of white crystalline product, m.p. 120°–121.5° C.

Analysis: Calculated for $C_{44}H_{76}N_6O_{15}S_2$: C, 53.21; H, 7.71; N, 8.46; Found: C, 53.36; H, 7.62; N, 8.96.

EXAMPLE 42

N'-[2-(Diethylamino)ethyl]-N-(1-methylethyl)-N-[3-(phenylsulfonyl)propyl]urea oxalate[1:1]hemihydrate To a solution of 9.73 g (0.06 mole) of 1,1'-carbonyldiimidazole and 6.06 g (0.054 mole) of unsym N,N-diethylethylenediamine in 350 ml of tetrahydrofuran which had stirred for 1.5 hr at room temperature was added a solution of 12.06 g (0.05 mole) of 1-methyl-N-[3-(phenylsulfonyl)propyl]ethanamine (oil in Preparation 26) in 100 ml of tetrahydrofuran. The resulting solution was heated overnight at gentle reflux. The reaction mixture was stripped to dryness and the residue partitioned between chloroform and water. The chloroform layer was evaporated to give an oil, the free base of the title compound which was reacted with oxalic acid and the resulting salt was recrystallized from methanol-diethyl ether to give 20.46 g (84.8%) of white crystalline product, m.p. 117°–118.5 C.

Analysis: Calculated for $C_{42}H_{72}N_6O_{15}S_2$: C, 52.27; H, 7.52; N, 8.71. Found: C, 52.62; H, 7.35; N, 8.61.

EXAMPLE 43

N'-[3-(Diethylamino)propyl]-N-(1-methylethyl)-N-[2-(phenylsulfonyl)ethyl]urea.¼ hydrate To a solution of 6.00 g (0.037 mole) of 1,1'-carbonyldiimidazole and 4.17 g (0.032 mole) unsym-N,N-diethylethylenediamine in 300 ml of tetrahydrofuran which had stirred at room temperature for 2.5 hr was added a solution of 6.81 g (0.03 mole) of 1-methyl-N-[2-(phenylsulfonyl)ethyl]ethanamine (oil in Preparation 6) in 100 ml of tetrahydrofuran. The solution was heated overnight at reflux. The reaction mixture was stripped to dryness and the resulting oil residue was partitioned between chloroform and water. Evaporation of the chloroform layer gave an oil which was chromatographed by slurrying with 95 to 98 vol % chloroform-2 to 5 vol % acetone and 50–90 vol % chloroform and 10–50 vol % methanol and silica gel with repeated filtration. Filtrates were combined and solvent removed by evaporation. The residual oil was triturated with diethyl ether. The light brown oil remaining after decanting the ether and drying in vacuo overnight at 90° C. weighed 5.29 g (44.9%).

Analysis: Calculated for $C_{38}H_{64}N_6O_7$: C, 58.13; H, 8.78; N, 10.70. Found: C, 58.31; H, 8.64; N, 10.80.

EXAMPLE 44

N'-[2-(Diethylamino)ethyl]-N-[2-[(4-fluorophenyl)sulfonyl]ethyl]-N-(1-methylethyl)urea To a solution of 6.49 g (0.04 mole) of 1,1-carbonyldiimidazole and 4.06 g (0.035 mole) of unsym-N,N-diethylethylenediamine in 400 ml of tetrahydrofuran which had stirred at room temperature for 1.5 hr was added 8.45 g (0.03 mole) of N-[2-[(4-fluorophenyl)sulfonyl]ethyl]-1-methylethanamine. The solution was heated overnight at reflux. The reaction mixture was stripped to dryness and partitioned 5 times between water and methylene chloride. The methylene chloride layers were combined and evaporated to dryness. The oil was partitioned between diethyl ether and water several times. The ether layers were combined and solvent was removed by evaporation. After drying in vacuo at 80° C. for 36 hr, 4.56 g (39.2%) of brown oil was obtained.

Analysis: Calculated for $C_{18}H_{30}N_3O_3SF$: C, 55.79; H, 7.80; N, 10.87. Found: C, 55.31; H, 7.80; N, 10.48.

EXAMPLE 45

N-[2-(Diethylamino)ethyl]-N-methyl-N'-(1-methylethyl-N'-[2-(phenylsulfonyl)ethyl]urea maleate The title compound is prepared by Method A and the procedure of Example 1 by reacting in sequence:
phosgene, Proton Sponge®
N-[2-(phenylsulfonyl)ethyl]-2-propanamine, and
N,N-diethyl-N'-methylethylenediamine to give the free base of the title compound which is then reacted with maleic acid.

EXAMPLE 46

N-(1-Methylethyl)-N'-[2-[bis(1-methylethyl)amino]ethyl]-N-[2-(phenylsulfonyl)ethyl]urea A solution of unsym-N,N-diisopropyl-ethylenediamine (6.60 g, 0.0458 mole) and 1,1'-carbonyldiimidazole (8.60 g, 0.053 mole) in tetrahydrofuran was stirred two hours at room temperature. To the mixture, 11.35 g (0.05 mole) of 1-methyl-N-[2-(phenylsulfonyl)ethyl]ethanamine in tetrahydrofuran was added and the resulting solution was heated eighteen hours at reflux. The reaction was stripped to dryness and the residue dissolved in diethyl ether. The ether was extracted several times with water followed by 1N sulfuric acid. The acidic layer was made alkaline and then extracted with chloroform. Removal of chloroform gave a dark brown oil. The oil, 19.9 g, was chromatographed on 525 g of Florisil using methanolmethylene chloride as eluant. This chromatography furnished 2.93 g (16.1%) of brown oil which was dried in vacuo at 80° C. overnight. Decomposition during chromatography seemed evident, explaining the low yield.

Analysis: Calculated for $C_{20}H_{35}N_3O_3S$: C, 60.42; H, 8.87; N, 10.57. Found: C, 60.22; H, 8.97; N, 10.54.

EXAMPLE 47

N-(1-Methylethyl)-N'-[2-[methyl-(2-phenylethyl)amino]ethyl]-N-[2-(phenylsulfonyl)ethyl]urea hemihydrate A solution of 1,1'-carbonyldiimidazole (8.12 g, 0.05 mole) and N-methyl-N-(2-phenylethyl)-1,2-ethanediamine, 8.0 g (0.0045 mole) in 300 ml of tetrahydrofuran was stirred for 2 hours at room temperature. To the mixture was added 9.37 g (0.0412 mole) of 1-methyl-N-[2-(phenylsulfonyl)ethyl]ethanamine and the reaction was heated at gentle reflux overnight. The reaction was stripped to dryness and dissolved in chloroform-diethyl ether (50-50 v/v) and extracted with water. The organic phase was extracted with 1N sulfuric acid. (Approximately half the product was extracted with acid and half remained in the organic layer). The organic layer was extracted with dilute sodium hydroxide, dried, filtered, and the solvent removed to give an oil. The oil was subjected to column chromatography on Silica Gel using acetone-ethyl acetate as a eluant. This furnished 0.5 g (2.8%) of oil.

Analysis: Calculated for $C_{23}H_{34}N_3O_{3.5}$: C, 62.70; H, 7.78; N, 9.54. Found: C, 62.53; H, 7.65; N, 9.54.

EXAMPLE 48

N-(1-Methylethyl)-N'-[2-[methyl(phenylmethyl)amino]ethyl]-N-[2-(phenylsulfonyl)ethyl]urea A solution of 17.90 g (0.045 mole) of N-methyl-N-(phenylmethyl)-1,2-ethanediamine and 1,1'-carbonyldiimidazole (0.05 mole) in 100 ml of tetrahydrofuran was stirred at room temperature for 1 hour. To the mixture was added 10.52 g, (0.04 mole) of 1-methyl-N-[2-(phenylsulfonyl)ethyl]ethanamine and the resulting solution heated overnight at gentle reflux. The reaction mixture was stripped to dryness and partitioned between chloroform and water; removal of chloroform gave a dark brown oil. The oil was dissolved in chloroform and extracted with 1N sulfuric acid (saturated with sodium chloride). The acidic layer was made alkaline, extracted with chloroform, and the solvent removed to give a light brown oil. The oil was subjected to chromatography on a Florisil column and eluted with methanol-methylene chloride. After combining appropriate fractions from the column and removing solvent, an oil was obtained. The oil was triturated with diethyl ether and dried at 80° C. in vacuo overnight. This furnished 6.75 g (40.4%) of clear oil.

Analysis: Calculated for $C_{22}H_{31}N_3O_3S$: C, 63.28; H, 7.48; N, 10.06. Found: C, 62.74; H, 7.55; N, 10.10.

EXAMPLE 49

N-[2-[(4-Bromophenyl)sulfonyl]ethyl]-N'-[2-(diethylamino)ethyl]-N-(1-methylethyl)urea maleate The title compound is prepared by Method B, reacting in sequence:
1,1-carbonyldiimidazole,
unsym-N,N-diethylenediamine, and
N-[2-[(4-bromophenyl)sulfonyl]ethyl]-2-propanamine, to give the free base of the title compound which is then reacted with maleic acid.

EXAMPLE 50

N'-[2-(Diethylamino)ethyl]-N-[2-[[4-(1,1-dimethylethyl)phenyl]sulfonyl]ethyl]-N-(1-methylethyl)urea maleate The title compound is prepared by Method B, reacting in sequence:
1,1'-carbonyldiimidazole,
unsym-N,N-diethylethylenediamine, and
N-[2-[(4-t-butylphenyl)sulfonyl]ethyl]-2-propanamine, to give the free base of the title compound which is then reacted with maleic acid.

EXAMPLE 51

N-[2-(Diethylamino)ethyl]-N'-methyl-N-(1-methylethyl)-N'-[2-(phenylsulfonyl)ethyl]urea maleate The title compound is prepared by Method A and the procedure of Example 1 by reacting in sequence:
phosgene, Proton Sponge ®,
N-methyl-2-(phenylsulfonyl)ethanamine, and
N,N-diethyl-N'-isopropylethylenediamine, to give the free base of the title compound which is then reacted with maleic acid.

EXAMPLE 52

N'-[2-(Diethylamino)ethyl]-N-[2-[(2-furanylmethyl)thio]ethyl]-N-(1-methylethyl)urea maleate The title compound is prepared by Method B, reacting in sequence:
1,1'-carbonyldiimidazole,
unsym-N,N-diethylethylenediamine, and
N-[2-[(2-furanylmethyl)thio]ethyl]-2-propanamine, to give the free base of the title compound which is then reacted with maleic acid.

EXAMPLE 53

N'-[2-(Diethylamino)ethyl]-N-[2-[(2-furanylmethyl)sulfonyl]ethyl]-N-(1-methylethyl)urea The title compound is prepared by Method B, reacting in sequence:
1,1'-carbonyldiimidazole,
unsym-N,N-diethylethylenediamine, and
N-[2-[(2-furanylmethyl)sulfonyl]ethyl]-2-propanamine, to give the gree base of the title compound which is then reacted with maleic acid.

EXAMPLE 54

N'-[2-(Diethylamino)ethyl]-N-[2-[(2-furanylmethyl)sulfinyl]ethyl]-N-(1-methylethyl)urea maleate The title compound is prepared by Method B, reacting in sequence:
1,1'-carbonyldiimidazole,
unsym-N,N-diethylethylenediamine, and
N-[2-[(2-furanylmethyl)sulfinyl]ethyl]-2-propanamine, to give the free base of the title compound which is then reacted with maleic acid.

EXAMPLE 55

N'-[2-(Diethylamino)ethyl]-N-(1-methylethyl)-N-[2-[(phenylmethyl)sulfonyl]ethyl]urea maleate The title compound is prepared by Method B, reacting in sequence:
1,1'-carbonyldiimidazole,
unsym-N,N-diethylethylenediamine, and
N-[2-[(phenylmethyl)sulfonyl]ethyl]-2-propanamine, to give the free base of the title compound which is then reacted with maleic acid.

EXAMPLE 56

N'-[2-(Diethylamino)ethyl]-N-(1-methylethyl)-N-[2-[[3-(trifluoromethyl)phenyl]sulfonyl]ethyl]urea maleate The title compound is prepared by Method B, reacting in sequence:
1,1'-carbonyldiimidazole,
unsym-N,N-diethylethylenediamine, and
N-[2-[[3-(trifluoromethyl)phenyl]sulfonyl]ethyl]-2-propanamine, to give the free base of the title compound which is then reacted with maleic acid.

EXAMPLE 57

N'-[2-(Diethylamino)ethyl]-N-methyl-N-[2-(phenylsulfonyl)ethyl]urea maleate

The title compound is prepared by Method B, reacting in sequence:
1,1'-carbonyldiimidazole,
unsym-N,N-diethylethylenediamine, and
N-methyl-2-(phenylsulfonyl)ethanamine, to give the free base of the title compound which is then reacted with maleic acid.

EXAMPLE 58

N'-[2-(Diethylamino)ethyl]-N-(1-methylethyl)-N-[2-[(phenylmethyl)thio]ethyl]urea maleate The title compound is prepared by Method B, reacting in sequence:
1,1'-carbonyldiimidazole,
unsym-N,N-diethylethylenediamine, and
N-[2-[(phenylmethyl)thio]ethyl]-2-propanamine, to give the free base of the title compound which is then reacted with maleic acid.

EXAMPLE 59

N'-[2-(Diethylamino)ethyl]-N-(1-methylethyl)-N-[2-[(phenylmethyl)sulfinyl]ethyl]urea maleate The title compound is prepared by Method B, reacting in sequence:
1,1'-carbonyldiimidazole,
unsym-N,N-diethylethylenediamine, and
N-[2-[(phenylmethyl)sulfinyl]ethyl]-2-propanamine, to give the free base of the title compound which is then reacted with maleic acid.

EXAMPLE 60

N'-[2-(Diethylamino)ethyl]-N'-phenyl-N-[2-(phenylsulfonyl)ethyl]urea maleate

The title compound is prepared by Method C, reacting in sequence:
1,1'-carbonyldiimidazole,
2-(phenylsulfonyl)ethanamine, and
N,N-diethyl-N'-phenylethylenediamine, to give the free base of the title compound which is then reacted with maleic acid.

EXAMPLE 61

N'-[2-(Ethylamino)ethyl]-N-(1-methylethyl)-N-[2-(phenylsulfonyl)ethyl]urea, oxalate[1:1]

To a solution of phosgene (56 g of a 12.5% solution of phosgene in benzene: 6.72 g, 0.0679 mole) in 400 ml of methylene chloride and cooled in an ice bath was added a solution of 10.35 g (0.046 mole) of N-[2-(phenylsulfonyl)ethyl]-2-propanamine and 7.3 g (0.072 mole) of triethylamine in methylene chloride. The mixture was stirred at ambient temperature for 3 hr and then was extracted with several portions of dilute sulfuric acid. The solution was dried over magnesium sulfate and the solvent was removed in vacuo to give an oil. This was dissolved in 200 ml of anhydrous ether, and the ether was removed in vacuo to give an oil. This was dissolved in 100 ml of acetonitrile, and the solution was added to a solution of 50 g (0.568 mole) of N-ethylethylenediamine in 400 ml of acetonitrile. The mixture was stirred at room temperature for 16 hr. The solvent was removed in vacuo and the residue was partitioned between methylene chloride and dilute sodium hydroxide. The methylene chloride solution was dried over magnesium sulfate and the solvent was removed in vacuo to give an oil. This was dissolved in a mixture of methanol-diethyl ether, excess oxalic acid in methanol was added, and 17.0 g (86.5%) of white crystalline solid, m.p. 165°–166° C.

Analysis: Calculated for $C_{18}H_{29}N_3O_7S$: C, 50.10; H, 6.77; N, 9.74. Found: C, 49.77; H, 6.87; N, 9.76.

EXAMPLE 62

N'-[2-(Hexahydro-1H-azepin-1-yl)ethyl]-N-(1-methylethyl)-N-[2-(phenylsulfonyl)ethyl]urea oxalate[1:1]

A mixture of 4.50 g (0.0317 mole) of N-(2-aminoethyl)homopiperidine and 5.51 g (0.034 mole) of 1,1'-carbonyldiimidazole in 400 ml of tetrahydrofuran was stirred at room temperature for 1 hour. A solution of 6.58 g (0.029 mole) of 1-methyl-N-[2-(phenylsulfonyl)ethyl]ethanamine in 50 ml of tetrahydrofuran was added and the solution was refluxed for 20 hr. The solvent was removed in vacuo, and the residue was partitioned between methylene chloride and water. The methylene chloride solution was dried over magnesium sulfate and the solvent was removed in vacuo. The residue was dissolved in a mixture of methanol-diethyl ether, and the solution was treated with a solution of oxalic acid in methanol. A precipitate was collected to give 10.97 g (71.4%) of white crystalline solid, m.p. 100°–103° C.

Analysis: Calculated for $C_{22}H_{35}N_3O_7$: C, 54.42; H, 7.27; N, 8.65. Found: C, 54.10; H, 7.36; N, 8.73.

EXAMPLE 63

N-(1-Methylethyl)-N'-[2-[(methyl)phenylamino]ethyl]-N-[2-phenylsulfonyl)ethyl]urea A solution of 4.10 g (0.0253 mole) of 1,1'-carbonyldiimidazole and 3.60 g (0.024 mole) of N-(2-aminoethyl)-N-methylaniline was stirred at room temperature for 1 hr. A solution of 5.0 g (0.0220 mole) of 1-methyl-N-[2-(phenylsulfonyl)ethyl]ethanamine in 50 ml of tetrahydrofuran was added, and the solution was refluxed for 16 hr. The solvent was removed in vacuo and the residue was partitioned between methylene chloride and water. The methylene chloride solution was dried (magnesium sulfate), and the solvent was removed in vacuo to give an oil. This was crystallized from a mixture of methylene chloride, ether and hexane to give 7.15 g (80.6%) of white crystalline solid, m.p. 75°–77° C.

Analysis: Calculated for $C_{21}H_{29}N_3O_3S$: C, 62.50; H, 7.24; N, 10.41. Found: C, 62.40; H, 7.30; N, 10.52.

EXAMPLE 64

N'-[2-(Diethylamine)ethyl]-N-(2-phenylethyl)-N-[2-(phenylsulfonyl)ethyl]urea, oxalate[1:1]hemihydrate A solution of 3.89 g (0.024 mole) of 1,1'-carbonyldiimidazole and 2.55 g (0.22 mole) of diethylaminoethyl amine in 400 ml of tetrahydrofuran was stirred at room temperature for one hour. A solution of 5.43 g (0.0188 mole) 2,2-bis-(4-fluorophenyl)-1-(phenylsulfonyl)-4-piperidinemethanol in 50 ml of tetrahydrofuran was added, and the mixture was refluxed for 18 hrs. The solvent was removed in vacuo and the residue was partitioned between methylene chloride and water. The methylene chloride solution was dried over magnesium sulfate and the solvent was removed in vacuo to give the free base of the title compound as an oil. This was converted to the oxalate salt, and the salt was recrystallized twice from methanoldiethyl ether to give 7.17 g (71.9%) of white crystalline solid, m.p. 118°–119.5° C.

Analysis: Calculated for $C_{50}H_{72}N_6O_{15}S_2$: C, 56.59; H, 6.84; N, 7.91. Found: C, 56.32; H, 6.65; N, 8.00.

EXAMPLE 65

N-(1-Methylethyl)-N'-[2-(4-morpholinyl)ethyl]-N-[2-(phenylsulfonyl)ethyl]urea, maleate[1:1]

A solution of 5.51 g (0.034 mole) of 1,1'-carbonyldiimidazole and 4.03 g (0.031 mole) of N-(2-aminoethyl)morpholine in 400 ml of tetrahydrofuran was stirred at room temperature for one hr. A solution of 7.52 g (0.0286 mole) of N-isopropyl-2-(benzenesulfonyl)ethanamine in 50 ml of tetrahydrofuran was added and the mixture was refluxed for 18 hrs. The solvent was removed in vacuo, and the residue was partitioned between methylene chloride and water. The methylene chloride solution was dried over magnesium sulfate and the solvent was removed in vacuo to give the free base of the title compound as an oil. This was converted to the maleate salt, and the salt was recrystallized from methanol/diethyl ether to give 13.59 g (95.2%) of white crystalline solid, m.p. 161°–162° C.

Analysis: Calculated for $C_{22}H_{22}N_3O_3S$: C, 52.89; H, 6.66; N, 8.41. Found: C, 52.76; H, 6.66; N, 8.34.

EXAMPLE 66

N-(1-Methylethyl)-N-[2-(phenylsulfonyl)ethyl]-N'-[2-(1-piperidinyl)ethyl]urea, maleate[1:1]

By the same procedure described for Example 65, 6.47 g (0.0285 mole) of N-(2-benzenesulfonyl)ethyl-2-propanamine was reacted with the reaction product of 5.51 g (0.034 mole) of 1,1'-carbonyldiimidazole and 3.97 g (0.031 mole) of N-(2-aminoethyl)piperidine to give 12.31 g (86.8%) of white crystalline solid, m.p. 137°–138° C.

Analysis: Calculated for $C_{23}H_{35}N_3O_7S$: C, 55.52; H, 7.09; N, 8.44. Found: C, 55.25; H, 7.22; N, 8.64.

EXAMPLE 67

N'-[2-(2,6-Dimethylpiperidin-1-yl)ethyl]urea-N-(1-methylethyl)-N-[2-(phenylsulfonyl)ethyl]urea maleate The title compound is prepared in Method B and the procedure of Example 65 reacting in sequence:
N-(2-aminoethyl)-2,6-dimethyl-piperidin-1-yl,
1,1-carbonyldiimidazole, and
1-methyl-N-[2-(phenylsulfonyl)ethyl]ethanamine, to give the free base of the title compound which is then reacted with maleic acid.

EXAMPLE 68

N-(1-Methylethyl)-N'-[2-(4-phenyl-piperazin-1-yl)ethyl]-N-[2-(phenylsulfonyl)ethyl]urea maleate The title compound is prepared by Method B and the procedure of Example 65 reacting in sequence:
N-(2-aminoethyl)-4-phenylpiperazin-1-yl,
1,1'-carbonyldiimidazole, and
1-methyl-N-[2-(phenylsulfonyl)ethyl]ethanamine to give the free base of the title compound which is then reacted with maleic acid.

EXAMPLE 69

N-[2-(Diethylamino)ethyl]-N'-[2-(phenylsulfonyl)ethyl]urea maleate

The title compound is prepared by Method B, reacting in sequence:
1,1'-carbonyldiimidazole,
N,N-diethylaminoethylamine, and
2-(phenylsulfonyl)ethanamine
or by Method C, reacting in sequence:
1,1'-carbonyldiimidazole,
2-(phenylsulfonyl)ethanamine, and
N,N-diethylaminoethylamine,
to give the free base of the title compound which is then reacted with maleic acid.

EXAMPLE 70

N-(1-Methylethyl)-N-[2-(phenylsulfonyl)ethyl]-N'-[3-(piperidin-1-yl)propyl]urea maleate The title compound is prepared by Method B, reacting in sequence:
N-(3-aminopropyl)-piperidin-1-yl,
1,1'-carbonyldiimidazole, and
1-methyl-N-[2-(phenylsulfonyl)ethyl]ethanamine,
to give the free base of the title compound which is then reacted with maleic acid.

EXAMPLE 71

N-(1-Methylethyl)-N-[3-(phenylsulfonyl)propyl]-N'-[3-(piperidin-1-yl)propyl]urea maleate The title compound is prepared by Method B, reacting in sequence:
N-(3-aminopropyl)-piperidin-1-yl,
1,1'-carbonyldiimidazole, and
1-methyl-N-[3-(phenylsulfonyl)propyl]ethamamine,
to give the free base of the title compound which is then reacted with maleic acid.

EXAMPLE 72

N-(1-Methylethyl)-N-[3-(phenylsulfonyl)propyl]-N'-[2-(piperidin-1-yl)ethyl]urea maleate The title compound is prepared by Method B, reacting in sequence:
N-(3-aminoethyl)-piperidin-1-yl,
1,1'-carbonyldiimidazole, and
1-methyl-N-[3-(phenylsulfonyl)propyl]ethanamine,
to give the free base of the title compound which is then reacted with maleic acid.

EXAMPLE 73

N'-[2-(Di-n-propylamino)ethyl]-N-(1-methylethyl)-N-[2-(phenylsulfonyl)ethyl]urea maleate The title compound is prepared by Method B, reacting in sequence:
N,N-bis(n-propyl)aminoethylamine,
1,1'-carbonyldiimidazole, and
1-methyl-N-[2-(phenylsulfonyl)ethyl]ethanamine,
to give the free base of the title compound which is then reacted with maleic acid.

EXAMPLE 74

N'-[2-(Di-n-butylamino)ethyl]-N-(1-methylethyl)-N-[2-(phenylsulfonyl)ethyl]urea maleate The title compound is prepared by Method B, reacting in sequence:
N,N-bis(n-butyl)aminoethylamine,
1,1'-carbonyldiimidazole, and
1-methyl-N-[2-(phenylsulfonyl)ethyl]ethanamine,
to give the free base of the title compound which is then reacted with maleic acid.

EXAMPLE 75

N'-[4-(Diethylamino)butyl]-N-(1-methylethyl)-N-[2-(phenylsulfonyl)ethyl]urea maleate The title compound is prepared by Method B, reacting in sequence:
N,N-diethylamino-1,4-butanediamine,
1,1'-carbonyldiimidazole, and
1-methyl-N-[2-(phenylsulfonyl)ethyl]ethanamine,
to give the free base of the title compound which is then reacted with maleic acid.

EXAMPLE 76

N'-[2-(Diethylamino)ethyl]-N-(1-methylethyl)-N-[2-(phenylsulfonyl)ethyl]thiourea maleate The title compound is prepared by Method A, reacting in sequence:
thiophosgene; Proton Sponge ®,
1-methyl-N-[2-(phenylsulfonyl)ethyl]ethaneamine, and
unsym-diethylethylenediamine,
to give the free base of the title compound which is then reacted with maleic acid.

EXAMPLE 77

N-[2-(Diethylamino)ethyl]-N-ethyl-N'-(1-methylethyl)-N'-[2-(phenylsulfonyl)ethyl]urea citrate[1:1]

A mixture of 2.51 (0.0174 mole) of N,N,N'-triethylethylenediamine, 5.00 g (0.0173 mole) of N-(1-methylethyl)-N-[2-(phenylsulfonyl)ethyl]carbonyl chloride and 1.89 g (0.0187 mole) of triethylamine in 300 ml of tetrahydrofuran was refluxed overnight. The solvent was removed in vacuo, and the residue was partitioned between methylene chloride and dilute sodium hydroxide. The volume of the organic solution was doubled by the addition of ether, and the solution was extracted with six portions of water. The solution was dried over magnesium sulfate and the solvent was removed in vacuo to give an oil. A solution of this in methanol was treated with an equivalent of citric acid, and ether was added. A white solid precipitated to give 7.46 g (73.1%) of white, crystalline solid, m.p. 108°–110° C.

Analysis: Calculated for $C_{26}H_{43}N_3O_{10}S$: C, 52.96; H, 7.35; N, 7.13. Found: C, 52.82; H, 7.40; N, 7.07.

EXAMPLE 78

N-[2-(Diethylamino)ethyl]-N-ethyl-N'-[2-(phenylsulfonyl)ethyl]urea citrate[1:1]

A solution of 5.55 g (0.030 mole) of 2-(phenylsulfonyl)ethanamine and 5.35 g (0.033 mole) of 1,1'-carbonyldiimidazole in 400 ml of tetrahydrofuran was stirred at room temperature for 1 hr. A solution of 4.62 g (0.032 mole) of N,N,N'-triethylethylenediamine in 50 ml of tetrahydrofuran was added, and the mixture was refluxed for 16 hr. The solvent was removed in vacuo, and the residue was partitioned between a mixture of 300 ml of methylene chloride and 500 ml of ether and water. The organic phase was dried over magnesium sulfate, and the solvent was removed in vacuo to give an oil. A solution of the oil in methanol was treated with an equivalent of citric acid and ether was added. A white precipitate formed to give 8.54 g (52.0%) of white crystalline solid, m.p. 105°–107° C.

Analysis: Calculated for $C_{23}H_{37}N_3O_{10}S$: C, 50.45; H, 6.81; N, 7.67. Found: C, 50.28; H, 6.88; N, 7.60.

EXAMPLE 79

N-[2-(Diethylamino)ethyl]-N'-[2-(phenylsulfonyl)ethyl]urea oxalate hydrate[1:1:0.5]

A mixture of 4.70 g (0.0290 mole) of 1,1'-carbonyl diimidazole and 3.19 g (0.0275 mole) of N,N-diethylethylenediamine in 400 ml of tetrahydrofuran was stirred at room temperature for 1 hr. A solution of 4.92 g (0.0266 mole) of 2-(phenylsulfonyl)ethanamine in 50 ml of tetrahydrofuran was added, and the solution was refluxed for 16 hr. The solvent was removed in vacuo, and the residue was dissolved in a mixture of 200 ml of methylene chloride and 300 ml of ether. The organic solution was extracted with three portions of water and was dried over magnesium sulfate. The solvent was removed in vacuo to give an oil. This was converted to the oxalate salt, and the salt was recrystallized from methanolether to give 4.09 g (36.1%) of white crystalline salt, m.p. 95°–105° C.

Analysis: Calculated for $C_{17}H_{28}N_3O_{7.5}S$: C, 47.88; H, 6.62; N, 9.85. Found: C, 47.81; H, 6.37; N, 9.78.

EXAMPLE 80

N'-[2-(Diethylamino)ethyl]-N-[2-[(4-methoxyphenyl)sulfonyl]ethyl]-N-(1-methylethyl)urea A solution of 4.54 g (0.28 mole) of 1,1'-carbonyldiimidazole and 2.90 g (0.025 mole) of N,N-diethylethylenediamine in 400 ml of tetrahydrofuran was stirred at room temperature for 1 hr. A solution of 5.89 g (0.0229 mole) of N-[2-[(4-methoxyphenyl)sulfonyl]ethyl]-2-propanamine in 50 ml of tetrahydrofuran was added, and the mixture was refluxed overnight. The solvent was removed in vacuo, and the residue was dissolved in 800 ml of a 50/50 mixture of methylene chloride-ether. The organic solution was extracted with water and was dried over magnesium sulfate. The solvent was removed in vacuo to give an oil. This was crystallized from ether-hexane to give 6.16 g (67.3%) of white crystalline solid; m.p. 39.5°–42° C.

Analysis: Calculated for $C_{19}H_{33}N_3O_4S$: C, 57.12; H, 8.33; N, 10.52. Found: C, 56.99; H, 8.37; N, 10.65.

EXAMPLE 81

N'-[3-(Diethylamino)propyl]-N-(1-methylethyl)-N-[2-(phenylsulfonyl)ethyl]thiourea A solution of 5.0 g (0.022 mole) of N-[2-(phenylsulfonyl)ethyl]-2-propanamine and 4.30 g (0.025 mole) of 3-(N,N-diethylamino)propylisothiocyanate in 400 ml of acetonitrile was refluxed for 16 hr. The solvent was removed in vacuo and the residue was dissolved in ether. The solution was extracted with three portions of water and was dried over magnesium sulfate. The volume of the ether solution was reduced to 200 ml, and hexane was added until the solution became slightly cloudy. A white solid precipitated to give 6.76 g (76.9%) of white crystalline solid, m.p. 120°–121° C.

Analysis: Calculated for $C_{19}H_{33}N_3O_2S_2$: C, 57.11; H, 8.32; N, 10.52. Found: C, 57.37; H, 8.49; N, 10.47.

EXAMPLE 82

N'-[2-(Diethylamino)ethyl]-N-[2-[4-(1,1-dimethylethyl)phenyl]sulfonyl]ethyl]-N-(1-methylethyl)urea citrate[1:1]

A solution of 4.28 g (0.0264 mole) of 1,1'-carbonyldiimidazole and 2.78 g (0.024 mole) of N,N-diethylethylenediamine in 400 ml of tetrahydrofuran was stirred at room temperature for 1 hr. A solution of 7.04 g (0.022 mole) of N-[2-(4-t-butylphenylsulfonyl)ethyl]-2-propanamine in 50 ml of tetrahydrofuran was added, and the solution was refluxed for 15 hr. The solvent was removed in vacuo, and the residue was partitioned between ether and water. The ether solution was dried over magnesium sulfate and the solvent was removed in vacuo to give an oil, the free base of the title compound. This was converted to the citrate salt, and the salt was recrystallized from methanol-ether to give 9.86 g (72.5%) of white crystalline salt, m.p. 99°–102° C.

Analysis: Calculated for $C_{28}H_{47}N_3O_{10}S$: C, 54.44; H, 7.67; N, 6.80. Found: C, 54.16; H, 7.74; N, 6.75.

EXAMPLE 83

N'-[2-(Diethylamino)ethyl]-N-1-methylethyl)-N-[2-(phenylthio)ethyl]urea

A solution of 5.18 g (0.023 mole) of 1,1'-carbonyldiimidazole and 3.25 g (0.028 mole) of N,N-diethylethylenediamine in 400 ml of tetrahydrofuran was stirred at room temperature for 1 hr. A solution of 5.07 g (0.0260 mole) of N-[2-(phenylthio)ethyl]-2-propanamine in 50 ml of tetrahydrofuran was added, and the solution was refluxed for 15 hr. The solvent was removed in vacuo to give an oil. This was partitioned between ether and water. A TLC of the ether solution (silica gel, eluted with methanol) showed only one spot. The ether solution was dried over magnesium sulfate and the solvent was removed in vacuo to give the title compound as an oil.

$^1$H NMR $(CDCl_3)\delta 1.18$ (m, 12H, $CH(CH_3)_2$ and $N(CH_2CH_3)_2$, 2.5 (m, 6H, —$CH_2N(CH_2CH_3)_2$), 3.15 (m, 6H, —S—$CH_2$—$CH_2N$ and

4.15 (br S, 1H, NH exch), 7.35 (m, 5H, aromatic).

Analysis: Calculated for $C_{18}H_{31}N_3OS$: C, 64.05; H, 9.26; N, 12.45. Found: C, 63.77; H, 9.27; N, 12.06.

EXAMPLE 84

N'-[2-(Diethylamino)ethyl]-N-(1-methylethyl)-N-[2-(phenylsulfonyl)ethyl]thiourea A mixture of 2.78 g (0.024 mole) of N,N-diethylethylenediamine and 4.82 g (0.027 mole) of 1,1'-thiocarbonyldiimidazole in 400 ml of tetrahydrofuran was stirred at room temperature for 1 hr. A solution of 5.00 g (0.022 mole) of N-[2-(phenylsulfonyl)ethyl]-2-propanamine in 100 ml of tetrahydrofuran was added, and the solution was refluxed for 48 hrs. The solvent was removed in vacuo and the residue was dissolved in 400 ml of a 50/50 mixture of methylene chloride and ether. The organic solution was extracted with water and was dried over magnesium sulfate. The solvent was removed in vacuo, and the residue was recrystallized from a mixture of methylene chlorideether-hexane to give 5.95 g (72.5%) of pale yellow solid, m.p. 81.5°–82.5° C.

Analysis: Calculated for $C_{18}H_{31}N_3O_2S_2$: C, 56.07; H, 8.10; N, 10.90. Found: C, 56.28; H, 8.22; N, 10.91.

EXAMPLE 85

N'-[2-(Diethylamino)ethyl]-N-(1-methylethyl)-N-[2-[(phenylmethyl)sulfonyl]ethyl]urea oxalate[1:1]

A mixture of 2.78 g (0.024 mole) of N,N-diethylethylenediamine and 4.37 g (0.027 mole) of 1,1'-carbonyldiimidazole in 400 ml of tetrahydrofuran was stirred at room temperature for 1 hr. A solution of 5.30 g (0.022 mole) of N-[2-(benzylsulfonyl)ethyl]-2-propanamine in 50 ml of tetrahydrofuran was added, and the solution was refluxed for 20 hrs. The solvent was removed in vacuo, and the residue was dissolved in a mixture of 300 ml of ether and 100 ml of methylene chloride. The organic solution was extracted wih water and was dried over magnesium sulfate. The solvent was removed in vacuo to give an oil. This was converted to the oxalate salt, and the salt was recrystallized from methanol-ether to give 7.93 g (76.1%) of white crystalline solid, m.p. 111°–113° C.

Analysis: Calculated for $C_{21}H_{35}N_3O_7S$: C, 53.26; H, 7.45; N, 8.87. Found: C, 53.10; H, 7.53; N, 8.82.

EXAMPLE 86

N'-[3-(Diethylamino)propyl]-N-(1-methylethyl)-N-[2-[(phenylmethyl)sulfonyl]ethyl]urea oxalate[1:1]

A mixture of 3.13 g (0.0241 mole) of 3-(N,N-diethylamino)-1-propanamine and 4.40 g (0.0272 mole) of 1,1'-carbonyldiimidazole in 400 ml of tetrahydrofuran was stirred at room temperature for 1 hr. A solution of 5.35 g (0.0222 mole) of N-[2-(benzylsulfonyl)ethyl]-2-propanamine in 50 ml of tetrahydrofuran was added, and the solution was refluxed for 20 hrs. The solvent was removed in vacuo and the residue was dissolved in a mixture of 300 ml of ether and 100 ml of methylene chloride. The solution was extracted with water and was dried over magnesium sulfate. The solvent was removed in vacuo to give an oil. This was converted to the oxalate salt, and the salt was recrystallized from methanol-ether to give 8.61 g (79.5%) of a white, crystalline solid, m.p. 136.5°–137.5° C.

Analysis: Calculated for $C_{22}H_{37}N_3O_7S$: C, 54.19; H, 7.65; N, 8.62. Found: C, 54.24; H, 7.76; N, 8.68.

EXAMPLE 87

N'-[2-(Diethylamino)ethyl]-N-ethyl-N-[2-(phenylsulfonyl)ethyl]urea fumarate[1:1]

A solution of 11.25 g of N-ethyl-2-(phenylsulfonyl)ethanamine (0.053 mole) and triethylamine (10.73 g, 0.106 mole) in methylene chloride (24.2 ml) was added dropwise to a solution of phosgene (10.5 g, 0.106 mole) in methylene chloride (32.2 ml) maintained at a temperature below 15° C. The reaction mixture was stirred in the ice bath for 50 minutes and then kept cold overnight. The reaction mixture was then stirred in an ice bath and a 5% hydrochloric acid solution (13.2 ml) was added. The layers were separated, and the methylene chloride layer was washed twice with ice water. The methylene chloride layer was dried over molecular sieves, filtered and the solvent evaporated to give an oil which, upon trituration with petroleum ether, gave 12.0 g of solid. The solid was stirred in methylene chloride (41 ml) with N,N-diethylethylenediamine (5.29 g, 0.046 mole) overnight. An aqueous solution of potassium carbonate (12.2 g in 26 ml of water) was added and the layers were separated. The methylene chloride was washed twice with water, dried over molecular sieves, filtered, dried over anhydrous sodium sulfate and evaporated to give 17.0 g of an oil, the free base of the title compound. The free base was reacted with fumaric acid using isopropyl alcohol-diethyl ether to give 5.2 g of the fumarate salt, m.p. 104°–106° C.

Analysis: Calculated for $C_{21}H_{33}SO_7N_3$: C, 53.49; H, 7.05; N, 8.91. Found: C, 53.47; H, 7.11; N, 8.89.

EXAMPLE 88

N'-[4-(Diethylamino)butyl]-N-(1-methylethyl)-N-[2-(phenylsulfonyl)ethyl]urea

A solution of 4.40 g (0.0272 mole) of 1,1'-carbonyldiimidazole and 3.46 g (0.024 mole) of N,N-diethyl-1,4-butanediamine in 400 ml of tetrahydrofuran was stirred at room temperature for 1 hr. A solution of 5.00 g (0.0220 mole) of N-[2-(phenylsulfonyl)ethyl]-2-propanamine in 50 ml of tetrahydrofuran was added, and the solution was refluxed overnight. The solvent was removed in vacuo, and the residue was dissolved in 600 ml of a 50/50 mixture of ether and methylene chloride. The organic solution was extracted with three portions of water and was dried over magnesium sulfate. The solvent was removed in vacuo to give an oil. Flash chromatography on silica gel (methanol) gave 2.29 g (26.2%) of clear colorless oil: $^1$H NMR $(CDCl_3) \delta 7.4$–8.05 (m, 5, aromatic); 4.95 (br t, 1, NH), 4.03 (m, 1, J=3 HZ, $(CH_3)_2CH$) 3.40 (S, 4, $SO_2CH_2CH_2$—) 3.0–3.3 (br m, 2, $\overline{N}HCH_2$), 2.2–2.8 (m, 6, —$CH_2N(CH_2CH_3)_2$, 1.3–1.6 (m, 4, $CH_2CH_2CH_2N$), 1.10 (d, 6, J=3 HZ, $(CH_3)_2CH$), 1.0 (t, 6, $N(CH_2CH_3)_2$.

Analysis: Calculated for $C_{20}H_{35}N_3O_3S$: C, 60.42; H, 8.87; N, 10.57. Found: C, 60.05, H, 8.94; N, 10.45.

EXAMPLE 89

N'-[2-(Diethylamino)-1-methylethyl]-N-(1-methylethyl)-N-[2-(phenylsulfonyl)ethyl]urea A mixture of 12.15 g (0.075 mole) of 1,1'-carbonyl diimidazole and 7.50 g (0.0476 mole) of 1-diethylamino-2-propanamine in 400 ml of tetrahydrofuran was stirred at room temperature for 1 hr. A solution of 12.26 g (0.054 mole) of N-[2-(phenylsulfonyl)ethyl]-2-propanamine in 50 ml of tetrahydrofuran was added, and the solution was refluxed for 19 hr. The solvent was removed in vacuo, and the residue was dissolved in a 50/50 mixture of methylene chloride and ether. The organic solution was extracted with several portions of water and was dried over magnesium sulfate. The solvent was removed in vacuo to give an oil. Flash chromatography on silica gel (elution with methanol) gave 10.87 g (52.3 g) of clear colorless oil. $^1$H NMR $(CDCl_3)\delta 7.5$–8.15 (m, s. aromatic), 5.35 (br s, 1, NH), 4.1 (m, 1, $(CH_3)_2CH$), 3.45–4.0 (m, 1. $NHCH(CH_3)CH_2$), 2.5–2.85 (m, 6,–$CH_2CH_3$)), 0.85–1.3 (m, 15, $CH_3$ groups).

Analysis: Calculated for $C_{19}H_{33}N_3O_3S$: C, 59.60; H, 8.67; N, 10.96. Found: C, 59.19; H, 8.64; N, 10.98.

EXAMPLE 90

N-(1-Methylethyl)-N-[2-(phenylsulfonyl)ethyl]-N'-[3-(1-piperidinyl)propyl]urea

A mixture of 5.16 g (0.0319 mole) of 1,1'-carbonyldiimidazole and 4.16 g (0.029 mole) of N-(3-aminopropyl)piperidine in 400 ml of tetrahydrofuran was stirred at room temperature for 1 hr. A solution of 6.13 g (0.027 mole) of N-[2-(phenylsulfonyl)ethyl]-2-propanamine in 50 ml of tetrahydrofuran was added, and the mixture was refluxed for 20 hr. The solvent was removed in vacuo, and the residue was dissolved in a 60/40 mixture of ether and methylene chloride, respectively. The solution was extracted with three portions of water and was dried over magnesium sulfate. The solvent was removed in vacuo to give an oil. Flash chromatography on silica gel (chloroform and methanol, gradiently eluted with methanol up to 10% methanol) gave 2.89 g (27.1%) of oil: $^1$H NMR $(CDCl_3)\delta 7.4$–8.03 (m, 5, aromatic), 6.4 (br s, 1, NH) 3.88 (m. 1, $(CH_3)_2(H)$, 3.44 (s, 4, $SO_2CH_2CH_2$, 2.33 (br q, 2 $NHCH_2$), 2.2–2.5 (m. 6. $CH_2CH_2CH_2N$, and 2, 6-piperidine H), 1.3–1.83 (m, 8, $(CH_2CH_2CH_2N$, and 3, 4, 5-piperidine H), 1.1 (d, 6, $(CH_3)_2CH$).

Analysis: Calculated for $C_{20}H_{23}N_3O_3S$: C, 60.73; H, 8.41; N, 10.62. Found: C, 60.33; H, 8.46; N, 10.52.

EXAMPLE 91

N'-[2-(Diethylamino)ethyl]-N-(1-methylethyl)-N-[2-(phenylsulfinyl)ethyl]urea

A mixture of 4.70 g (0.029 mole) of 1,1'-carbonyldiimidazole- and 3.07 g (0.0265 mole) of N,N-diethylethylenediamine in 400 ml of tetrahydrofuran was stirred at room temperature for 1 hr. A solution of 8.00 g (0.0245 mole) of N-[2-(phenylsulfinyl)ethyl]-2-propanamine in 50 ml of tetrahydrofuran was added, and the mixture was refluxed for 16 hr. The solvent was removed in vacuo, and the residue was dissolved in ether. The ether solution was extracted with several portions of water. The aqueous extract was extracted with ether and then with methylene chloride; these organic extracts were combined with the original ether solution. The organic solution was dried over magnesium sulfate, and the solvent was removed in vacuo to give an oil. Flash chromatography on silica gel (methanol) gave 4.84 g (55.9%) of oil: $^1$H NMR $(CDC_3)$, $\delta 7.4$–7.75 (m, 5, aromatic), 5.5) (br s, 1, NH) 4.12 (m, 1, $(CH_3)_2CH$), 2.8–3.7 (m, 6, $SOCH_2CH_2$ and $NHCH_2$), 2.3–2.75 (m, 6, $CH_2N(CH_2CH_3)_2$), 0.8–1.3 (m, 12, $CH_3$ groups).

Analysis: Calculated for $C_{18}H_{31}N_3O_2S$: C, 61.16; H, 8.84; N, 11.89. Found: C, 60.70; H, 8.89; N, 11.91.

EXAMPLE 92

N'-[2-(Diethylamino)ethyl]-N-(phenylmethyl)-N-[2-(phenylsulfonyl)ethyl]urea

A mixture of 3.89 (0.024 mole) of 1,1'-carbonyldiimidazole and 2.55 g (0.022 mole) of N,N-diethylethylenediamine in 400 ml of tetrahydrofuran was stirred at room temperature for 1 hr. A solution of 5.70 g (0.0183 mole) of N-benzyl-2-phenylsulfonylethanamine in 50 ml of tetrahydrofuran was added, and the mixture was refluxed for 16 hr. The solvent was removed in vacuo, and the residue was partitioned between methylene chloride and water. The methylene chloride solution was dried over magnesium sulfate, and the solvent was removed in vacuo to give an oil. Flash chromatography on silica gel (methanol) gave 5.35 g (69.98%) of oil: $^1$H NMR $(CDCl_3)$ $\delta 7.45$–8.00 (m, 5, $C_6H_5SO_2$), 7.05–7.40 (m, 5, $C_6H_5CH_2$), 5.65 (br s, 1, NH), 4.2 (s, $C_6H_5CH_2$), 3.0–3.84 (m, 6, $SO_2CH_2CH_2$ and $NHCH_2$) 2.2–2.65 (m, 6, $CH_2N(CH_2CH_3)_2$), 0.90 (t, 6, $CH_3$).

Analysis: Calculated for $C_{22}H_{31}N_3O_3S$: C, 63.28; H, 7.48; N, 10.06. Found: C, 63.16; H, 7.49; N, 10.07.

EXAMPLE 93

N-[2-(Diethylamino)ethyl]-N-(1-methylethyl)-N'-[2-(phenylsulfonyl)ethyl]urea

A mixture of 6.96 g (0.0376 mole) of 2-phenylsulfonylethanamine and 6.64 g (0.041 mole) of 1,1'-carbonyldiimidazole in 400 ml of tetrahydrofuran was stirred at room temperature for 1 hr. A solution of 6.16 g (0.039 mole) of N-[2-(diethylamino)ethyl]-2-propanamine in 50 ml of tetrahydrofuran was added, and the mixture was refluxed for 13 hr. The solvent was removed in vacuo, and the residue was dissolved in a 50/50 mixture of ether and methylene chloride. The solution was extracted with water and was dried over magnesium sulfate. The solvent was removed in vacuo to give an oil. Flash chromatography on silica gel (methanol) gave 5.74 g (41.36%) of clear, colorless oil: $^1$H NMR (CDCl$_3$)δ8.5 (br s, 1, NH) 7.46–8.05 (m, 5, aromatic), 4.45 (m, 1, (CH$_3$)$_2$CH), 3.48 (br s, 4, SO$_2$CH$_2$CH$_2$), 3.0 (t, 2, CH$_2$CH$_2$N-Et$_2$) 2.3–2.8 (m, 6, CH$_2$N CH$_2$N(CH$_2$CH$_3$)$_2$), 0.90–1.2 (m, 12, CH$_3$ groups).

Analysis: Calculated for C$_{18}$N$_{31}$N$_3$O$_3$S: C, 58.51; H, 8.46; N, 11.37. Found: C, 58.17; H, 8.41; N, 11.37.

EXAMPLE 94

N'-[5-(Diethylamino)pentyl]-N-(1-methylethyl)-N-[2-(phenylsulfonyl)ethyl]urea

A mixture of 10.45 g (0.066 mole) of 5-(diethylamino)-1-pentanamine and 11.34 g (0.070 mole) of 1,1'-carbonyldiimidazole in 400 ml of tetrahydrofuran was stirred at room temperature for 1 hr. A solution of 14.5 g (0.0639 mole) of N-[(2-phenylsulfonyl)ethyl]-2-propanamine in 50 ml of tetrahydrofuran was added, and the solution was refluxed overnight. The solvent was removed in vacuo, and the residue partitioned between ether and water. The ether solution was dried over magnesium sulfate and the solvent was removed in vacuo to give an oil. This was flash chromatographed (silica gel; elution with methanol) to give 17.82 g (67.8%) of oil.

Analysis: Calculated for C$_{21}$H$_{37}$N$_3$O$_3$S: C, 61.28; H, 9.06; N, 10.21. Found: C, 60.74; H, 9.09; N, 10.20.

EXAMPLE 95

N-(1-Methylethyl)-N'-[3-(4-methyl-1-piperazinyl)propyl]-N-[2-(phenylsulfonyl)ethyl]urea maleate[1:2]

A mixture of 6.00 g (0.035 mole) of 1-(3-aminopropyl)-4-methylpiperazine and 6.97 g (0.043 mole) of 1,1'-carbonyldiimidazole in 400 ml of tetrahydrofuran was stirred at room temperature for 1 hr. A solution of 8.17 g (0.036 mole) of N-(2-phenylsulfonylethyl)-2-propanamine in 100 ml of tetrahydrofuran was added, and the mixture was refluxed for 16 hr. The solvent was removed in vacuo and the residue was partitioned between methylene chloride and water. The solution was dried over magnesium sulfate, and the solvent was removed in vacuo to give an oil. The oil was dissolved in methanol; a solution of two equivalents of maleic acid in methanol was added, and a white solid precipitated. This was collected to give 15.48 g (68.8%) of white crystalline solid; m.p. 162°–163° C. with decomposition.

Analysis: Calculated for C$_{28}$H$_{42}$N$_4$O$_{11}$S: C, 52.33; H, 6.59; N, 8.72. Found: C, 52.03; H, 6.62; N, 8.60.

EXAMPLE 96

N'-[2-(Diethylamino)ethyl]-N-(1-methylethyl)-N-[1-methyl-2-(phenylsulfonyl)ethyl]urea hydrate[1:1]

A solution of 3.71 g (0.032 mole) of N,N-diethylethylenediamine and 5.83 (0.036 mole) of 1,1'-carbonyldiimidazole in 400 ml of tetrahydrofuran was stirred at room temperature for 1 hr. A solution of 8.30 g (0.030 mole) of N-(2-propyl)-1-(phenylsulfonyl)-2-propanamine in 50 ml of tetrahydrofuran was added and the solution was refluxed overnight. The solvent was removed in vacuo, and the residue was partitioned between ether and water. The ether solution was dried over magnesium sulfate and the solvent was removed in vacuo to give an oil. The oil was flash chromatographed (silica gel; elution with methanol) to give an oil. Crystallization from ether gave 0.54 g (4.5%) of white, crystalline solid, m.p. 75°–80° C.

Analysis: Calculated for C$_{19}$H$_{35}$N$_3$O$_4$S: C, 56.83; H, 8.79; N, 10.46. Found: C, 56.73; H, 8.70; N, 10.41.

EXAMPLE 97

N-[2-(Diethylamino)ethyl]-N-methyl-N'-(1-methylethyl)-N'-[2-(phenylsulfonyl)ethyl]urea citrate hydrate[1:1:0.5]

A mixture of 6.65 g (0.023 mole) of N-(1-methylethyl)-N-[2-(phenylsulfonyl)ethyl]carbamic chloride; 3.0 g (0.023 mole) of N,N-diethyl-N'-methylethylenediamine and triethylamine (2.7 g, 0.0267 mole) in 400 ml of tetrahydrofuran was stirred at room temperature for 10 hr. The solvent was removed in vacuo, and the residue was dissolved in a 60/40 mixture of ether and methylene chloride. This solution was extracted with several portions of water and was dried over magnesium sulfate. The solvent was removed in vacuo to give an oil. This was dissolved in methanol, an excess of citric acid was added, and ether was added. A solid precipitated to give 11.08 g (82.4%) of white, crystalline solid; m.p. 77°–82° C.

Analysis: Calculated for C$_{25}$H$_{42}$N$_3$O$_{10.5}$S: C, 51.36; H, 7.24; N, 7.19. Found: C, 51.66; H, 7.17; N, 7.20.

EXAMPLE 98

N'-[2-(Dimethylamino)ethyl]-N-(1-methylethyl)-N-[4-(phenylsulfonyl)butyl]urea hydrate[1:0.5]

A solution of 1,1'-carbonyldiimidazole (6.00 g, 0.037 mole) and N,N-diethylethylenediamine (4.00 g, 0.034 mole) was stirred at room temperature for 2 hours in 200 ml of tetrahydrofuran. A solution of N-(1-methylethyl)-4-[phenylsulfonyl]-1-butylamine (free base 7.99 g, 0.0313 mole) in 100 ml of tetrahydrofuran was added and the solution was heated overnight at reflux. The reaction was stripped to dryness and the residue dissolved in chloroform. The chloroform was extracted with water, dried (sodium sulfate), filtered, and removed in vacuo. A dark brown oil was obtained upon removal of chloroform. This oil was subjected to flash chromatography on Silica Gel using 0.1N ammonium hydroxide-methanol for elution. This chromatography furnished 5.37 g (42.2% yield) of clear oil after drying in vacuo 18 hours at 60° C. $^1$H NMR (CDCl$_3$)δ7.8 (m, 5, aromatic), 5.25 (t, 1, NH), 4.15 (m, 1, methine), 3.2 (m, 6, SO$_2$CH$_2$ and methylenes adjacent to amide nitrogen, 2.5), (m, 6,

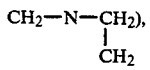

1.7 (m, 4, aliphatic—CH$_2$CH$_2$), 1.1 (m, 12, CH$_3$).

Analysis: Calculated for C$_{20}$H$_{36}$N$_3$O$_{3.5}$S: C, 59.08; H, 8.93; N, 10.33. Found: C, 58.96; H, 8.96; N, 10.23.

EXAMPLE 99

N'-[2-(Diethylamino)ethyl]-N-(1-methylethyl)-N-[5-(phenylsulfonyl)pentyl]urea hydrate[1:0.5]

A solution of 1,1'-carbonyldiimidazole (4.54 g, 0.028 mole) and N,N-diethylethylenediamine (2.90 g, 0.025 mole) in tetrahydrofuran was stirred for 1 hr at room temperature. A solution of N-(1-methylethyl)-5-(phenylsulfonyl)-1-pentanamine (6.74 g, 0.025 mole) in tetrahydrofuran (dried over 4 A molecular sieves) was added and the resulting solution was heated over night at gentle reflux. The reaction mixture was stripped to dryness and the residue dissolved in chloroform. The chloroform layer was extracted with water, dried (anhydrous sodium sulfate), filtered and the solvent removed to give a brown oil. The brown oil was subjected to flash column chromatography on Silica Gel using methanol for elution. Fractions of similar purity were combined, solvent removed, and the oil dried in vacuo at 60° C. overnight. This produced 7.00 g (66.6% yield) of brown oil. $^1$H NMR (CDCl$_3$), δ7.8 (m, 5, aromatic), 5.2 (b, 1, NH), 4.2 (m, 1, methine), 3.2 (m, 6, methylenes next to SO$_2$ and amide), 2.5 (m, 7, ½ H$_2$O and methylenes next to amine), 1.6 (m, 6, methylenes between SO$_2$ and amide), 1.1 (m, 12, CH$_3$).

Analysis: Calculated for C$_{21}$H$_{38}$N$_3$O$_{3.5}$S: C, 59.97; H, 9.11; N, 9.99. Found: C, 59.96; H, 9.08; N, 10.02.

EXAMPLE 100

N'-[2-(Diethylamino)ethyl]-N-(3-ethoxypropyl)-N-[2-(phenylsulfonyl)-ethyl]urea oxalate[1:1]

A solution of 6.80 g (0.042 mole) of 1,1'-carbonyldiimidazole and 4.06 g (0.035 mole) of N,N-diethylethylenediamine in 400 ml of tetrahydrofuran was stirred at room temperature for 1 hr. A solution of 8.97 g (0.0331 mole) of 3-ethoxy-N-[2-(phenylsulfonyl)ethyl]-1-propanamine in 50 ml of tetrahydrofuran was added, and the solution was refluxed for 16 hr. The solvent was removed in vacuo, and the residue was partitioned between ether and water. The ether phase was dried over magnesium sulfate, and the solvent was removed in vacuo to give the free base of the title compound. This was converted to the oxalate salt, and the salt was recrystallized from methanol-ether to give 8.11 g (48.7%) of white crystalline solid, m.p. 104°–105.5° C.

Analysis: Calculated for C$_{22}$H$_{37}$N$_3$O$_8$S: C, 52.47; H, 7.41; N, 8.34. Found: C, 52.38; H, 7.37; N, 8.44.

EXAMPLE 101

N'-[2-(Diethylamino)ethyl]-N-(2-methoxyethyl)-N-[2-(phenylsulfonyl)-ethyl]urea ethanedioate hydrate[1:0.5]

A mixture of 7.13 g (0.44 mole) of 1,1'-carbonyldiimidazole and 4.52 g (0.039 mole) of N,N-diethylethylenediamine in 400 ml of tetrahydrofuran was stirred at room temperature for 1 hr. A solution of 12.25 g (0.037 mole) of N-(2-methoxyethyl)-N-[2-(phenylsulfonyl)-ethyl]amine in 50 ml of tetrahydrofuran was added, and the solution was refluxed for 16 hr. The solvent was removed in vacuo, and the residue was partitioned between methylene chloride-ether mixture (60/40) and water. The organic phase was dried over magnesium sulfate and the solvent was removed in vacuo. Thr residue was converted to the oxalate salt, and this was recrystallized from methanol ether to give 11.67 g (65.1%) of white, crystalline solids, m.p. 103°–105° C.

Analysis: Calculated for C$_{20}$H$_{34}$N$_3$O$_{8.5}$S: C, 49.57; H, 7.07; N, 8.67 Found: C, 49.89; H, 6.86 N, 8.94

EXAMPLE 102

N'-[2-(Diethylamino)ethyl]-N-[2-[(4-ethoxyphenyl)sulfonyl]ethyl]-N-(1-methylethyl)urea citrate[1:1]

A mixture of 5.0 g (0.031 mole) of 1,1'-carbonyldiimidazole and 2.90 g (0.025 mole) of N,N-diethylethylenediamine in 400 ml of tetrahydrofuran was stirred at room temperature for 1 hr. A solution of 6.23 g (0.023 mole) of N-[2-[(4-ethoxyphenyl)sulfonyl]ethyl]-2-propanamine in 50 ml of tetrahydrofuran was added and the mixture was refluxed for 16 hr. The solvent was removed in vacuo and the residue was partitioned between methylene chloride and water. The methylene chloride phase was dried (magnesium sulfate), and the solvent was removed in vacuo to give the free base of the title compound as an oil. This was converted to the citrate salt and the salt was recrystallized from methanolether to give 11.55 g (82.98%) of white, crystalline solid, m.p. 123°–125° C.

Analysis: Calculated for C$_{26}$H$_{43}$N$_3$O$_{11}$S: C, 51.51; H, 7.16; N, 6.94. Found: C, 51.36; H, 7.20; N, 7.22.

EXAMPLE 103

N'-[2-(Diethylamino)ethyl]-N-[2-(phenylsulfonyl)ethyl]-N-(2-propenyl)urea citrate[1:1]

A mixture of 6.20 g (0.0383 mole) of 1,1'-carbonyldiimidazole and 3.71 g (0.032 mole) of N,N-diethylethylenediamine in 400 ml of tetrahydrofuran was stirred at room temperature for 1 hr. A solution of 6.80 g (0.030 mole) of N-[2-(phenylsulfonyl)ethyl]-2-propen-1-amine in 50 ml of tetrahydrofuran was added, and the mixture was refluxed for 20 hr. The solvent was removed in vacuo, and the residue was partitioned between methylene chloride and water. The methylene chloride solution was dried (magnesium sulfate), and the solvent was removed in vacuo to give the free base of the title compound. This was converted to the citrate salt, and the salt was recrystallized from methanol-ether to give 13.73 g (81.8%) of white crystalline solid, m.p. 92°–95° C.

Analysis: Calculated for C$_{24}$H$_{37}$N$_3$O$_{10}$S: C, 51.51; H, 6.66; N, 7.51. Found: C, 51.22; H, 6.71; N, 7.53.

EXAMPLE 104

N'-[5-(Diethylamino)pentyl]-N-(1-methylethyl-N-[2-(phenylsulfonyl)-ethyl]urea hydrate[1:0.5]

A sample of N'-[5-(diethylamino)pentyl]-N-(1-methylethyl-N-[2-(phenylsulfonyl)ethyl]urea was exposed to the atmosphere for 24 hr to give the hemihydrate.

Analysis: Calculated for C$_{21}$H$_{38}$N$_3$O$_{3.5}$S: C, 59.97; H, 9.11; N, 9.99. Found: C, 59.76; H, 9.16; N, 10.07.

EXAMPLE 105

N'-[2-(Diethylamino)ethyl]-N-[2-(4-hydroxyphenyl)sulfonyl]ethyl]-N-(1-methylethyl)urea citrate The title compound is prepared by Method B, reacting in sequence:
1,1'-carbonyldiimidazole,
N,N-diethylethylenediamine, and
N-[2-[(4-hydroxyphenyl)sulfonyl]ethyl]-2-propanamine to give the free base of the title compound which is reacted with citric acid.

EXAMPLE 106

N-[2-(Diethylamino)ethyl]-N-[2-(3,4-dimethoxyphenyl)sulfonyl]ethyl]-N-(1-methylethyl)urea citrate The title compound is prepared by Method B, reacting in sequence:
1,1'-carbonyldiimidazole,
N,N-diethylethylenediamine, and
N-[2-[(3,4-dimethoxyphenyl)sulfonyl]ethyl]-2-propanamine to give the free base of the title compound which is then reacted with citric acid.

EXAMPLE 107

N'-[2-(Diethylamino)ethyl]-N-[2-(4-dimethylaminophenyl)sulfonyl]ethyl]-N-(1-methylethyl)urea citrate The title compound is prepared by Method B, reacting in sequence:
1,1'-carbonyldiimidazole,
N,N-diethylethylenediamine, and
N-[2-[(4-dimethylaminophenyl)sulfonyl]ethyl]-2-propanamine to give the free base of the title compound which is then reacted with citric acid.

EXAMPLE 108

N-[2-(4-Aminophenyl)sulfonyl]ethyl]-N'-[2-(diethylamino)ethyl]-N-(1-methylethyl)urea citrate The title compound is prepared by Method B, reacting in sequence:
1,1'-carbonyldiimidazole,
N,N-diethylethylenediamine, and
N-[2-[(4-aminophenyl)sulfonyl]ethyl]-2-propanamine to give the free base of the title compound which is then reacted with citric acid.

TABLE 1

$$Ar-B-alk^1-N-\overset{R^1}{\underset{}{C}}-\overset{X}{\underset{}{C}}-\overset{R^2}{\underset{}{N}}-alk^2-N\overset{R^3}{\underset{R^4}{<}}$$

| Ex. No. | Ar | B | alk¹ | R¹ | X | R² | alk² | —NR³R⁴ | Salt | M.P., °C. |
|---|---|---|---|---|---|---|---|---|---|---|
| 1 | 4-Cl—C₆H₄— | —S— | —(CH₂)₂— | —CH(CH₃)₂ | O | H | —(CH₂)₂— | —N(CH₃)₂ | 1.5 fumarate | 101–103.5 |
| 2 | 2-C₁₀H₇— | —S— | —(CH₂)₂— | —CH(CH₃)₂ | O | H | —(CH₂)₂— | —N(CH₃)₂ | 1.5 succinate | 96–98 |
| 3 | 4-Cl—C₆H₄— | —S(O)₂— | —(CH₂)₂— | —CH(CH₃)₂ | O | H | —(CH₂)₂— | —N(CH₃)₂ | maleate | 134–135 |
| 4 | 4-Cl—C₆H₄— | —S(O)₂— | —(CH₂)₂— | —CH(CH₃)₂ | O | H | —(CH₂)₂— | —N(C₂H₅)₂ | tartrate | 135–137 |
| 5 | 4-Cl—C₆H₄— | —S(O)₂— | —(CH₂)₂— | H | O | —CH(CH₃)₂ | —(CH₂)₂— | —N(CH₃)₂ | maleate | 125–126.5 |
| 6 | 4-Cl—C₆H₄— | —S(O)— | —(CH₂)₂— | —CH(CH₃)₂ | O | H | —(CH₂)₂— | —N(CH₃)₂ | 0.5 fumarate | 141–142 |
| 7 | 4-Cl—C₆H₄— | —S(O)₂— | —(CH₂)₂— | —CH(CH₃)₂ | S | H | —(CH₂)₂— | —N(CH₃)₂ | fumarate | 112.5–114.5 |
| 8 | C₆H₅— | —S(O)₂— | —(CH₂)₂— | —CH(CH₃)₂ | O | H | —(CH₂)₂— | —N(CH₃)₂ | maleate | 103–105 |
| 9 | C₆H₅— | —S(O)₂— | —(CH₂)₂— | —CH(CH₃)₂ | O | H | —(CH₂)₂— | —N(C₂H₅)₂ | maleate | 88–90 |
| 10 | 1-C₁₀H₇— | —S(O)₂— | —(CH₂)₂— | —CH(CH₃)₂ | O | H | —(CH₂)₂— | —N(CH₃)₂ | maleate | 126–128 |
| 11 | inden-4-yl— | —S(O)₂— | —(CH₂)₂— | —CH(CH₃)₂ | O | H | —(CH₂)₂— | —N(C₂H₅)₂ | maleate | — |
| 12 | inden-5-yl— | —S(O)₂— | —(CH₂)₂— | —CH(CH₃)₂ | O | H | —(CH₂)₂— | —N(C₂H₅)₂ | maleate | — |
| 13 | 4-CH₃—C₆H₄— | —S(O)₂— | —(CH₂)₂— | —CH(CH₃)₂ | O | H | —(CH₂)₂— | —N(C₂H₅)₂ | maleate | — |
| 14 | 4-(OCH₃)—C₆H₄— | —S(O)₂— | —(CH₂)₂— | —CH(CH₃)₂ | O | H | —(CH₂)₂— | —N(C₂H₅)₂ | maleate | — |
| 15 | 3,5-Cl₂—C₆H₃— | —S(O)₂— | —(CH₂)₂— | —CH(CH₃)₂ | O | H | —(CH₂)₂— | —N(C₂H₅)₂ | maleate | — |
| 16 | 3,4,5-(OCH₃)₃—C₆H₂— | —S(O)₂— | —(CH₂)₂— | —CH(CH₃)₂ | O | H | —(CH₂)₂— | —N(C₂H₅)₂ | maleate | — |
| 17 | 4-F—C₆H₄— | —S(O)₂— | —(CH₂)₂— | —CH(CH₃)₂ | O | H | —(CH₂)₂— | —N(CH₃)₂ | maleate | — |
| 18 | 4-CF₃—C₆H₄— | —S(O)₂— | —(CH₂)₂— | —CH(CH₃)₂ | O | H | —(CH₂)₂— | —N(C₂H₅)₂ | maleate | — |
| 19 | 4-CN—C₆H₄— | —S(O)₂— | —(CH₂)₂— | —CH(CH₃)₂ | O | H | —(CH₂)₂— | —N(C₂H₅)₂ | maleate | — |
| 20 | 4-Cl—C₆H₄— | —S(O)₂— | —(CH₂)₂)₃— | —CH(CH₃)₂ | O | H | —(CH₂)₂— | —N(CH₃)₂ | maleate | — |
| 21 | C₆H₅— | —S(O)₂— | —(CH₂)₂— | H | O | —CH(CH₃)₂ | —(CH₂)₂— | —N(C₂H₅)₂ | maleate | 131–132 |
| 22 | C₆H₅— | —S(O)₂— | —(CH₂)₂— | —CH(CH₃)₂ | O | H | —(CH₂)₃— | —N(CH₃)₂ | maleate | — |
| 23 | C₆H₅— | —S(O)₂— | —(CH₂)₂— | —CH(CH₃)₂ | O | H | —(CH₂)₂— | 1-pyrrolinyl | maleate | — |
| 24 | C₆H₅— | —S(O)₂— | —(CH₂)₂— | —CH(CH₃)₂ | O | H | —(CH₂)₂— | 4-methyl-piperazin-1-yl | maleate | — |
| 25 | C₆H₅— | —S(O)₂— | —(CH₂)₂— | —C₆H₁₁ | O | H | —(CH₂)₂— | —N(C₂H₅)₂ | maleate | — |
| 26 | C₆H₅— | —S(O)₂— | —(CH₂)₂— | —C₆H₅ | O | H | —(CH₂)₂— | —N(C₂H₅)₂ | maleate | 169–170 |
| 27 | C₆H₅— | —S(O)₂— | —(CH₂)₂— | —CH₂—C₆H₅ | O | H | —(CH₂)₂— | —N(C₂H₅)₂ | maleate | — |
| 28 | C₆H₅— | —S(O)₂— | —(CH₂)₂— | —CH(CH₃)₂ | O | H | —(CH₂)₂— | —NH₂ | maleate | — |
| 29 | C₆H₅— | —S(O)₂— | —(CH₂)₂— | —CH(CH₃)₂ | O | H | —(CH₂)₂— | —NHCH₃ | maleate | — |
| 30 | C₆H₅— | —S(O)₂— | —(CH₂)₂— | —CH(CH₃)₂ | S | —CH₃ | —(CH₂)₂— | —N(C₂H₅)₂ | fumarate | — |
| 31 | 4-CH₃—C₆H₄ | —S(O)₂— | —(CH₂)₂— | —CH(CH₃)₂ | O | H | —(CH₂)₂— | —N(C₂H₅)₂ | fumarate | — |
| 32 | 4-Cl—C₆H₄— | —S(O)₂— | —(CH₂)₂— | —CH(CH₃)₂ | O | H | —(CH₂)₂— | —N(CH₃)₂ | maleate | — |
| 33 | 4-Cl—C₆H₄ | —S(O)₂— | —(CH₂)₃— | H | O | —CH(CH₃)₂ | —(CH₂)₂— | —N(CH₃)₂ | maleate | — |
| 34 | 1-C₁₀H₇ | —S— | —(CH₂)₂— | —CH(CH₃)₂ | O | H | —(CH₂)₂— | —N(CH₃)₂ | maleate | — |
| 35 | 1-C₁₀H₇ | —S(O)— | —(CH₂)₂ | —CH(CH₃)₂ | O | H | —(CH₂)₂— | —N(C₂H₅)₂ | maleate | — |
| 36 | 4-NO₂—C₆H₄ | —S(O)₂— | —(CH₂)₂— | —CH(CH₃)₂ | O | H | —(CH₂)₂— | —N(CH₃)₂ | maleate | — |
| 37 | 1-C₁₀H₇ | —S— | —(CH₂)₂ | —CH(CH₃)₂ | O | H | —(CH₂)₂— | —N(CH₃)₂ | oxalate | 101.5–104 |
| 38 | 4-CH₃—C₆H₄ | —S(O)₂— | —(CH₂)₂— | —CH(CH₃)₂ | O | H | —(CH₂)₂— | —N(C₂H₅)₂ | tartrate | 122–125 |

TABLE 1

$$Ar-B-alk^1-N(R^1)-C(=X)-N(R^2)-alk^2-N(R^3)(R^4)$$

| Ex. No. | Ar | B | alk¹ | R¹ | X | R² | alk² | —NR³R⁴ | Salt | M.P., °C. |
|---|---|---|---|---|---|---|---|---|---|---|
| 39 | 3,4-(Cl)₂—C₆H₃— | —S(O)₂— | —(CH₂)₂— | —CH(CH₃)₂ | O | H | —(CH₂)₂— | —N(CH₃)₂ | maleate | 145–146 |
| 40 | 4-CH₃—C₆H₄— | —S(O)— | —(CH₂)₂— | —CH(CH₃)₂ | O | H | —(CH₂)₂— | —N(C₂H₅)₂ | 0.5 H₂O | oil |
| 41 | C₆H₅— | —S(O)₂— | —(CH₂)₃— | —CH(CH₃)₂ | O | H | —(CH₂)₃— | —N(C₂H₅)₂ | oxalate 0.5 H₂O | 120–121.5 |
| 42 | C₆H₅— | —S(O)₂— | —(CH₂)₂— | —CH(CH₃)₂ | O | H | —(CH₂)₂— | —N(C₂H₅)₂ | oxalate 0.5 H₂O | 117–118.5 |
| 43 | C₆H₅— | —S(O)₂— | —(CH₂)₃— | —CH(CH₃)₂ | O | H | —(CH₂)₃— | —N(C₂H₅)₂ | ¼ H₂O | oil |
| 44 | 4-F—C₆H₄— | —S(O)₂— | —(CH₂)₂— | —CH(CH₃)₂ | O | H | —(CH₂)₂— | —N(C₂H₅)₂ | — | oil |
| 45 | C₆H₅— | —S(O)₂— | —(CH₂)₂— | —CH(CH₃)₂ | O | —CH₃ | —(CH₂)₂— | —N(C₂H₅)₂ | maleate | oil |
| 46 | C₆H₅— | —S(O)₂— | —(CH₂)₂— | —CH(CH₃)₂ | O | H | —(CH₂)₂— | —N[—CH(CH₃)₂]₂ | — | — |
| 47 | C₆H₅— | —S(O)₂— | —(CH₂)₂— | —CH(CH₃)₂ | O | H | —(CH₂)₂— | —N(CH₃)[—(CH₂)₂—φ] | 0.5 H₂O | — |
| 48 | C₆H₅— | —S(O)₂— | —(CH₂)₂— | —CH(CH₃)₂ | O | H | —(CH₂)₂— | —N(CH₃)(—CH₂φ) | — | oil |
| 49 | 4-Br—C₆H₄— | —S(O)₂— | —(CH₂)₂— | —CH(CH₃)₂ | O | H | —(CH₂)₂— | —N(C₂H₅)₂ | maleate | — |
| 50 | 4-t-Bu—C₆H₄— | —S(O)₂— | —(CH₂)₂— | —CH(CH₃)₂ | O | H | —(CH₂)₂— | —N(C₂H₅)₂ | maleate | — |
| 51 | C₆H₅— | —S(O)₂— | —(CH₂)₂— | —CH₃ | O | —CH(CH₃)₂ | —(CH₂)₂— | —N(C₂H₅)₂ | maleate | — |
| 52 | 2-furanyl-CH₂— | —S— | —(CH₂)₂— | —CH(CH₃)₂ | O | H | —(CH₂)₂— | —N(C₂H₅)₂ | maleate | — |
| 53 | 2-furanyl-CH₂— | —S(O)₂— | —(CH₂)₂— | —CH(CH₃)₂ | O | H | —(CH₂)₂— | —N(C₂H₅)₂ | maleate | — |
| 54 | 2-furanyl-CH₂— | —S(O)— | —(CH₂)₂— | —CH(CH₃)₂ | O | H | —(CH₂)₂— | —N(C₂H₅)₂ | maleate | — |
| 55 | C₆H₅—CH₂— | —S(O)₂— | —(CH₂)₂— | —CH(CH₃)₂ | O | H | —(CH₂)₂— | —N(C₂H₅)₂ | maleate | — |
| 56 | 3-CF₃—C₆H₄— | —S(O)₂— | —(CH₂)₂— | —CH(CH₃)₂ | O | H | —(CH₂)₂— | —N(C₂H₅)₂ | maleate | — |
| 57 | C₆H₅— | —S(O)₂— | —(CH₂)₂— | —CH₃ | O | H | —(CH₂)₂— | —N(C₂H₅)₂ | maleate | — |
| 58 | C₆H₅—CH₂— | —S— | —(CH₂)₂— | —CH(CH₃)₂ | O | H | —(CH₂)₂— | —N(C₂H₅)₂ | maleate | — |
| 59 | C₆H₅—CH₂— | —S(O)— | —(CH₂)₂— | —CH(CH₃)₂ | O | H | —(CH₂)₂— | —N(C₂H₅)₂ | maleate | — |
| 60 | C₆H₅— | —S(O)₂— | —(CH₂)₂— | H | O | C₆H₅ | —(CH₂)₂— | —N(C₂H₅)₂ | maleate | 165–166 |
| 61 | C₆H₅— | —S(O)₂— | —(CH₂)₂— | —CH(CH₃)₂ | O | H | —(CH₂)₂— | —NHC₂H₅ | oxalate | 100–103 |
| 62 | C₆H₅— | —S(O)₂— | —(CH₂)₂— | —CH(CH₃)₂ | O | H | —(CH₂)₂— | hexahydro-1-H—azepin-1-yl | oxalate | — |
| 63 | C₆H₅— | —S(O)₂— | —(CH₂)₂— | —CH(CH₃)₂ | O | H | —(CH₂)₂— | —N(CH₃)(C₆H₅) | — | 75–77 |
| 64 | C₆H₅— | —S(O)₂— | —(CH₂)₂— | —CH₂CH₂— | O | H | —(CH₂)₂— | —N(C₂H₅)₂ | oxalate-.05 H₂O | 118–119.5 |
| 65 | C₆H₅— | —S(O)₂— | —(CH₂)₂— | —CH(CH₃)₂ | O | H | —(CH₂)₂— | 4-morpholinyl | maleate | 161–162 |
| 66 | C₆H₅— | —S(O)₂— | —(CH₂)₂— | —CH(CH₃)₂ | O | H | —(CH₂)₂— | —1-piperidinyl | maleate | 137–138 |
| 67 | C₆H₅— | —S(O)₂— | —(CH₂)₂— | —CH(CH₃)₂ | O | H | —(CH₂)₂— | 2,6-(CH₃)₂—piperidin-1-yl | maleate | — |

TABLE 1

$$Ar-B-alk^1-N-\overset{R^1}{\underset{}{C}}=\overset{X}{\underset{}{}}\overset{R^2}{\underset{}{N}}-alk^2-N\overset{R^3}{\underset{R^4}{}}$$

| Ex. No. | Ar | B | alk¹ | R¹ | R² | X | alk² | —NR³R⁴ | Salt | M.P., °C. |
|---|---|---|---|---|---|---|---|---|---|---|
| 68 | C₆H₅— | —S(O)₂— | —(CH₂)₂— | —CH(CH₃)₂ | H | O | —(CH₂)₂— | 4-phenyl-piperazin-1-yl | maleate | — |
| 69 | C₆H₅— | —S(O)₂— | —(CH₂)₂— | H | H | O | —(CH₂)₂— | —N(C₂H₅)₂ | maleate | — |
| 70 | C₆H₅— | —S(O)₂— | —(CH₂)₂— | —CH(CH₃)₂ | H | O | —(CH₂)₃— | piperidin-1-yl | maleate | — |
| 71 | C₆H₅— | —S(O)₂— | —(CH₂)₃— | —CH(CH₃)₂ | H | O | —(CH₂)₂— | piperidin-1-yl | maleate | — |
| 72 | C₆H₅— | —S(O)₂— | —(CH₂)₂— | —CH(CH₃)₂ | H | O | —(CH₂)₂— | piperidin-1-yl | maleate | — |
| 73 | C₆H₅— | —S(O)₂— | —(CH₂)₂— | —CH(CH₃)₂ | H | O | —(CH₂)₂— | —N(C₃H₇)₂ | maleate | — |
| 74 | C₆H₅— | —S(O)₂— | —(CH₂)₂— | —CH(CH₃)₂ | H | O | —(CH₂)₂— | —N(C₄H₉)₂ | maleate | — |
| 75 | C₆H₅— | —S(O)₂— | —(CH₂)₂— | —CH(CH₃)₂ | H | O | —(CH₂)₄— | —N(C₂H₅)₂ | maleate | — |
| 76 | C₆H₅— | —S(O)₂— | —(CH₂)₂— | —CH(CH₃)₂ | H | O | —(CH₂)₂— | —N(C₂H₅)₂ | maleate | 108–110 |
| 77 | C₆H₅— | —S(O)₂— | —(CH₂)₂— | —CH(CH₃)₂ | —C₂H₅ | O | —(CH₂)₂— | —N(C₂H₅)₂ | citrate | 105–107 |
| 78 | C₆H₅— | —S(O)₂— | —(CH₂)₂— | H | —C₂H₅ | O | —(CH₂)₂— | —N(C₂H₅)₂ | oxalate 0.5 H₂O | 95–105 |
| 79 | 4-OCH₃—C₆H₄— | —S(O)₂— | —(CH₂)₂— | H | H | O | —(CH₂)₂— | —N(CH₂H₅)₂ | — | 39.5–42 |
| 80 | 4-C—(CH₃)₃C₆H₄— | —S(O)₂— | —(CH₂)₂— | —CH(CH₃)₂ | H | O | —(CH₂)₂— | —N(C₂H₅)₂ | — | 120–121 |
| 81 | C₆H₅— | —S— | —(CH₂)₂— | —CH(CH₃)₂ | H | O | —(CH₂)₃— | —N(C₂H₅)₂ | citrate | 99–102 |
| 82 | C₆H₅— | —S(O)₂— | —(CH₂)₂— | —CH(CH₃)₂ | H | S | —(CH₂)₂— | —N(C₂H₅)₂ | — | oil |
| 83 | C₆H₅— | —S(O)₂— | —(CH₂)₂— | —CH(CH₃)₂ | H | O | —(CH₂)₂— | —N(C₂H₅)₂ | — | 81.5–82.5 |
| 84 | C₆H₅— | —S(O)₂— | —(CH₂)₂— | —CH(CH₃)₂ | H | S | —(CH₂)₂— | —N(C₂H₅)₂ | oxalate | 111–113 |
| 85 | C₆H₅— | —S(O)₂— | —(CH₂)₂— | —CH(CH₃)₂ | H | O | —(CH₂)₃— | —N(C₂H₅)₂ | oxalate | 136.5–137.5 |
| 86 | C₆H₅— | —S(O)₂— | —(CH₂)₂— | —CH(CH₃)₂ | H | O | —(CH₂)₂— | —N(C₂H₅)₂ | fumarate | 104–106 |
| 87 | C₆H₅— | —S(O)₂— | —(CH₂)₂— | —C₂H₅ | H | O | —(CH₂)₂— | —N(C₂H₅)₂ | — | — |
| 88 | C₆H₅— | —S(O)₂— | —(CH₂)₂— | —CH(CH₃)₂ | H | O | —(CH₂)₄— | —N(C₂H₅)₂ | — | — |
| 89 | C₆H₅— | —S(O)₂— | —(CH₂)₂— | —CH(CH₃)₂ | H | O | —CH(CH₃)—CH₂— | —N(C₂H₅)₂ | — | oil |
| 90 | C₆H₅— | —S(O)₂— | —(CH₂)₂— | —CH(CH₃)₂ | H | O | —(CH₂)₃— | piperidin-1-yl | — | oil |
| 91 | C₆H₅— | —S(O)— | —(CH₂)₂— | —CH(CH₃)₂ | H | O | —(CH₂)₂— | —N(C₂H₅)₂ | — | oil |
| 92 | C₆H₅— | —S(O)₂— | —(CH₂)₂— | —CH₂C₆H₅ | H | O | —(CH₂)₂— | —N(C₂H₅) | — | oil |
| 93 | C₆H₅— | —S(O)₂— | —(CH₂)₂— | H | —CH(CH₃)₂ | O | —(CH₂)₅— | —N(C₂H₅)₂ | — | oil |
| 94 | C₆H₅— | —S(O)₂— | —(CH₂)₂ | —CH(CH₃)₂ | H | O | —(CH₂)₂— | —N(C₂H₅)₂ | — | oil |
| 95 | C₆H₅ | —S(O)₂— | —(CH₂)₂— | —CH(CH₃)₂ | H | O | —(CH₂)₃— | 4-CH₃—piperazin-1-yl | maleate | 162–163 |
| 96 | C₆H₅— | —S(O)₂— | —CH₂—CH—CH₃ | —CH(CH₃)₂ | H | O | —(CH₂)₂— | —N(C₂H₅)₂ | hydrate | 75–80 |
| 97 | C₆H₅— | —S(O)₂— | —(CH₂)₂— | —CH(CH₃)₂ | —CH₃ | O | —(CH₂)₂— | —N(C₂H₅)₂ | citrate 0.5 H₂O | 77–82 |
| 98 | C₆H₅— | —S(O)₂— | —(CH₂)₄— | —CH(CH₃)₂ | H | O | —(CH₂)₂— | —N(C₂H₅)₂ | 0.5 H₂O | oil |
| 99 | C₆H₅— | —S(O)₂— | —(CH₂)₅— | —CH(CH₃)₂ | H | O | —(CH₂)₂— | —N(C₂H₅)₂ | 0.5 H₂O | oil |
| 100 | C₆H₅— | —S(O)₂— | —(CH₂)₂— | —(CH₂)₃—OC₂H₅ | H | O | —(CH₂)₂— | —N(C₂H₅)₂ | oxalate | 104–105.5 |
| 101 | 4-OC₂H₅C₆H₄— | —S(O)₂— | —(CH₂)₂— | —(CH₂)₂—OCH₃ | H | O | —(CH₂)₂— | —N(C₂H₅)₂ | oxalate 0.5 H₂O | 103–105 |
| 102 | C₆H₅— | —S(O)₂— | —(CH₂)₂— | —CH₂CH=H₂ | H | O | —(CH₂)₂— | —N(C₂H₅)₂ | citrate | 123–125 |
| 103 | C₆H₅— | —S(O)₂— | —(CH₂)₂— | —CH(CH₃)₂ | H | O | —(CH₂)₂— | —N(C₂H₅)₂ | citrate | 92–95 |
| 104 | 4-OH—C₆H₄— | —S(O)₂— | —(CH₂)₂— | —CH(CH₃)₂ | H | O | —(CH₂)₅— | —N(C₂H₅)₂ | 0.5 hydrate | — |
| 105 | 3,4-(OCH₃)₂—C₆H₃— | —SO₂— | —(CH₂)₂— | —CH(CH₃)₂ | H | O | —(CH₂)₂— | —N(C₂H₅)₂ | citrate | — |
| 106 | 4-(CH₃)₂—N—C₆H₄— | —SO₂— | —(CH₂)₂— | —CH(CH₃)₂ | H | O | —(CH₂)₂— | —N(C₂H₅)₂ | citrate | — |
| 107 | 4-NH₂—C₆H₄— | —SO₂— | —(CH₂)₂— | —CH(CH₃)₂ | H | O | —(CH₂)₂— | —N(C₂H₅)₂ | citrate | — |
| 108 | | | | | | | | | | |

PHARMACOLOGY

The action of compounds of this invention in correcting cardiac arrhythmias or preventing cardiac arrhythmias is demonstrated by the following procedures:

OUABIAN INDUCED ARRHYTHMIAS

Correction of existing cardiac arrhythmias of ventricular origin is carried out on (1) adult mongrel dogs which are under barbiturate anesthesia during the test. A Grass Model 7 polygraph was used for recording femoral arterial blood pressure (Statham P23AC transducer) and the electrocardiogram (Grass 7P4 preamplifier). Ouabain was given intravenously in an initial dose of 40 µg/kg and in a second dose of 20 µg/kg 30 minutes after the first dose and in subsequent doses of 10 µg/kg which were repeated at 15 min. intervals as required for producing cardiac arrhythmias that persisted for at least 15 minutes. When the arrhythmias were established, the test compounds were administered by infusion (Harvard Model 942 Infusion Pump) into a femoral vein at a rate of 1 mg/kg/min. Concentration of compound was adjusted according to the weight of the dog to allow a volume infusion of 1 ml/min. The compound was considered to be active as antiarrhythmic agent if reversion to to sinus rhythm occurred which was maintained for at least 30 min.

CORONARY ARTERY LIGATION INDUCED ARRHYTHMIAS

Adult mongrel dogs which are in the conscious state were used for the test and cardiac arrhythmias were induced by prior (22-24 hr) surgical preparation in which blood flow through a coronary artery was occluded by use of a constrictor device as reported by Smith et al, 1973. A Grass Model 79 polygraph was used for recording the electrocardiogram (Grass 7P4 preamplifier).

The test compound was administered by infusion (Harvard Model 942 Infusion Pump) into a sapheneous vein to one group of dogs at a rate of 0.5 mg/kg/min. Concentration of compound was adjusted according to the weight of the dog to allow a volume of infusion of 0.5 ml/min. The test compound was administered orally by gavage to another group of dogs at dose levels of 10 through 40 mg/kg. The test compound was prepared in distilled water to give a total volume of 20 ml. Following the administration of the test compound, the heart rate, number of ectopic cardiac beats per min, and the percent ectopic beats (ectopic beats/HR X100) were recorded at 15 min. intervals. The compound was considered active if it abolished the ectopic ventricular frequency and caused a return to normal sinus rhythm within 2 hours of administration.

Data obtained for one preferred compound; namely, N'-[2-(diethylamino)ethyl]-N-(1-methylethyl)-N-[2-(phenylsulfonyl)ethyl]urea as represented by its maleate salt of Example 9 are shown in Table 2. The other compounds of this invention show qualitatively similar effects in one or more types of arrhythmias as represented by the foregoing tests. In general the compounds of this invention exhibit less CNS side effects than quinidine or lidocaine. The sulfones being superior in this respect at the same time exhibiting excellent antiarrhythmic activity.

TABLE 2

Effect of Compound of Example 9: N'—[2-(diethylamino)ethyl]-N—(1-methylethyl)-N—[2-phenylsulfonyl)ethyl urea on Cardiac Arrhythmias in Dogs

| Arrhythmia Model | Correcting Dose Range mg/kg I.V. |
|---|---|
| Ouabain-Induced[1] | 4-15 |
| Coronary Artery Ligation Induced[2] | 2-5 |

[1]Cardiac arrhythmias produced by method of Lucchessi and Hardman, 1961, J. Pharmacol. Exp. Ther. 132, 372-381.
[2]Cardiac arrhythmias produced by modification of method of Harris, 1950, Circulation 1, 1318, as reported by Smith et al, 1973, Pharmacologist 15, 192.

PHARMACEUTICAL COMPOSITIONS

The invention further provides pharmaceutical compositions for administration to a living animal body comprising, as active ingredients, at least one of the compounds according to the invention in association with a pharmaceutical carrier or excipient. The compounds are thus presented in a therapeutic composition suitable for oral, rectal, parenteral or intracardial administration. Thus, for example, compositions for oral administration are preferably solids and can take the form of capsules, tablets or coated tablets containing carriers conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid; e.g., water, or a parenterally acceptable oil; e.g., arachis oil, contained in ampoules.

In compositions for rectal administration the carrier can comprise a suppository base; e.g., cocoa butter, or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be obtained consistent with the dosage form employed. The exact individual dosages, as well as daily dosages, will, of course, be determined according to standard medical principles under the direction of a physician or veterinarian. Generally, the pharmacology on animals suggests the the oral dosage effective to correct arrhythmias will be about 3 times that of the intravenous dosage. The animal data also suggest dosage requirements will be about half that of quinidine for the more active compounds.

Based on the animal data, allowing for variation in species and severity of cardiac arrhythmia unit dosages containing an amount of compound equivalent to about 1 to about 100 mg/kg of body weight, are contemplated. Based on all of the above considerations, a choice in a range of unit oral dosages for humans of about 10 to about 1000 mg is contemplated, preferably about 10 to 600 mg for a more active compound such as Example 9. Daily dosages of about 30 to 2400 mg are contemplated for humans and obviously several unit dosage forms may be administered at about the same time. However, the scope of the invention is not to be limited by these contemplations due to the uncertainty in transpositions discussed above.

Examples of unit dosage compositions are as follows:

Capsules

| Ingredients | Per Cap. |
|---|---|
| 1. Active ingredient | 10.0 mg. |
| 2. Lactose | 146.0 mg. |
| 3. Magnesium Stearate | 4.0 mg. |

Procedure
1. Blend 1, 2 and 3.
2. Mill this blend and blend again.
3. This milled blend is then filled into #1 hard gelatin capsules.

Tablets (10 mg)

| Ingredients | Mg./Tab. |
|---|---|
| 1. Active ingredient | 10.0 mg. |
| 2. Corn starch | 20.0 mg. |
| 3. Kelacid | 20.0 mg. |
| 4. Keltose | 20.0 mg. |
| 5. Magnesium stearate | 1.3 mg. |

Tablets (50 mg)

| Ingredients | Mg/Tab. |
|---|---|
| 1. Active ingredient | 50.0 mg. |
| 2. Milo starch | 20.0 mg. |
| 3. Corn starch | 38.0 mg. |
| 4. Lactose | 90.0 mg. |
| 5. Calcium stearate | 2.0 mg. |
| | 200.0 mg. |

Procedure
1. Blend 1, 2, 3 and 4.
2. Add sufficient water portionwise to the blend from step #1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

Intravenous Injection

| Ingredients | Per ml. |
|---|---|
| 1. Active ingredient | 1.0 mg. |
| 2. pH 4.0 Buffer solution | q.s. to 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

Intramuscular Injection

| Ingredients | Per ml. |
|---|---|
| 1. Active ingredients | 5.0 mg. |
| 2. Isotonic Buffer solution 4.0 | q.s. to 1.0 ml. |

Procedure
1. Dissolve the active ingredient in the buffer solution.
2. Aseptically filter the solution from step #1.

Intramuscular Injection

3. The sterile solution is now aseptically filled into sterile ampuls.
4. The ampuls are sealed under aseptic conditions.

Suppositories

| Ingredients | Per Supp. |
|---|---|
| 1. Active ingredient | 10.0 mg. |
| 2. Polyethylene Glycol 1000 | 1350.0 mg. |
| 3. Polyethylene Glycol 4000 | 450.0 mg. |

Procedure
1. Melt 2 and 3 together and stir until uniform.
2. Dissolve #1 in the molten mass from step 1 and stir until uniform.
3. Pour the molten mass from step 2 into suppository molds and chill.
4. Remove the suppositories from molds and wrap.

Therapeutic compositions having cardiac arrhythmia inhibiting activity in dosage unit form, comprising a pharmaceutical carrier and a cardiac arrhythmia inhibiting amount of a compound of Formula I or a pharmaceutically acceptable acid addition salt thereof are therefore an embodiment of this invention.

Various modifications and equivalents will be apparent to one skilled in the art and may be made in the compounds, method, and compositions of the present invention without departing from the spirit or scope thereof, and it is therefore to be understood that the invention is to be limited only by the scope of the appended claims.

What is claimed is:

1. A compound selected from the group having the formula

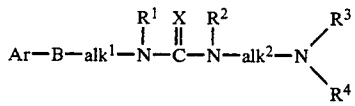

wherein;

Ar is selected from the group consisting of 1 and 2-naphthyl, 2,3-dihydro-1H-inden-4(or 5)yl, 2-furanyl, phenyl or phenyl substituted by 1-3 radicals which may be the same or different selected from the group consisting of lower alkyl, loweralkoxy, halogen, trifluoromethyl, nitro, cyano, hydroxy, amido, dimethylamino or

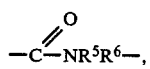

wherein $R^5$ and $R^6$ are selected from hydrogen or loweralkyl, and Ar may include one or two intervening methylene groups attached to B, $R^1$ and $R^2$ are selected from the group consisting of hydrogen, loweralkyl, cycloalkyl, phenyl or phenyl-loweralkyl wherein phenyl may be substituted by halogen, loweralkyl, loweralkoxy, allyl or loweralkoxy (1-8 C)-loweralkyl (2-8 C), X is selected from oxygen or sulfur, B is selected from the group consisting of —S—,

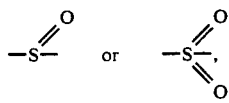

R³ and R⁴ are selected from the group consisting of hydrogen, loweralkyl, phenyl and phenyl-loweralkyl wherein phenyl may be substituted by halogen, loweralkyl or lower-alkoxy and may be the same or different, or R³ and R⁴ taken together with the adjacent nitrogen form a heterocyclic residue;

alk¹ and alk² are selected from the group consisting of loweralkylene or loweralkylene-loweralkyl and may be the same or different, and the pharmaceutically acceptable addition salts and hydrates of the salts and free bases.

2. A compound of claim 1 which is N-[2-[(4-chlorophenyl)thio]ethyl]N'-[2-(dimethylamino)ethyl]-N-(1-methylethyl)urea or a pharmaceutically acceptable salt thereof.

3. The compound of claim 2 which is N-[2-[(4-chlorophenyl)thio]ethyl]-N'-[2-(dimethylamino)ethyl]-N-(1-methylethyl)urea fumarate[1:1.5].

4. A compound of claim 1 which is N'-[2-(dimethylamino)ethyl]-N-(1-methylethyl)-N-[2-[(2-naphthylene)thio]ethyl]urea or a pharmaceutically acceptable salt thereof.

5. The compound of claim 4 which is N'-[2-(dimethylamino)ethyl]-N-(1-methylethyl)-N-[2-[(2-naphthylene)thio]ethyl]urea, succinate[1:1.5].

6. A compound of claim 1 which is N-[2-[(4-chlorophenyl)sulfonyl)ethyl]-N'-[2-(dimethylamino)ethyl]-N-(1-methylethyl)urea or a pharmaceutically acceptable salt thereof.

7. The compound of claim 6 which is N-[2-[(4-chlorophenyl)sulfonyl)ethyl]-N'-[2-(dimethylamino)ethyl]-N-(1-methylethyl)urea maleate[1:1].

8. A compound of claim 1 which is N-[2-[(4-chlorophenyl)sulfonyl]ethyl]-N'-[2-(diethylamino)ethyl]-N-(1-methylethyl)urea or a pharmaceutically acceptable salt thereof.

9. The compound of claim 8 which is N-[2-[(4-chlorophenyl)sulfonyl]ethyl]-N'-[2-(diethylamino)ethyl]-N-(1-methylethyl)urea, tartrate[1:1].

10. A compound of claim 1 which is N-[2-[(4-chlorophenyl)sulfonyl]ethyl]-N'-[2-(dimethylamino)ethyl]-N'-(1-methylethyl)urea or a pharmaceutically acceptable salt thereof.

11. The compound of claim 10 which is N-[2-[(4-chlorophenyl)sulfonyl]ethyl]-N'-[2-(dimethylamino)ethyl]-N'-(1-methylethyl)urea, maleate[1:1].

12. A compound of claim 1 which is N-[2-[(4-chlorophenyl)sulfonyl]ethyl]-N'-(dimethylamino)ethyl]-N-(1-methylethyl)thiourea or a pharmaceutically acceptable salt thereof.

13. The compound of claim 12 which is N-[2-[(4-chlorophenyl)sulfonyl]ethyl]-N'-[2-(dimethylamino)ethyl]-N-(1-methylethyl)thiourea, hemifumarate.

14. A compound of claim 1 which is N-[2-[(4-chlorophenyl)sulfinyl]ethyl]-N'-[2-(dimethylamino)ethyl]-N-(1-methylethyl)urea or a pharmaceutically acceptable salt thereof.

15. The compound of claim 14 which is N-[2-[(4-chlorophenyl)sulfinyl]ethyl[-N'-[2-(dimethylamino)ethyl]-N-(1-methylethyl)urea fumarate[1:1].

16. A compound of claim 1 which is N'-[2-(dimethylamino)ethyl]-N-(1-methylethyl)-N-[2-(phenylsulfonyl)ethyl]urea or a pharmaceutically acceptable salt thereof.

17. The compound of claim 16 which is N'-[2-(dimethylamino)ethyl]-N-(1-methylethyl)-N-[2-(phenylsulfonyl)ethyl]urea, maleate[1:1].

18. A compound of claim 1 which is N'-[2-(diethylamino)ethyl]-N-(1-methylethyl)-N-[2-(phenylsulfonyl)ethyl]urea or a pharmaceutically acceptable salt thereof.

19. The compound of claim 18 whichis N'-[2-(diethylamino)ethyl]-N-(1-methylethyl)-N-[2-(phenylsulfonyl)ethyl]urea, maleate[1:1].

20. A compound of claim 1 which is N'-[2-(dimethylamino)ethyl]-N-(1-methylethyl)-N-[2-[(1-naphthalenesulfonyl)]ethyl]urea or a pharmaceutically acceptable salt thereof.

21. The compound of claim 20 which is N'-[2-(dimethylamino)ethyl]-N-(1-methylethyl)-N-[2-[(1-naphthalenesulfonyl)ethyl]urea maleate[1:1].

22. A compound of claim 1 which is N-(1-methylethyl)-N-[2-(phenylsulfonyl)ethyl]-N'-[2-(1-pyrrolidinyl)ethyl]urea or a pharmaceutically acceptable salt thereof.

23. A compound of claim 22 which is N-(1-methylethyl)-N-[2-(phenylsulfonyl)ethyl]-N'-[2-(1-pyrrolidinyl)ethyl]urea maleate[1:1].

24. A compound of claim 1 which is N'-(2-aminoethyl)-N-(1-methylethyl)-N-[2-(phenylsulfonyl)ethyl]urea or a pharmaceutically acceptable salt thereof.

25. The compound of claim 24 which is N'-(2-aminoethyl)-N-(1-methylethyl)-N-[2-(phenylsulfonyl)ethyl]urea maleate[1:1].

26. A compound of claim 1 which is N'-[2-(dimethylamino)ethyl]-N-(1-methylethyl)-N-[2-(1-naphthalenylthio)ethyl]urea or a pharmaceutically acceptable salt thereof.

27. The compound of claim 26 which is N'-[2-(dimethylamino)ethyl]-N-(1-methylethyl)-N-[2-(1-naphthalenylthio)ethyl]urea, oxalate[1:1].

28. A compound of claim 1 which is N'-[2-(diethylamino)ethyl]-N-(1-methylethyl)-N-[2-[(4-methylphenyl)sulfonyl]ethyl]urea or a pharmaceutically acceptable salt thereof.

29. The compound of claim 28 which is N'-[2-(diethylamino)ethyl]-N-(1-methylethyl)-N-[2-[(4-methylphenyl)sulfonyl]ethyl]urea, tartrate[1:1].

30. A compound of claim 1 which is N-[2-[(3,4-dichlorophenyl)sulfonyl]ethyl]-N'-(dimethylamino)ethyl]-N-(1-methylethyl)urea or a pharmaceutically acceptable salt thereof.

31. The compound of claim 30 which is N-[2-[(3,4-dichlorophenyl)sulfonyl]ethyl]-N'-(dimethylamino)ethyl]-N-(1-methylethyl)urea maleate[1:1].

32. A compound of claim 1 which is N'-[2-(diethylamino)ethyl]-N-(1-methylethyl)-N-[2-[(4-methylphenyl)sulfinyl]ethyl]urea or a pharmaceutically acceptable salt thereof.

33. The compound of claim 1 which is N'-[2-(diethylamino)ethyl]-N-(1-methylethyl)-N-[2-[(4-methylphenyl)sulfinyl]ethyl]urea hemihydrate.

34. A compound of claim 1 which is N'-[3-(diethylamino)propyl]-N-(1-methylethyl)-N-[3-(phenylsulfonyl)propyl]urea or a pharmaceutically acceptable salt thereof.

35. The compound of claim 34 which is N'-[3-(diethylamino)propyl]-N-(1-methylethyl)-N-[3-(phenylsulfonyl)propyl]urea oxalate[1:1]hemihydrate.

36. A compound of claim 1 which is N'-[2-(diethylamino)ethyl]-N-(1-methylethyl)-N-[3-(phenylsulfonyl)propyl]urea or a pharmaceutically acceptable salt thereof.

37. The compound of claim 36 which is N'-[2-(diethylamino)ethyl]-N-(1-methylethyl)-N-[3-phenylsulfonyl)propyl]urea oxalate[1:1]hemihydrate.

38. A compound of claim 1 which is N'-[3-(diethylamino)propyl]-N-(1-methylethyl)-N-[2-(phenylsulfonyl)ethyl]urea or a pharmaceutically acceptable salt thereof.

39. The compound of claim 1 which is N'-[3-(diethylamino)propyl]-N-(1-methylethyl)-N-[2-(phenylsulfonyl)ethyl]urea ¼ hydrate.

40. A compound of claim 1 which is N'-[2-(diethylamimo)ethyl]-N-[2-[(4-fluorophenyl)sulfonyl]ethyl]-N-(1-methylethyl)urea or a pharmaceutically acceptable salt thereof.

41. A compound of claim 1 which is N-(1-methylethyl)-N'-[2-[bis(1-methylethyl)amino]ethyl]-N-[2-(phenylsulfonyl)ethyl]urea or a pharmaceutically acceptable salt thereof.

42. A compound of claim 1 which is N-(1-methylethyl)-N'-[2-[methyl-(2-phenylethyl)amino]ethyl]-N-[2-(phenylsulfonyl)ethyl]urea or a pharmaceutically acceptable salt thereof.

43. A compound of claim 1 which is N-(1-methylethyl)-N'-[2-[methyl-(2-phenylethyl)amino]ethyl]-N-[2-(phenylsulfonyl)ethyl]urea hemihydrate.

44. A compound of claim 1 which is N-(1-methylethyl)-N-[2-[methyl(phenylmethyl)amino]ethyl]-N-[2-(phenylsulfonyl)ethyl]urea or a pharmaceutically acceptable salt thereof.

45. A compound of claim 1 which is N'-[2-(ethylamino)ethyl]-N-(1-methylethyl)-N-[2-(phenylsulfonyl)ethyl]urea or a pharmaceutically acceptable salt thereof.

46. The compound of claim 45 which is N'-[2-(ethylamino)ethyl]-N-(1-methylethyl)-N-[2-(phenylsulfonyl)ethyl]urea oxalate[1:1].

47. A compound of claim 1 which is N'-[2-(hexahydro-1H-azepin-1-yl)ethyl]-N-(1-methylethyl)-N-[2-(phenylsulfonyl)ethyl]urea or a pharmaceutically acceptable salt thereof.

48. The compound of claim 47 which is N'-[2-(hexahydro-1H-azepin-1-yl)ethyl]-N-(1-methylethyl)-N-[2-(phenylsulfonyl)ethyl]urea oxalate[1:1].

49. A compound of claim 1 which is N-(1-methylethyl)-N'-[2-[(methyl)(phenyl)amino]ethyl]-N-[2-(phenylsulfonyl)ethyl]urea or a pharmaceutically acceptable salt thereof.

50. A compound of claim 1 which is N'-[2-(diethylamino)ethyl]-N-(2-phenylethyl)-N-[2-(phenylsulfonyl)ethyl]urea or a pharmaceutically acceptable salt thereof.

51. The compound of claim 50 which is N'-[2-(diethylamino)ethyl]-N-(2-phenylethyl)-N-[2-(phenylsulfonyl)ethyl]urea oxalate[1:1]hemihydrate.

52. A compound of claim 1 which is N-(1-methylethyl)-N'-[2-(4-morpholinyl)ethyl]-N-[2-(phenylsulfonyl)ethyl]urea or a pharmaceutically acceptable salt thereof.

53. The compound of claim 52 which is N-(1-methylethyl)-N'-[2-(4-morpholinyl)ethyl]-N-[2-(phenylsulfonyl)ethyl]urea maleate[1:1].

54. A compound of claim 1 which is N-(1-methylethyl)-N-[2-(phenylsulfonyl)ethyl]-N'-[2-(1-piperidinyl)ethyl]urea or a pharmaceutically acceptable salt thereof.

55. The compound of claim 54 which is N-(1-methylethyl)-N-[2-(phenylsulfonyl)ethyl]-N'-[2-(1-piperidinyl)ethyl]urea maleate[1:1].

56. A therapeutic composition for the treatment of cardiac arrhythmias comprising (a) an effective amount of a compound selected from the group having the formula:

$$Ar-B-alk^1-\underset{\underset{R^1}{|}}{N}-\underset{\underset{}{\overset{\overset{X}{\|}}{C}}}{}-\underset{\underset{R^2}{|}}{N}-alk^2-N\underset{R^4}{\overset{R^3}{\diagup}}$$

wherein;
Ar is selected from the group consisting of 1 and 2-naphthyl, 2,3-dihydro-1H-inden-4(or 5)yl, 2-furanyl, phenyl or phenyl substituted by 1–3 radicals which may be the same or different selected from the group consisting of loweralkyl, loweralkoxy, halogen, trifluoromethyl, nitro, cyano, hydroxy, amino, dimethylamino or $$-\overset{\overset{O}{\|}}{C}-NR^5R^6-,$$

wherein $R^5$ and $R^6$ are selected from hydroxy or loweralkyl, and Ar may include one or two intervening methylene groups attached to B,
$R^1$ and $R^2$ are selected from the group consisting of hydrogen, loweralkyl, cycloalkyl, phenyl or phenyl-loweralkyl wherein phenyl may be substituted by halogen, loweralkyl, loweralkoxy, allyl or loweralkoxy (1–8 C)-loweralkyl (2–8 C),
X is selected from oxygen or sulfur,
B is selected from the group consisting of —S—, $$-\overset{\overset{O}{\|}}{S}- \quad \text{or} \quad -\overset{\overset{O}{\|}}{\underset{\underset{O}{\|}}{S}}-,$$

$R^3$ and $R^4$ are selected from the group consisting of hydrogen, loweralkyl, phenyl and phenyl-loweralkyl wherein phenyl may be substituted by halogen, loweralkyl or loweralkoxy and may be the same or different, or $R^3$ and $R^4$ taken together with the adjacent nitrogen form a heterocyclic residue,
alk¹ and alk² are selected from the group consisting of loweralkylene or loweralkylene-loweralkyl and may be the same or different, and the pharmaceutically acceptable addition salts and hydrates of the salts and free bases,
and (b) a pharmaceutically acceptable carrier therefor.

57. A therapeutic composition of claim 56 wherein the compound administered is N-[2-[(4-chlorophenyl)thio]ethyl]-N-[2-(dimethylamino)ethyl]-N-(1-methylethyl)urea or a pharmaceutically acceptable salt thereof.

58. A therapeutic composition of claim 56 wherein the compound administered is N'-[2-(dimethylamino)ethyl]-N-(1-methylethyl)-N-[2-[(2-naphthylene)thio]ethyl]urea or a pharmaceutically acceptable salt thereof.

59. A therapeutic composition of claim 56 wherein the compound administered is N-[2-[(4-chlorophenyl)sulfonyl]ethyl]-N'-[2-(dimethylamino)ethyl]-N-(1- methylethyl)urea or a pharmaceutically acceptable salt thereof.

60. A therapeutic composition of claim 56 wherein the compound administered is N-[2-[(4-chlorophenyl)sulfonyl]ethyl]-N'-[2-(diethylamino)ethyl]-N-(1-methylethyl)urea or a pharmaceutically acceptable salt thereof.

61. A therapeutic composition of claim 56 wherein the compound administered is N-[2-[(4-chlorophenyl)sulfonyl]ethyl]-N'-[2-(dimethylamino)ethyl]-N'-(1-methylethyl)urea or a pharmaceutically acceptable salt thereof.

62. A therapeutic composition of claim 56 wherein the compound administered is N-[2-[(4-chlorophenyl)sulfonyl]ethyl]-N'-(dimethylamino)ethyl]-N-(1-methylethyl)thiourea or a pharmaceutically acceptable salt thereof.

63. A therapeutic composition of claim 56 wherein the compound administered is N-[2-[(4-chlorophenyl)sulfinyl]ethyl]-N'-[2-(dimethylamino)ethyl]-N-(1-methylethyl)urea or a pharmaceutically acceptable salt thereof.

64. A therapeutic composition of claim 56 wherein the compound administered is N'-[2-(dimethylamino)ethyl]-N-(1-methylethyl)-N-[2-(phenylsulonyl)ethyl]urea or a pharmaceutically acceptable salt thereof.

65. A therapeutic composition of claim 56 wherein the compound administered is N'-[2-(dimethylamino)ethyl]-N-(1-methylethyl)-N-[2-[(1-naphthalenesulfonyl)]ethyl]urea or a pharmaceutically acceptable salt thereof.

66. A therapeutic composition of claim 56 wherein the compound administered is N'-[2-(diethylamino)ethyl]-N-(1-methylethyl)-N-[2-(phenylsulfonyl)ethyl]urea or a pharmaceutically acceptable salt thereof.

67. A therapeutic composition of claim 56 wherein the compound administered is N-(1-methylethyl)-N-[2-(phenylsulfonyl)ethyl]-N'-2-(1-pyrrolidinyl)ethyl]urea or a pharmaceutically acceptable salt thereof.

68. A therapeutic composition of claim 56 wherein the compound administered is N'-(2-aminoethyl)-N-(1-methylethyl)-N-[2-(phenylsulfonyl)ethyl]urea or a pharmaceutically acceptable salt thereof.

69. A therapeutic composition of claim 56 wherein the compound administered is N'-[2-(dimethylamino)ethyl]-N-(1-methylethyl)-N-[2-(1-naphthalenylthio)ethyl]urea or a pharmaceutically acceptable salt thereof.

70. A therapeutic composition of claim 56 wherein the compound administered is N'-[2-(diethylamino)ethyl]-N-(1-methylethyl)-N-[2-[(4-methylphenyl)sulfonyl]ethyl]urea or a pharmaceutically acceptable salt thereof.

71. A therapeutic composition of claim 56 wherein the compound administered is N-[2-[(3,4-dichlorophenyl)sulfonyl]ethyl]-N'-(dimethylamino)ethyl]-N-(1-methylethyl)urea or a pharmaceutically acceptable salt thereof.

72. A therapeutic composition of claim 56 wherein the compound administered is N'-[2-(diethylamino)ethyl]-N-(1-methylethyl)-N-[2-[(4-methylphenyl)sulfinyl]ethyl]urea or a pharmaceutically acceptable salt thereof.

73. A therapeutic composition of claim 56 wherein the compound administered is N'-[3-(diethylamino)propyl]-N-(1-methylethyl)-N-[3-(phenylsulfonyl)propyl]urea or a pharmaceutically acceptable salt thereof.

74. A therapeutic composition of claim 56 wherein the compound administered is N'-[2-(diethylamino)ethyl]-N-(1-methylethyl)-N-[3-(phenylsulfonyl)propyl]urea or a pharmaceutically acceptable salt thereof.

75. A therapeutic composition of claim 56 wherein the compound administered is N'-[3-(diethylamino)propyl]-N-(1-methylethyl)-N-[2-(phenylsulfonyl)ethyl]urea or a pharmaceutically acceptable salt thereof.

76. A therapeutic composition of claim 56 wherein the compound administered is N'-[2-(diethylamino)ethyl]-N-[2-[(4-fluorophenyl)sulfonyl]ethyl]-N-(1-methylethyl)urea or a pharmaceutically acceptable salt thereof.

77. A therapeutic composition of claim 56 wherein the compound administered is N-(1-methylethyl)-N'-[2-[bis(1-methylethyl)amino]ethyl]-N-[2-(phenylsulfonyl)ethyl]urea or a pharmaceutically acceptable salt thereof.

78. A therapeutic composition of claim 56 wherein the compound administered is N-(1-methylethyl)-N'-[2-[methyl(2-phenylethyl)amino]ethyl]-N-[2-(phenylsulfonyl)ethyl]urea or a pharmaceutically acceptable salt thereof.

79. A therapeutic composition of claim 56 wherein the compound administered is N-(1-methylethyl)-N-[2-methyl(phenylmethyl)amino]ethyl]-N-[2-(phenylsulfonyl)ethyl]urea or a pharmaceutically acceptable salt thereof.

80. A therapeutic composition of claim 56 wherein the compound administered is N'-[2-(ethylamino)ethyl]-N-(1-methylethyl)-N-[2-(phenylsulfonyl)ethyl]urea or a pharmaceutically acceptable salt thereof.

81. A therapeutic composition of claim 56 wherein the compound administered is N'-[2-(hexahydro-1H-azepin-1-yl)ethyl]-N-(1-methylethyl)-N-[2-(phenylsulfonyl)ethyl]urea or a pharmaceutically acceptable salt thereof.

82. A therapeutic composition of claim 56 wherein the compound administered is N-(1-methylethyl)-N'-[2-[(methyl)(phenyl)amino]ethyl-N-[2-(phenylsulfonyl)ethyl]urea or a pharmaceutically acceptable salt thereof.

83. A therapeutic composition of claim 56 wherein the compound administered is N'-[2-(diethylamino)ethyl]-N-(2-phenylethyl)-N-[2-(phenylsulfonyl)ethyl]urea or a pharmaceutically acceptable salt thereof.

84. A therapeutic composition of claim 56 wherein the compound administered is N-(1-methylethyl)-N'-[2-(4-morpholinyl)ethyl]-N-[2-(phenylsulfonyl)ethyl]urea or a pharmaceutically acceptable salt thereof.

85. A therapeutic composition of claim 56 wherein the compound administered is N-(1-methylethyl)-N-[2-(phenylsulfonyl)ethyl]-N'-[2-(1-piperidinyl)ethyl]urea or a pharmaceutically acceptable salt thereof.

86. A compound of claim 1 which is N-[2-(diethylamino)ethyl]-N-ethyl-N'-(1-methylethyl)-N'-[2-(phenylsulfonyl)ethyl]urea or a pharmaceutically acceptable salt thereof.

87. A compound of claim 1 which is N-[2-(diethylamino)ethyl]-N-ethyl-N'-[2(phenylsulfonyl)ethyl]urea or a pharmaceutically acceptable salt thereof.

88. A compound of claim 1 which is N-[2-(diethylamino)ethyl]-N'-[2-(phenylsulfonyl)ethyl]urea or a pharmaceutically acceptable salt thereof.

89. A compound of claim 1 which is N'-[2-(diethylamino)ethyl]-N-[2-[(4-methoxyphenyl)sulfonyl]ethyl]-N-(1-methylethyl)urea or a pharmaceutically acceptable salt thereof.

90. A compound of claim 1 which is N'-[3-(diethylamino)propyl]-N-(1-methylethyl)-N-[2-(phenylsulfonyl)ethyl] or a pharmaceutically acceptable salt thereof.

91. A compound of claim 1 which is N'-[2-(diethylamino)ethyl]-N-[2-[4-(1,1-dimethylethyl)phenyl]sulfonyl]ethyl-N-(1-methylethyl)urea or a pharmaceutically acceptable salt thereof.

92. A compound of claim 1 which is N'-[2-(diethylamino)ethyl]-N-(1-methylethyl)-N-[2-(phenylthio)ethyl]urea or a pharmaceutically acceptable salt thereof.

93. A compound of claim 1 which is N'-[2-(diethylamino)ethyl]-N-(1-methylethyl)-N-[2-(phenylsulfonyl)ethyl]thiourea or a pharmaceutically acceptable salt thereof.

94. A compound of claim 1 which is N'-[2-(diethylamino)ethyl]-N-(1-methylethyl)-N-[2-[(phenylmethyl)sulfonyl]ethyl]urea or a pharmaceutically acceptable salt thereof.

95. A compound of claim 1 which is N'-[3-(diethylamino)propyl]-N-(1-methylethyl)-N-[2-[(phenylmethyl)sulfonyl]ethyl]urea or a pharmaceutically acceptable salt thereof.

96. A compound of claim 1 which is N'-[2-(diethylamino)ethyl]-N-ethyl-N-[2-(phenylsulfonyl)ethyl]urea or a pharmaceutically acceptable salt thereof.

97. A compound of claim 1 which is N'-[4-(diethylamino)butyl]-N-(1-methylethyl)-N-[2-(phenylsulfonyl)ethyl]urea or a pharmaceutically acceptable salt thereof.

98. A compound of claim 1 which is N'-[2-(diethylamino)-1-methylethyl]-N-(1-methylethyl)-N-[2-(phenylsulfonyl)ethyl]urea or a pharmaceutically acceptable salt thereof.

99. A compound of claim 1 which is N-(1-methylethyl)-N-[2-(phenylsulfonyl)ethyl]-N'-[3-(1-piperidinyl)propyl]urea or a pharmaceutically acceptable salt thereof.

100. A compound of claim 1 which is N'-[2-(diethylamino)ethyl]-N-(1-methylethyl)-N-[2-(phenylsulfinyl)ethyl]urea or a pharmaceutically acceptable salt thereof.

101. A compound of claim 1 which is N'-[2-(diethylamino)ethyl]-N-(phenylmethyl)-N-[2-(phenylsulfonyl)ethyl]urea or a pharmaceutically acceptable salt thereof.

102. A compound of claim 1 which is N-[2-(diethylamino)ethyl]-N-(1-methylethyl)-N'-[2-(phenylsulfonyl)ethyl]urea or a pharmaceutically acceptable salt thereof.

103. A compound of claim 1 which is N'-[5-(diethylamino)pentyl]-N-(1-methylethyl)-N-[2-(phenylsulfonyl)ethyl]urea or a pharmaceutically acceptable salt thereof.

104. A compound of claim 1 which is N-(1-methylethyl)-N'-[3-(4-methyl-1-piperazinyl)propyl]-N-[2-(phenylsulfonyl)ethyl]urea or a pharmaceutically acceptable salt thereof.

105. A compound of claim 1 which is N'-[2-(diethylamino)ethyl]-N-(1-methylethyl)-N-[1-methyl-2-(phenylsulfonyl)ethyl]urea or a pharmaceutically acceptable salt thereof.

106. A compound of claim 1 which is N-[2-(diethylamino)ethyl]-N-methyl-N'-(1-methylethyl)-N'-[2-(phenylsulfonyl)ethyl]urea or a pharmaceutically acceptable salt thereof.

107. A compound of claim 1 which is N'-[2-(diethylamino)ethyl]-N-(1-methylethyl)-N-[4-(phenylsulfonyl)butyl]urea or a pharmaceutically acceptable salt thereof.

108. A compound of claim 1 which is N'-[2-(diethylamino)ethyl]-N-(1-methylethyl)-N-[5-(phenylsulfonyl)pentyl]urea or a pharmaceutically acceptable salt thereof.

109. A compound of claim 1 which is N'-[2-(diethylamino)ethyl]-N-(3-ethoxypropyl)-N-[2-(phenylsulfonyl)ethyl]urea or a pharmaceutically acceptable salt thereof.

110. A compound of claim 1 which is N'-[2-(diethylamino)ethyl]-N-(2-methoxyethyl)-N-[2-(phenylsulfonyl)ethyl]urea or a pharmaceutically acceptable salt thereof.

111. A compound of claim 1 which is N'-[2-(diethylamino)ethyl]-N-[2-[(4-ethoxyphenyl)sulfonyl]ethyl]-N-(1-methylethyl)urea or a pharmaceutically acceptable salt thereof.

112. A compound of claim 1 which is N'-[2-(diethylamino)ethyl]-N-[2-(phenylsulfonyl)ethyl]-N-(2-propenyl)urea or a pharmaceutically acceptable salt thereof.

113. A therapeutic composition of claim 56 wherein the compound administered is N-[2-(diethylamino)ethyl]-N-ethyl-N'-(1-methylethyl)-N'-[2-(phenylsulfonyl)ethyl]urea or a pharmaceutically acceptable salt thereof.

114. A therapeutic composition of claim 56 wherein the compound administered is N-[2-(diethylamino)ethyl]-N-ethyl-N'-[2-(phenylsulfonyl)ethyl]urea or a pharmaceutically acceptable salt thereof.

115. A therapeutic composition of claim 56 wherein the compound administered is N-[2-(diethylamino)ethyl]-N'-[2-(phenylsulfonyl)ethyl]urea or a pharmaceutically acceptable salt thereof.

116. A therapeutic composition of claim 56 wherein the compound administered is N'-[2-(diethylamino)ethyl]-N-[2-[4-methoxyphenyl)sulfonyl]ethyl]-N-(1-methylethyl)urea or a pharmaceutically acceptable salt thereof.

117. A therapeutic composition of claim 56 wherein the compound administered is N'-[3-(diethylamino)propyl]-N-(1-methylethyl)-N-[2-(phenylsulfonyl)ethyl] or a pharmaceutically acceptable salt thereof.

118. A therapeutic composition of claim 56 wherein the compound administered is N'-[2-(diethylamino)ethyl]-N-[2-[4-(1,1-dimethylethyl)phenyl]sulfonyl]ethyl-N-(1-methylethyl)urea or a pharmaceutically acceptable salt thereof.

119. A therapeutic composition of claim 56 wherein the compound administered is N'-[2-(diethylamino)ethyl]-N-(1-methylethyl)-N-[2-(phenylthio)ethyl]urea or a pharmaceutically acceptable salt thereof.

120. A therapeutic composition of claim 56 wherein the compound administered is N'-[2-(diethylamino)ethyl]-N-(1-methylethyl)-N-[2-(phenylsulfonyl)ethyl]thiourea or a pharmaceutically acceptable salt thereof.

121. A therapeutic composition of claim 56 wherein the compound administered is N'-[2-(diethylamino)ethyl]-N-(1-methyethyl)-N-[2-[(phenylmethyl)sulfonyl]ethyl]urea or a pharmaceutically acceptable salt thereof.

122. A therapeutic composition of claim 56 wherein the compound is N'-[3-(diethylamino)propyl]-N-(1-methylethyl)-N-[2-[(phenylmethyl)sulfonyl]ethyl]urea or a pharmaceutically acceptable salt thereof.

123. A therapeutic composition of claim 56 wherein the compound administered is N'-[2-(diethylamino)ethyl]-N-ethyl-N-[2-(phenylsulfonyl)ethyl]urea or a pharmaceutically acceptable salt thereof.

124. A therapeutic composition of claim 56 wherein the compound administered is N'-[4-(diethylamino)butyl]-N-(1-methylethyl)-N-[2-(phenylsulfonyl)ethyl]urea or a pharmaceutically acceptable salt thereof.

125. A therapeutic composition of claim 56 wherein the compound administered is N'-[2-(diethylamino)-1-methylethyl]-N-(1-methylethyl)-N-[2-(phenylsulfonyl)ethyl]urea or a pharmaceutically acceptable salt thereof.

126. A therapeutic composition of claim 56 wherein the compound administered is N-(1-methylethyl)-N-[2-(phenylsulfonyl)ethyl]-N'-[3-(1-piperidinyl)propyl]urea or a pharmaceutically acceptable salt thereof.

127. A therapeutic composition of claim 56 wherein the compound administered is N'-[2-(diethylamino)ethyl]-N-(1-methylethyl)-N-[2-(phenylsulfinyl)ethyl]urea or a pharmaceutically acceptable salt thereof.

128. A therapeutic composition of claim 56 wherein the compound administered is N'-[2-(diethylamino)ethyl]-N-(phenylmethyl)-N-[2-(phenylsulfonyl)ethyl]urea or a pharmaceutically acceptable salt thereof.

129. A therapeutic composition of claim 56 wherein the compound administered is N-[2-(diethylamino)ethyl]-N-(1-methylethyl)-N'-[2-(phenylsulfonyl)ethyl]urea or a pharmaceutically acceptable salt thereof.

130. A therapeutic composition of claim 56 wherein the compound administered is N'-[5-(diethylamino)pentyl]-N-(1-methylethyl)-N-[2-(phenylsulfonyl)ethyl]urea or a pharmaceutically acceptable salt thereof.

131. A therapeutic composition of claim 56 wherein the compound administered is N-(1-methylethyl)-N'-[3-(4-methyl-1-piperazinyl)propyl]-N-[2-(phenylsulfonyl)ethyl]urea or a pharmaceutically acceptable salt thereof.

132. A therapeutic composition of claim 56 wherein the compound administered is N'-[2-(diethylamino)ethyl]-N-(1-methylethyl)-N-[1-methyl-2-(phenylsulfonyl)ethyl]urea or a pharmaceutically acceptable salt thereof.

133. A therapeutic composition of claim 56 wherein the compound administered is N-[2-(diethylamino)ethyl]-N-methyl-N'-(1-methylethyl)-N'-[2-(phenylsulfonyl)ethyl]urea or a pharmaceutically acceptable salt thereof.

134. A therapeutic composition of claim 56 wherein the compound administered is N'-[2-(diethylamino)ethyl]-N-(1-methylethyl)-N-[4-(phenylsulfonyl)butyl]urea or a pharmaceutically acceptable salt thereof.

135. A therapeutic composition of claim 56 wherein the compound administered is N'-[2-(diethylamino)ethyl]-N-(1-methylethyl)-N-[5-(phenylsulfonyl)pentyl]urea or a pharmaceutically acceptable salt thereof.

136. A therapeutic composition of claim 56 wherein the compound administered is N'-[2-(diethylamino)ethyl]-N-(3-ethoxypropyl)-N-[2-(phenylsulfonyl)ethyl]urea or a pharmaceutically acceptable salt thereof.

137. A therapeutic composition of claim 56 wherein the compound administered is N'-[2-(diethylamino)ethyl]-N-(2-methoxyethyl)-N-[2-(phenylsulfonyl)ethyl]urea or a pharmaceutically acceptable salt thereof.

138. A therapeutic composition of claim 56 wherein the compound administered is N'-[2-(diethylamino)ethyl]-N-[2-[(4-ethoxyphenyl)sulfonyl]ethyl]-N-(1-methylethyl)urea or a pharmaceutically acceptable salt thereof.

139. A therapeutic composition of claim 56 wherein the compound administered is N'-[2-(diethylamino)ethyl]-N-[2-(phenylsulfonyl)ethyl]-N-(2-propenyl)urea or a pharmaceutically acceptable salt thereof.

140. A compound selected from the group having the formula:

$$Ar-B-alk^1-\underset{\underset{R^1}{|}}{N}-\underset{\underset{}{\overset{X}{\|}}}{C}-\underset{\underset{R^2}{|}}{N}-alk^2-N\diagdown\begin{matrix}R^3\\R^4\end{matrix}$$

wherein;

Ar is selected from the group consisting of 1 and 2-naphthyl, 2,3-dihydro-1H-inden-4(or 5)yl, 2-furanyl, phenyl or phenyl substituted by 1–3 radicals which may be the same or different selected from the group consisting of lower-alkyl, loweralkoxy, halogen, trifluoromethyl, nitro, cyano, or $$-\underset{\underset{}{\overset{O}{\|}}}{C}-NR^5R^6-,$$

wherein $R^5$ and $R^6$ are selected from hydrogen or loweralkyl, and Ar may include one intervening methylene group attached to B, $R^1$ and $R^2$ are selected from the group consisting of hydrogen, loweralkyl, cycloalkyl, phenyl or phenyl-lower-alkyl wherein phenyl may be substituted by halogen, lower-alkyl or loweralkoxy, X is selected from oxygen or sulfur, B is selected from the group consisting of —S—, $$-\underset{\underset{}{\overset{O}{\|}}}{S}-\quad \text{or} \quad -\underset{\underset{\overset{}{\|}}{O}}{\overset{\overset{O}{\|}}{S}}-,$$

$R^3$ and $R^4$ are selected from the group consisting of hydrogen, loweralkyl, phenyl and phenyl-loweralkyl wherein phenyl may be substituted by halogen, loweralkyl or lower-alkoxy and may be the same or different, or $R^3$ and $R^4$ taken together with the adjacent nitrogen form a heterocyclic residue, $alk^1$ and $alk^2$ are selected from the group consisting of loweralkylene or loweralkylene-loweralkyl and may be the same or different, and the pharmaceutically acceptable addition salts and hydrates of the salts and free bases.

* * * * *